US012612388B2

(12) United States Patent
Su et al.

(10) Patent No.: US 12,612,388 B2
(45) Date of Patent: Apr. 28, 2026

(54) RECEPTOR-INTERACTING PROTEIN 1 INHIBITORS INCLUDING PIPERAZINE HETEROCYCLIC AMIDE UREAS

(71) Applicant: SIRONAX LTD., Grand Cayman (KY)

(72) Inventors: Yaning Su, Beijing (CN); Zhiyuan Zhang, San Diego, CA (US); Zhaolan Zhang, Beijing (CN); Yanping Xu, Beijing (CN)

(73) Assignee: SIRONAX LTD., Grand Cayman (KY)

( * ) Notice: Subject to any disclaimer, the term of this patent is extended or adjusted under 35 U.S.C. 154(b) by 651 days.

(21) Appl. No.: 17/998,568

(22) PCT Filed: May 20, 2021

(86) PCT No.: PCT/CN2021/094986

§ 371 (c)(1),
(2) Date: Nov. 11, 2022

(87) PCT Pub. No.: WO2021/233394

PCT Pub. Date: Nov. 25, 2021

(65) Prior Publication Data

US 2023/0192662 A1 Jun. 22, 2023

(30) Foreign Application Priority Data

May 20, 2020 (WO) ................ PCT/CN2020/091429

(51) Int. Cl.

| | |
|---|---|
| ***C07D 403/12*** | (2006.01) |
| ***A61P 39/00*** | (2006.01) |
| ***C07D 401/14*** | (2006.01) |
| ***C07D 403/14*** | (2006.01) |
| ***C07D 491/107*** | (2006.01) |

(52) U.S. Cl.

CPC ............ *C07D 403/12* (2013.01); *A61P 39/00* (2018.01); *C07D 401/14* (2013.01); *C07D 403/14* (2013.01); *C07D 491/107* (2013.01)

(58) Field of Classification Search

CPC . C07D 403/12; C07D 401/14; C07D 491/107
See application file for complete search history.

(56) References Cited

U.S. PATENT DOCUMENTS

| | | | |
|---|---|---|---|
| 6,756,394 | B1 | 6/2004 | Yuan et al. |
| 8,278,344 | B2 | 10/2012 | Cuny et al. |
| 9,974,762 | B2 | 5/2018 | Zhang et al. |
| 10,092,529 | B2 | 10/2018 | Zhang et al. |
| 2003/0083386 | A1 | 5/2003 | Yuan et al. |
| 2009/0099242 | A1 | 4/2009 | Cuny et al. |
| 2010/0317701 | A1 | 12/2010 | Cuny et al. |
| 2011/0144169 | A1 | 6/2011 | Cuny et al. |
| 2012/0122889 | A1 | 5/2012 | Yuan et al. |
| 2012/0309795 | A1 | 12/2012 | Cuny et al. |

FOREIGN PATENT DOCUMENTS

| | | | | |
|---|---|---|---|---|
| CN | 102316735 A | 1/2012 | | |
| CN | 103404518 A | 11/2013 | | |
| CN | 107624111 A | 1/2018 | | |
| JP | H04249551 A | 9/1992 | | |
| JP | 2005526091 A | 9/2005 | | |
| JP | 2006522127 A | 9/2006 | | |
| JP | 2010532381 A | 10/2010 | | |
| JP | 2013112740 A | 6/2013 | | |
| JP | 2013522253 A | 6/2013 | | |
| JP | 2018515555 A | 6/2018 | | |
| JP | 2019535728 A | 12/2019 | | |
| JP | 7577655 B | 11/2024 | | |
| WO | WO 03079973 A2 | 10/2003 | | |
| WO | 2006094800 A1 | 9/2006 | | |
| WO | WO 2009023272 A1 | 2/2009 | | |
| WO | WO 2010075290 A1 | 7/2010 | | |
| WO | WO 2010075561 A1 | 7/2010 | | |
| WO | WO 2012125544 A2 | 9/2012 | | |
| WO | 2013152039 A1 | 10/2013 | | |
| WO | 2016185423 A1 | 11/2016 | | |
| WO | WO-2018092089 A1 * | 5/2018 | .............. | A61P 43/00 |
| WO | 2019008011 A1 | 1/2019 | | |
| WO | WO 2019224773 A1 | 11/2019 | | |
| WO | WO 2020103884 A1 | 5/2020 | | |

OTHER PUBLICATIONS

Patani, G.A. et al. "Bioisosterism: A Rational Approach in Drug Design" Chem. Rev. 1996, 96, 3147-3176 (Year: 1996).*

F. Meng et al., Medicinal Chemistry, China Medicine Science and Technology Press, Beijing, China, pp. 385-387 (2016).

Holler, N. et al., Fas triggers an alternative, caspase-8-independent cell death pathway using the kinase RIP as effector molecule, *Nature Immunology,* 2000, 1(6), pp. 489-495.

Degterev, A. et al., Identification of RIP1 kinase as a specific cellular target of necrostatins, *Nature Chemical Biology,* 2008, 4(5), pp. 313-321.

Dunai, Z., et al., Necroptosis: Biochemical, Physiological and Pathological Aspects, *Pathology & Oncology Research,* 2011, 17(4), pp. 791-800.

Degterev, A. et al., Chemical inhibitor of nonapoptotic cell death with therapeutic potential for ischemic brain injury, *Nature Chemical Biology,* 2005, 1(2), pp. 112-119.

(Continued)

*Primary Examiner* — Andrew S Rosenthal

(74) *Attorney, Agent, or Firm* — FINNEGAN, HENDERSON, FARABOW, GARRETT & DUNNER LLP

(57) ABSTRACT

The present disclosure provides compounds including piperazine heterocyclic amide urea compounds that inhibit cellular necrosis and/or human receptor interacting protein 1 kinase (RIP1), including corresponding sulfonamides, and pharmaceutically acceptable salts, hydrates and stereoisomers thereof. The compounds are employed in pharmaceutical compositions, and methods of making and use, including treating a person in need thereof with an effective amount of the compound or composition, and detecting a resultant improvement in the person's health or condition.

25 Claims, No Drawings

(56) References Cited

OTHER PUBLICATIONS

Manguso, R. T. et al., In vivo CRISPR screening identifies Ptpn2 as a cancer immunotherapy target, *Nature,* 2017, 547(7664), pp. 413-418.

Wang, W. et al., RIP1 Kinase Drives Macrophage-Mediated Adaptive Immune Tolerance in Pancreatic Cancer, *Cancer Cell,* 2018, 34(5), pp. 757-774.

Berge, S. M., et al., Pharmaceutical Salts, *Journal of Pharmaceutical Sciences,* 1977, 66(1), pp. 1-19.

International Search Report and Written Opinion in counterpart PCT application No. PCT/CN2021/094986, mailed Aug. 25, 2021.

* cited by examiner

RECEPTOR-INTERACTING PROTEIN 1 INHIBITORS INCLUDING PIPERAZINE HETEROCYCLIC AMIDE UREAS

CROSS-REFERENCE TO RELATED APPLICATIONS

This is a national stage application of International Application No. PCT/CN2021/094986, filed May 20, 2021, which claims priority to PCT/CN2020/091429, filed May 20, 2020, all of which are incorporated herein by reference.

INTRODUCTION

Tumor necrosis factor alpha (TNF-α)-induced NF-κB activation plays a central role in the immune system and inflammatory responses. Receptor-interacting protein 1 (RIP1) is a multi-functional signal transducer involved in mediating nuclear factor κB (NF-κB) activation, apoptosis, and necroptosis. The kinase activity of RIP1 is critically involved in mediating necroptosis, a caspase-independent pathway of necrotic cell death. Holler et al. Nat Immunol 2000; 1: 489-495; Degterev et al. Nat Chem Biol 2008; 4: 313-321.

Necroptosis plays a role in various pathological forms of cell death, including ischemic brain injury, neurodegenerative diseases and viral infections. Dunai, et al., December 2011, Pathol. Oncol. Res.: POR 17 (4): 791-800. Necrostatin-1 (Nec-1), a small molecule inhibitor of RIP1 kinase activity, can block necroptosis. Degterev et al. Nat Chem Biol 2005; 1: 112-119.

RIP1 can contribute to D-1 immunotherapy resistance (e.g. Manguso et al., 2017 Nature 547, 413-418) and can act as a checkpoint kinase governing tumor immunity (e.g. Wang et al, Cancer Cell 34, 757-774, Nov. 12, 2018).

Related patent publications include: U.S. Pat. No. 9,974,762, U.S. Ser. No. 10/092,529, U.S. Pat. Nos. 6,756,394, 8,278,344, US20120122889, US20090099242, US20100317701, US20110144169, US20030083386, US201200309795, WO2009023272, WO2010075290, WO2010075561, WO2012125544, and WO 2020/103884.

SUMMARY OF THE INVENTION

The invention provides compounds that are inhibitors of necrosis, necroptosis, ferroptosis, human receptor interacting protein 1 kinase (RIP1) or related indications, and prodrugs thereof, which are hydrolyzed, typically in the gut or blood, to yield the corresponding inhibitors. In embodiments the inhibitors provide unexpectedly exceptional metabolic stability, evidenced by liver microsome data and PK data.

In an aspect the invention provides a compound of formula Ia:

Ia

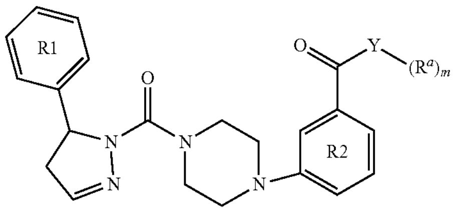

R1 is C6 aryl comprising 0 or 1 N heteroatom, optionally substituted at C3 and/or C5 with halogen or CN;

R2 is C6 aryl comprising 0, 1 or 2 N heteroatoms, optionally substituted at C4 with halogen or C1 to C3 alkoxy;

Y is O or N;

when Y is N, m is 2, and

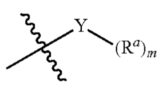 is 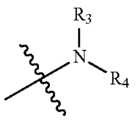

when Y is O, m is 1, and

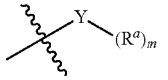 is 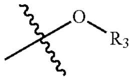

R3 and R4 are independently H or alkyl or cycloalkyl or —$OR^s$, for example, H or C1-C6 alkyl or cycloalkyl or —$OR^s$, e.g. H or C1-C3 alkyl or C3-C6 cycloalkyl or —$OR^s$, wherein $R^s$ is C1-C6 alkyl optionally substituted with halogen and C3-C6 cycloalkyl; wherein the alkyl and cycloalkyl, or the C1-C6 alkyl and cycloalkyl, or the C1-C3 alkyl and C3-C6 cycloalkyl are each independently substituted with 0-3 substituents selected from halide, optionally-substituted N, S or O, and optionally-substituted hydrocarbyl, wherein R3 and R4 may be joined in a heterocycle;

or a salt, hydrate or stereoisomer thereof.

In an aspect the invention provides a compound of formula I:

I

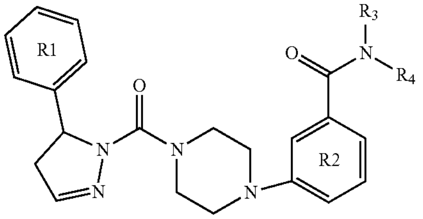

R1 is C6 aryl comprising 0 or 1 N heteroatom, optionally substituted at C3 and/or C5 with F or CN;

R2 is C6 aryl comprising 0, 1 or 2 N heteroatoms, optionally substituted at C4 with F;

R3 and R4 are independently H or C1-C3 alkyl substituted with 0-3 substituents selected from halide, optionally-substituted N, S or O, and optionally-substituted hydrocarbyl, wherein R3 and R4 may be joined in a heterocycle;

or a salt, hydrate or stereoisomer thereof.

In embodiments:

the R3 and R4 substituents are independently C0-C6: aldehyde, aldimine, alkanoyloxy, alkoxy, alkoxycarbonyl, alkyloxy, alkyl, alkenyl, alkynyl, amine, azo, halogens, carbamoyl, carbonyl, carboxamido, carboxyl, cyanyl, ester, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3);

R2 comprises N2, N4 or N2/N4; or any combination of the foregoing substituents.

In an aspect the invention provides a compound having a structure disclosed herein.

In an aspect the invention provides a pharmaceutical composition comprising a therapeutically effective amount of a compound, a salt, hydrate or stereoisomer thereof, disclosed herein and one or more pharmaceutically acceptable excipients, in predetermined, unit dosage form.

In an aspect the invention provides use of a compound, a salt, hydrate or stereoisomer thereof, or composition disclosed herein in the manufacture of a medicament for inhibiting necrosis, necroptosis, ferroptosis, human RIP1, or related indications, in a person in need thereof.

In an aspect the invention provides a compound, a salt, hydrate or stereoisomer thereof, or composition of disclosed herein for use in inhibiting necrosis, necroptosis, ferroptosis, human RIP1, or related indications in a person in need thereof, or in the manufacture of a medicament thereof in a person in need thereof.

In an aspect the invention provides a method of using a compound, a salt, hydrate or stereoisomer thereof, or composition disclosed herein for inhibiting necrosis, necroptosis, ferroptosis, human RIP1, or related indications in a person in need thereof, or in the manufacture of a medicament thereof in a person in need thereof.

The invention encompasses all combination of the particular embodiments recited herein, as if each combination had been laboriously recited.

DESCRIPTION OF PARTICULAR EMBODIMENTS OF THE INVENTION

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The term "alkyl" refers to a hydrocarbon group selected from linear and branched saturated hydrocarbon groups of 1-18, or 1-12, or 1-6, or 1-3 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

Lower alkyl means 1-8, preferably 1-6, more preferably 1-4 carbon atoms, e.g., 1-3 carbon atoms, and lower alkenyl or alkynyl means 2-8, 2-6 or 2-4 carbon atoms.

The term "alkenyl" refers to a hydrocarbon group selected from linear and branched hydrocarbon groups comprising at least one C═C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkylene" refers to a hydrocarbon group selected from linear and branched hydrocarbon groups comprising an ═C double bond and of 1-18, or 1-12, or 1-6, or 1-3 carbon atoms, wherein the point of attachment is at the ═C group of the alkylene. For example, in

, the cyclobutene is substituted with a C1 alkylene, i.e., a methylene group.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6, or 3-4, or 5-6 carbon atoms. Even further for example, the cycloalkyl group may be a monocyclic group of 3-12, or 3-8, or 3-6, or 5-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halogen" or "halo" refers to F, Cl, Br or I.

The term "heteroalkyl" refers to alkyl comprising at least one heteroatom.

The term "heteroaryl" refers to a group selected from:

5- to 7-membered aromatic, e.g., 5- to 6-membered aromatic, monocyclic rings comprising 1, 2, 3 or 4 heteroatoms selected from N, O, and S, with the remaining ring atoms being carbon;

8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered, e.g., 3- to 6-membered, or 3 to 5-membered, or 4 to 5-membered, or 5 to 6-membered, or 4- to 6-membered, monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1, 1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

In embodiments substituents are selected from optionally substituted heteroatom and optionally substituted, optionally hetero-, optionally cyclic C1-C18 hydrocarbyl, particularly wherein the optionally substituted, optionally hetero-, optionally cyclic C1-C18 hydrocarbyl is optionally-substituted, optionally hetero-, optionally cyclic alkyl, alkenyl or alkynyl, or optionally-substituted, optionally hetero-aryl; and/or the optionally substituted heteroatom is halogen, optionally substituted hydroxyl (such as alkoxy, aryloxy), optionally substituted acyl (such as formyl, alkanoyl, carbamoyl, carboxyl, amido), optionally substituted amino (such as amino, alkylamino, dialkylamino, amido, sulfamidyl), optionally substituted thiol (such as mercapto, alkylthiol, aryl thiol), optionally substituted sulfinyl or sulfonyl (such as alkylsulfinyl, arylsulfinyl, alkyl sulfonyl, arylsulfonyl), nitro, or cyano.

In embodiments, substituents are selected from: halogen, —R', —OR', =O, =NR', =N—OR', —NR'R", —SR', —SiR'R"R'", —OC(O)R', —C(O)R', —CO2R', —CONR'R", —OC(O)NR'R", —NR"C(O)R', —NR'—C(O)NR"R'", —NR'—SO2NR'", —NR"CO2R', —NH—C(NH2)=NH, —NR'C(NH2)=NH, —NH—C(NH2)=NR', —S(O)R', —SO2R', —SO2NR'R", —NR"SO2R, —CN and —NO2, —N3, —CH(Ph)2, perfluoro(C1-C4)alkoxy and perfluoro(C1-C4)alkyl, in a number ranging from zero to three, with those groups having zero, one or two substituents being particularly preferred. R', R" and R'" each independently refer to hydrogen, unsubstituted (C1-C8)alkyl and heteroalkyl, (C1-C8)alkyl and heteroalkyl substituted with one to three halogens, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. Hence, —NR'R" includes 1-pyrrolidinyl and 4-morpholinyl, "alkyl" includes groups such as trihaloalkyl (e.g., —CF3 and —CH2CF3), and when the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl".

Preferred substituents are selected from: halogen, —R', —OR', =O, —NR'R", —SR', —SiR'R"R'", —OC(O)R', —C(O)R', —CO2R', —CONR'R", —OC(O)NR'R", —NR"C(O)R', —NR"CO2R', —NR'—SO2NR"R'", —S(O)R', —SO2R', —SO2NR'R", —NR"SO2R, —CN and —NO2, perfluoro(C1-C4)alkoxy and perfluoro(C1-C4)alkyl, where R' and R" are as defined above.

Preferred substituents are disclosed herein and exemplified in the tables, structures, examples, and claims, and may be applied across different compounds of the invention, i.e. substituents of any given compound may be combinatorically used with other compounds.

In particular embodiments applicable substituents are independently substituted or unsubstituted heteroatom, substituted or unsubstituted, 0-3 heteroatom C1-C6 alkyl, C1-C3 alkyl, or C1-C2 alkyl, substituted or unsubstituted, 0-3 heteroatom C2-C6 alkenyl, substituted or unsubstituted, 0-3 heteroatom C2-C6 alkynyl, or substituted or unsubstituted, 0-3 heteroatom C5-C14 aryl, C6-C14 aryl, or C5-C6 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, alkenyl, alkynyl, amine, azo, halogen, carbamoyl, carbonyl, carboxamido, carboxyl, cyanyl, ester, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3).

Combinations of substituents as disclosed herein are those that result in the formation of stable or chemically feasible compounds. For abbreviation or according to common practice, certain hydrogen atoms attached to a certain atom (e.g., a carbon atom C or a nitrogen atom N) are not specifically spelled out in a chemical structure, formula, or notation; hydrogen atoms are deemed to be present to the extent the valences of the certain atom (e.g., C or N) are completed.

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl $—CH_2C(O)—$ groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents. Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)$n-COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" refers to administering at least one compound and/or at least one stereoisomer thereof, and/or at least one hydrate thereof, and/or at least one pharmaceutically acceptable salt thereof to a subject in recognized need thereof.

An "effective amount" refers to an amount of at least one compound and/or at least one stereoisomer thereof, and/or at least one hydrate thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent $R^{16}$" herein includes from 1 to 4, such as from 1 to 3, further as 1 or 2, substituents selected from the list of $R^{16}$ as described herein.

The subject compounds and stereoisomers thereof, hydrates thereof, and pharmaceutically acceptable salts thereof may be employed alone or in combination with at least one other therapeutic agent for treatment. In some embodiments, the compounds, stereoisomers thereof, hydrates thereof, and pharmaceutically acceptable salts thereof can be used in combination with at least one additional therapeutic agent. The compound and/or one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the compound and/or one pharmaceutically acceptable salt disclosed herein.

Also provided is a composition comprising a subject compound and stereoisomers thereof, hydrates thereof, and/or pharmaceutically acceptable salts thereof, and at least one pharmaceutically acceptable carrier.

The composition comprising a subject compound and stereoisomers thereof, hydrates thereof, and/or pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The subject compounds and stereoisomers thereof, hydrates thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The subject compounds and stereoisomers thereof, hydrates thereof, and/or pharmaceutically acceptable salts thereof disclosed herein can also be administered parenterally, in sterile liquid dosage forms, such as dispersions, suspensions or solutions. Other dosages forms that can also be used to administer the subject compounds and stereoisomers thereof, hydrates thereof, and/or pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene glycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in *Remington's Pharmaceutical Sciences*, A. Osol, a standard reference text in the art.

For administration by inhalation, the subject compounds and stereoisomers thereof, hydrates thereof, and/or pharmaceutically acceptable salts thereof may be conveniently delivered in the form of an aerosol spray presentation from pressurized packs or nebulisers. The subject compounds and stereoisomers thereof, hydrates thereof, and pharmaceutically acceptable salts thereof may also be delivered as powders, which may be formulated and the powder composition may be inhaled with the aid of an insufflation powder inhaler device. One exemplary delivery system for inhalation can be metered dose inhalation (MDI) aerosol, which may be formulated as a suspension or solution of a subject compound and stereoisomers thereof, hydrates thereof, and/or pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the subject compound and stereoisomers thereof, hydrates thereof, and/or pharmaceutically acceptable salts thereof in an appropriate ophthalmic vehicle, such that the subject compound and stereoisomers thereof, hydrates thereof, and/or at least one pharmaceutically acceptable salts thereof is maintained in contact with the ocular surface for a sufficient time period to allow the compound to penetrate the corneal and internal regions of the eye.

Useful pharmaceutical dosage-forms for administration of the subject compounds and stereoisomers thereof, hydrates thereof, and/or pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the subject compound and stereoisomers thereof, hydrates thereof, and/or pharmaceutically acceptable salt thereof disclosed herein in powder, 150 milligrams of lactose, 50 milligrams of cellulose, and 6 milligrams magnesium stearate.

In some embodiments, a mixture of the compound, stereoisomers thereof, hydrates thereof, and/or pharmaceutically acceptable salts thereof and a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound, stereoisomers thereof, hydrates thereof, and/or pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound, stereoisomers thereof, hydrates thereof, and/or pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound, stereoisomers thereof, hydrates thereof, and/or pharmaceutically acceptable salts thereof are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The compounds, stereoisomers thereof, hydrates thereof, and/or pharmaceutically acceptable salt thereof disclosed herein can be administered as the sole active ingredient or in combination with at least one second active ingredient.

The subject compounds, stereoisomers thereof, hydrates thereof, and/or pharmaceutically acceptable salts are incorporated into pharmaceutical compositions or formulations. The compositions will contain pharmaceutically acceptable diluents and/or carriers, i.e. diluents or carriers that are physiologically compatible and substantially free from pathogenic impurities. Suitable excipients or carriers and methods for preparing administrable compositions are known or apparent to those skilled in the art and are described in more detail in such publications as Remington's Pharmaceutical Science, Mack Publishing Co, NJ (1991). The compositions may also be in the form of controlled release or sustained release compositions as known in the art. For many applications the subject compounds, stereoisomers thereof, hydrates thereof, and/or pharmaceutically acceptable salts are administered for morning/daytime dosing, with off period at night.

The subject compounds, stereoisomers thereof, hydrates thereof, and/or pharmaceutically acceptable salts may be used per se, or in the form of their pharmaceutically acceptable salts, such as hydrochlorides, hydrobromides, acetates, sulfates, citrates, carbonates, trifluoroacetates and the like. When compounds contain relatively acidic functionalities, salts can be obtained by addition of the desired base, either neat or in a suitable inert solvent. Examples of pharmaceutically acceptable base addition salts include sodium, potassium, calcium, ammonium, organic amino, or magnesium salts, or the like. When compounds contain relatively basic functionalities, salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al, "Pharmaceutical Salts", Journal of Pharmaceutical Science, 1977, 66, 1-19).

The neutral forms of the compounds may be regenerated by contacting the salt with a base or acid, and isolating the parent compound in the conventional manner. The parent form of the compound differs from the various salt forms in certain physical properties, such as solubility in polar solvents, but otherwise the salts are equivalent to the parent form of the compound for the purposes of this invention.

In addition to salt forms, this invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity.

Certain compounds of the invention can exist in unsolvated forms as well as solvated forms, including hydrated forms. In general, the solvated forms are equivalent to unsolvated forms and are intended to be encompassed within the scope of the present invention. Certain compounds of the invention may exist in multiple crystalline or amorphous forms. In general, all physical forms are equivalent for the uses contemplated by the present invention and are intended to be within the scope of the invention.

Some of the subject compounds, stereoisomers thereof, hydrates thereof, and/or pharmaceutically acceptable salts possess asymmetric carbon atoms (optical centers) or double bonds; the racemates, diastereomers, geometric isomers and individual isomers are all intended to be encompassed within the scope of the present invention.

The compounds of the invention may also contain unnatural proportions of atomic isotopes at one or more of the atoms that constitute such compounds, such as deuterium, e.g. —$CD_3$, $CD_2H$ or $CDH_2$ in place of methyl. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

The compounds are generally administered in a "therapeutically effective amount", i.e. the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The contacting is generally effected by administering to the subject an effective amount of one or more compounds having the general formula I (supra), including the various embodiments described above. Generally administration is adjusted to achieve a therapeutic dosage of about 0.1 to 50, preferably 0.5 to 10, more preferably 1 to 10 mg/kg, though optimal dosages are compound specific, and generally empirically determined for each compound.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the mimetic is usually a minor component (from about 0.1 to about 50% by weight or preferably from about 1 to about 40% by weight) with the remainder being various vehicles or carriers and processing aids helpful for forming the desired dosing form. Unit dosage formulations are preferably about of 5, 10, 25, 50, 100, 250, 500, or 1,000 mg per unit. In a particular embodiment, unit dosage forms are packaged in a multipack adapted for sequential use, such as blisterpack comprising sheets of at least 6, 9 or 12 unit dosage forms.

The subject compositions may also be coformulated and/or coadministered with a different compound to treat applicable indications, or to treat programmed cell death. In embodiments applicable indications include brain injury, neurodegenerative diseases, viral infections, immune tolerance, and cancer e.g. promote tumor immunity in pancreatic cancer and melanoma.

In an aspect the invention provides a compound of formula Ia:

Ia

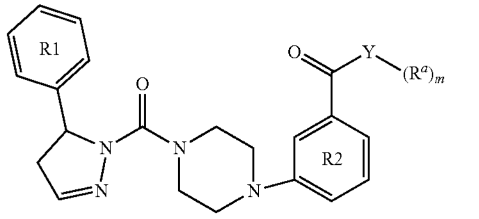

R1 is C6 aryl comprising 0 or 1 N heteroatom, optionally substituted at C3 and/or C5 with halogen or CN;

R2 is C6 aryl comprising 0, 1 or 2 N heteroatoms, optionally substituted at C4 with halogen or C1 to C3 alkoxy;

Y is O or N;

when Y is N, m is 2, and

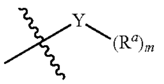 is 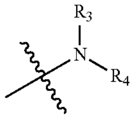

when Y is O, m is 1, and

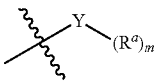 is 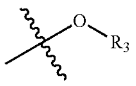

R3 and R4 are independently H or alkyl or cycloalkyl or —OR$^s$, for example, H or $C_1$-$C_6$ alkyl or cycloalkyl or —OR$^s$, e.g. H or $C_1$-$C_3$ alkyl or $C_3$-$C_6$ cycloalkyl or —OR$^s$, wherein R$^s$ is $C_1$-$C_6$ alkyl optionally substituted with halogen and $C_3$-$C_6$ cycloalkyl; wherein the alkyl and cycloalkyl, or the $C_1$-$C_6$ alkyl and cycloalkyl, or the $C_1$-$C_3$ alkyl and $C_3$-$C_6$ cycloalkyl are each independently substituted with 0-3 substituents selected from halide, optionally-substituted N, S or O, and optionally-substituted hydrocarbyl, wherein R3 and R4 may be joined in a heterocycle;

or a salt, hydrate or stereoisomer thereof.

In an aspect the invention provides a compound of formula I:

I

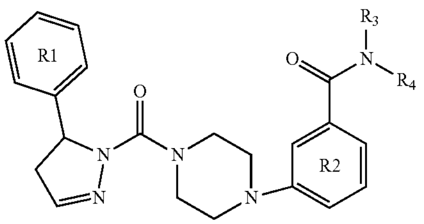

R1 is C6 aryl comprising 0 or 1 N heteroatom, optionally substituted at C3 and/or C5 with F or CN;

R2 is C6 aryl comprising 0, 1 or 2 N heteroatoms, optionally substituted at C4 with F;

R3 and R4 are independently H or C1-C3 alkyl substituted with 0-3 substituents selected from halide, optionally-substituted N, S or O, and optionally-substituted hydrocarbyl, wherein R3 and R4 may be joined in a heterocycle;

or a salt, hydrate or stereoisomer thereof.

In embodiments: the R3 and R4 substituents are independently C0-C6: aldehyde, aldimine, alkanoyloxy, alkoxy, alkoxycarbonyl, alkyloxy, alkyl, alkenyl, alkynyl, amine, azo, halogens, carbamoyl, carbonyl, carboxamido, carboxyl, cyanyl, ester, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3);

R2 comprises N2, N4 or N2/N4; or any combination of the foregoing substituents.

In one embodiment, the present disclosure provides a compound, a salt, hydrate or stereoisomer thereof, wherein the compound has the following structural formula II(1):

II(1)

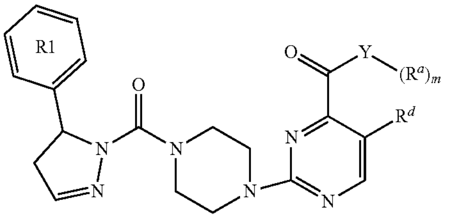

wherein Rd is selected from H, halogen, and C1 to C3 alkoxy; and all other variables not specifically defined herein are as defined in any one of the appropriate preceding embodiments.

In one embodiment, the present disclosure provides a compound, a salt, hydrate or stereoisomer thereof, wherein the compound has the following structural formula II(1)a:

II(1)a

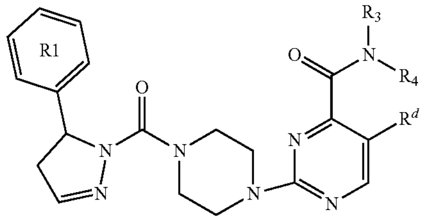

wherein R3 and R4, for each occurrence, are independently selected from: H, $C_1$-$C_3$ alkyl, $C_3$-$C_6$ cycloalkyl, and —O($C_1$-$C_3$ alkyl), wherein the $C_1$-$C_3$ alkyl and $C_3$-$C_6$ cycloalkyl are each optionally substituted with 1 to 3 groups selected from halogen, cyano, and 3- to 6-membered heterocyclyl; and all other variables not specifically defined herein are as defined in any one of the appropriate preceding embodiments.

In one embodiment, the present disclosure provides a compound, a salt, hydrate or stereoisomer thereof, wherein the compound has the following structural formula II(1)b:

II(1)b

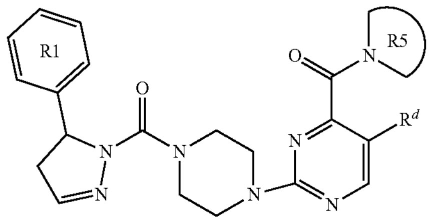

wherein R5 is optionally substituted with OH; CN; $C_3$-$C_6$ cycloalkyl; 3- to 6-membered heterocyclyl; $OR^s$; —C(═O)$NR^pR^q$; —$NR^pR^q$; $C_1$-$C_3$ alkyl, optionally substituted with CN, $C_3$-$C_6$ cycloalkyl, 3- to 6-membered heterocyclyl, or —$NR^pR^q$; or $C_1$-$C_3$ alkylene, optionally substituted with CN; wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_3$ alkyl; and all other variables not specifically defined herein are as defined in any one of the appropriate preceding embodiments.

In one embodiment, the present disclosure provides a compound, a salt, hydrate or stereoisomer thereof, wherein the compound has the following structural formula II(2):

II(2)

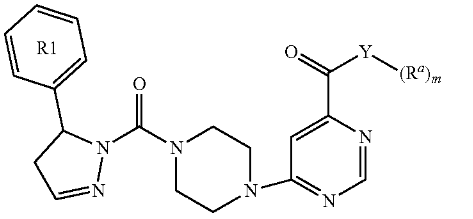

all other variables not specifically defined herein are as defined in any one of the appropriate preceding embodiments.

In one embodiment, the present disclosure provides a compound, a salt, hydrate or stereoisomer thereof, wherein the compound has the following structural formula II(2)a:

II(2)a

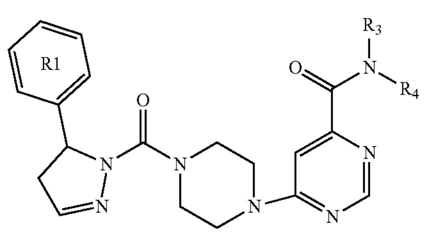

wherein R3 and R4, for each occurrence, are independently selected from: H, $C_1$-$C_3$ alkyl, $C_3$-$C_6$ cycloalkyl, and —O($C_1$-$C_3$ alkyl), wherein the $C_1$-$C_3$ alkyl and $C_3$-$C_6$ cycloalkyl are each optionally substituted with 1 to 3 groups selected from halogen, cyano, and 3- to 6-membered heterocyclyl; and all other variables not specifically defined herein are as defined in any one of the appropriate preceding embodiments.

In one embodiment, the present disclosure provides a compound, a salt, hydrate or stereoisomer thereof, wherein the compound has the following structural formula II(2)b:

II(2)b

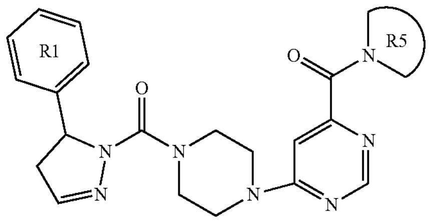

wherein R5 is optionally substituted with OH; CN; $C_3$-$C_6$ cycloalkyl; 3- to 6-membered heterocyclyl; $OR^s$; —C(═O)$NR^pR^q$; —$NR^pR^q$; $C_1$-$C_3$ alkyl, optionally substituted with CN, $C_3$-$C_6$ cycloalkyl, 3- to 6-membered heterocyclyl, or —$NR^pR^q$; or $C_1$-$C_3$ alkylene, optionally substituted with CN; wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_3$ alkyl; and all other variables not specifically defined herein are as defined in any one of the appropriate preceding embodiments.

In one embodiment, the present disclosure provides a compound, a salt, hydrate or stereoisomer thereof, wherein the compound has the following structural formula III(1):

III(1)

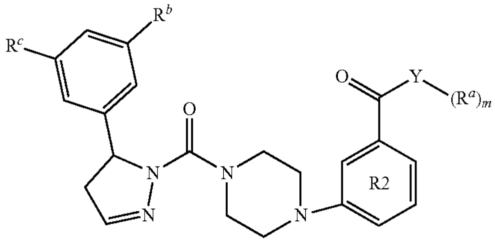

wherein R2 is C6 aryl comprising 0, 1 or 2 N heteroatoms, optionally substituted with halogen or $C_1$ to $C_3$ alkoxy, $R^b$ and $R^c$ are each independently selected from H, halogen, and CN; and all other variables not specifically defined herein are as defined in any one of the appropriate preceding embodiments.

In one embodiment, the present disclosure provides a compound, a salt, hydrate or stereoisomer thereof, wherein the compound has the following structural formula III(1)a:

III(1)a

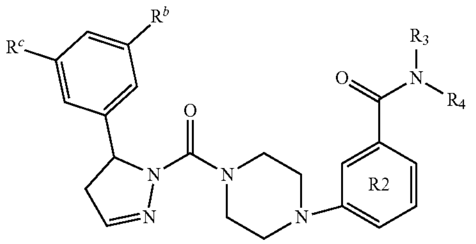

wherein R3 and R4, for each occurrence, are independently selected from: H, $C_1$-$C_3$ alkyl, $C_3$-$C_6$ cycloalkyl, and —O($C_1$-$C_3$ alkyl), wherein the $C_1$-$C_3$ alkyl and $C_3$-$C_6$ cycloalkyl are each optionally substituted with 1 to 3 groups selected from halogen, cyano, and 3- to 6-membered heterocyclyl; and all other variables not specifically defined herein are as defined in any one of the appropriate preceding embodiments.

In one embodiment, the present disclosure provides a compound, a salt, hydrate or stereoisomer thereof, wherein the compound has the following structural formula III(1)b:

III(1)b

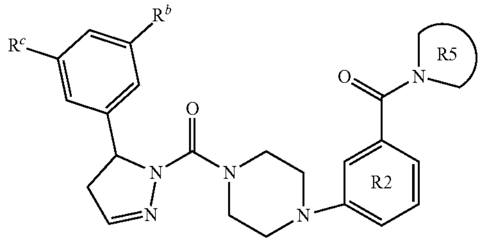

wherein R5 is optionally substituted with OH; CN; $C_3$-$C_6$ cycloalkyl; 3- to 6-membered heterocyclyl; $OR^s$; —C(═O)$NR^pR^q$; —$NR^pR^q$; $C_1$-$C_3$ alkyl, optionally substituted with CN, $C_3$-$C_6$ cycloalkyl, 3- to 6-membered heterocyclyl, or —$NR^pR^q$; or $C_1$-$C_3$ alkylene, optionally substituted with CN; wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_3$ alkyl; and all other variables not specifically defined herein are as defined in any one of the appropriate preceding embodiments.

In one embodiment, the present disclosure provides a compound, a salt, hydrate or stereoisomer thereof, wherein the compound has the following structural formula III(2):

III(2)

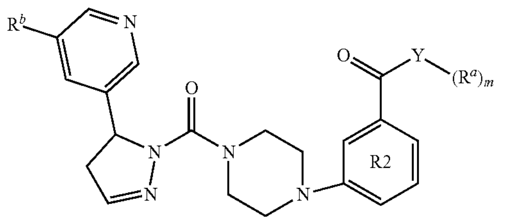

wherein R2 is C6 aryl comprising 0, 1 or 2 N heteroatoms, optionally substituted with halogen or $C_1$ to $C_3$ alkoxy, and $R^b$ is selected from H, halogen, and CN; and all other variables not specifically defined herein are as defined in any one of the appropriate preceding embodiments.

In one embodiment, the present disclosure provides a compound, a salt, hydrate or stereoisomer thereof, wherein the compound has the following structural formula III(2)a:

III(2)a

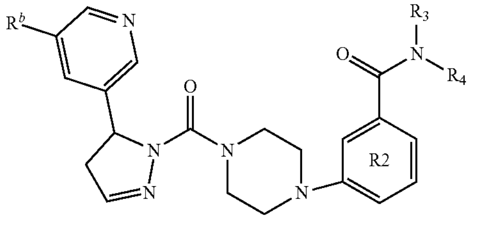

wherein R3 and R4, for each occurrence, are independently selected from: H, $C_1$-$C_3$ alkyl, $C_3$-$C_6$ cycloalkyl, and —O($C_1$-$C_3$ alkyl), wherein the $C_1$-$C_3$ alkyl and $C_3$-$C_6$ cycloalkyl are each optionally substituted with 1 to 3 groups selected from halogen, cyano, and 3- to 6-membered heterocyclyl; and all other variables not specifically defined herein are as defined in any one of the appropriate preceding embodiments.

In one embodiment, the present disclosure provides a compound, a salt, hydrate or stereoisomer thereof, wherein the compound has the following structural formula III(2)b:

III(2)b

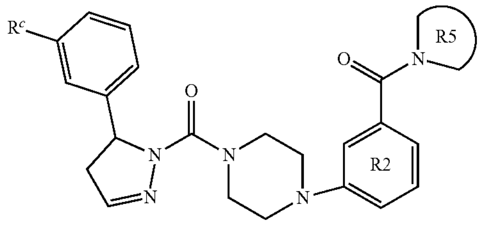

wherein R5 is optionally substituted with OH; CN; $C_3$-$C_6$ cycloalkyl; 3- to 6-membered heterocyclyl; $OR^s$; —C(═O)$NR^pR^q$; —$NR^pR^q$; $C_1$-$C_3$ alkyl, optionally substituted with CN, $C_3$-$C_6$ cycloalkyl, 3- to 6-membered heterocyclyl, or —$NR^pR^q$; or $C_1$-$C_3$ alkylene, optionally substituted with CN; wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_3$ alkyl; and all other variables not specifically defined herein are as defined in any one of the appropriate preceding embodiments.

In one embodiment, the present disclosure provides a compound, a salt, hydrate or stereoisomer thereof, wherein the compound has the following structural formula IV(1):

IV(1)

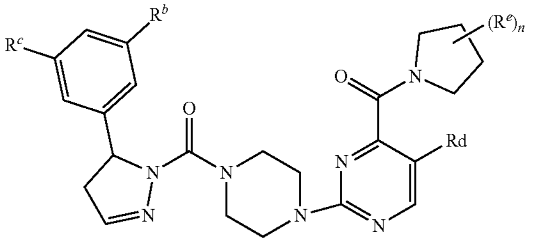

wherein $R^b$ and $R^c$ are each independently selected from H, halogen and CN; Rd is selected from H, halogen, and C1 to C3 alkoxy; and R3 and R4 join to form a 5-membered heterocyclyl substituted with n number of $R^e$, wherein $R^e$ is selected from OH; CN; $C_3$-$C_6$ cycloalkyl; 3- to 6-membered heterocyclyl; $OR^s$; —C(═O)$NR^pR^q$; —$NR^pR^q$; $C_1$-$C_3$ alkyl, optionally substituted with CN, $C_3$-$C_6$ cycloalkyl, 3- to 6-membered heterocyclyl, or —$NR^pR^q$; or $C_1$-$C_3$ alkylene, optionally substituted with CN; wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_3$ alkyl; and wherein n is 0, 1, or 2; and all other variables not specifically defined herein are as defined in any one of the appropriate preceding embodiments.

In one embodiment, the present disclosure provides a compound, a salt, hydrate or stereoisomer thereof, wherein the compound has the following structural formula IV(2):

IV(2)

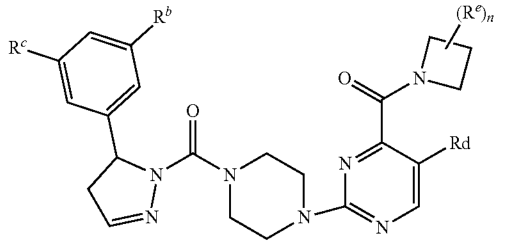

wherein $R^b$ and $R^c$ are each independently selected from H, halogen and CN; Rd is selected from H, halogen, and C1 to C3 alkoxy; and R3 and R4 join to form a 4-membered heterocyclyl substituted with n number of $R^e$, wherein $R^e$ is selected from OH; CN; $C_3$-$C_6$ cycloalkyl; 3- to 6-membered heterocyclyl; $OR^s$; —C(=O)$NR^pR^q$; —$NR^pR^q$; $C_1$-$C_3$ alkyl, optionally substituted with CN, $C_3$-$C_6$ cycloalkyl, 3- to 6-membered heterocyclyl, or —$NR^pR^q$; or $C_1$-$C_3$ alkylene, optionally substituted with CN; wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_3$ alkyl; and wherein n is 0, 1, or 2; and all other variables not specifically defined herein are as defined in any one of the appropriate preceding embodiments.

In one embodiment, the present disclosure provides a compound, a salt, hydrate or stereoisomer thereof, wherein the compound has the following structural formula IV(3):

IV(3)

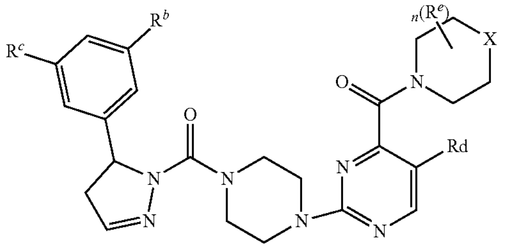

wherein $R^b$ and $R^c$ are each independently selected from H, halogen and CN; Rd is selected from H, halogen, and C1 to C3 alkoxy; X is C, N, or O; and R3 and R4 join to form a 6-membered heterocyclyl substituted with n number of $R^e$, wherein $R^e$ is selected from OH; CN; $C_3$-$C_6$ cycloalkyl; 3- to 6-membered heterocyclyl; $OR^s$; —C(=O)$NR^pR^q$; —NR-$^pR^q$; $C_1$-$C_3$ alkyl, optionally substituted with CN, $C_3$-$C_6$ cycloalkyl, 3- to 6-membered heterocyclyl, or —$NR^pR^q$; or $C_1$-$C_3$ alkylene, optionally substituted with CN; wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_3$ alkyl; and wherein n is 0, 1, or 2; and all other variables not specifically defined herein are as defined in any one of the appropriate preceding embodiments.

In one embodiment, the present disclosure provides a compound, a salt, hydrate or stereoisomer thereof, wherein the compound has the following structural formula IV(4):

IV(4)

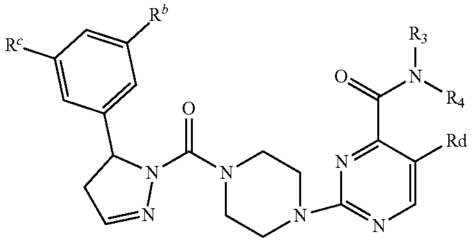

wherein $R^b$ and $R^c$ are each independently selected from H, halogen and CN; Rd is selected from H, halogen, and C1 to C3 alkoxy; and wherein R3 and R4, for each occurrence, are independently selected from: H, $C_1$-$C_3$ alkyl, $C_3$-$C_6$ cycloalkyl, and —O($C_1$-$C_3$ alkyl), wherein the $C_1$-$C_3$ alkyl and $C_3$-$C_6$ cycloalkyl are each optionally substituted with 1 to 3 groups selected from halogen, cyano and 3- to 6-membered heterocyclyl; and all other variables not specifically defined herein are as defined in any one of the appropriate preceding embodiments.

In one embodiment, the present disclosure provides a compound, a salt, hydrate or stereoisomer thereof, wherein R3 and R4, for each occurrence, are independently selected from: H; $C_1$-$C_6$ alkyl; and $C_3$-$C_6$ cycloalkyl; and —$OR^s$; wherein the $C_1$-$C_6$ alkyl and $C_3$-$C_6$ cycloalkyl of R3 and R4 are each optionally substituted with 1 to 3 groups selected from halogen, cyano and 3- to 6-membered heterocyclyl; or R3 and R4 join to form a 4-6 membered heterocyclyl optionally substituted with OH; CN; $C_3$-$C_6$ cycloalkyl; 3- to 6-membered heterocyclyl; $OR^s$; —C(=O)$NR^pR^q$; —NR-$^pR^q$; $C_1$-$C_3$ alkyl, optionally substituted with CN, $C_3$-$C_6$ cycloalkyl, 3- to 6-membered heterocyclyl, or —$NR^pR^q$; or $C_1$-$C_3$ alkylene, optionally substituted with CN; wherein $R^s$ is $C_1$-$C_6$ alkyl optionally substituted with halogen and $C_3$-$C_6$ cycloalkyl; wherein $R^p$ and $R^q$ each are independently selected from H and $C_1$-$C_6$ alkyl; and all other variables not specifically defined herein are as defined in any one of the appropriate preceding embodiments.

In one embodiment, the present disclosure provides a compound, a salt, hydrate or stereoisomer thereof, wherein R3 and R4, for each occurrence, are independently selected from: H; $C_1$-$C_3$ alkyl; and $C_3$-$C_4$ cycloalkyl; and —$OR^s$; wherein the $C_1$-$C_3$ alkyl and $C_3$-$C_4$ cycloalkyl of R3 and R4 are each optionally substituted with 1 to 3 groups selected from cyano and 3- to 6-membered heterocyclyl; or R3 and R4 join to form a 4-6 membered heterocyclyl optionally substituted with OH; CN; $C_3$-$C_6$ cycloalkyl; 3- to 6-membered heterocyclyl; $OR^s$; —C(=O)$NR^pR^q$; —NR-$^pR^q$; $C_1$-$C_3$ alkyl, optionally substituted with CN, $C_3$-$C_6$ cycloalkyl, 3- to 6-membered heterocyclyl, or —$NR^pR^q$; or $C_1$-$C_3$ alkylene, optionally substituted with CN; wherein $R^s$ is $C_1$-$C_3$ alkyl optionally substituted with halogen and $C_3$-$C_4$ cycloalkyl; and wherein $R^p$ and $R^q$ each are independently selected from H and $C_1$-$C_3$ alkyl; and all other variables not specifically defined herein are as defined in any one of the appropriate preceding embodiments.

In one embodiment, the present disclosure provides a compound, a salt, hydrate or stereoisomer thereof, wherein R3 and R4, for each occurrence, are independently selected from: H, OH, methyl, ethyl, —$CH_2CN$, —$OCH_3$,

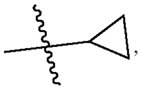, and 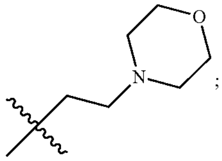;

and; and all other variables not specifically defined herein are as defined in any one of the appropriate preceding embodiments.

In one embodiment, the present disclosure provides a compound, a salt, hydrate or stereoisomer thereof, wherein R3 and R4 join to form a 4-6 membered heterocyclyl selected from

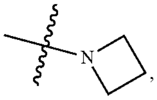,
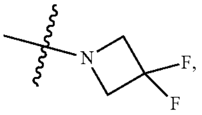,
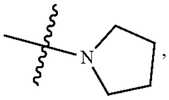,
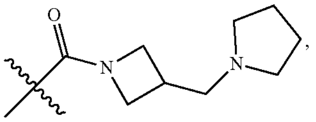,
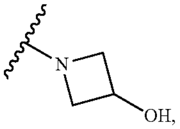,
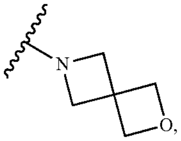,
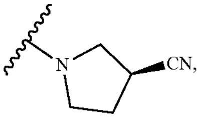,
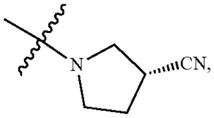,
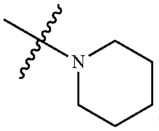,
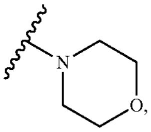,
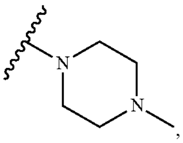,
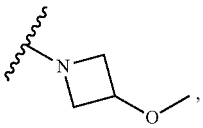,
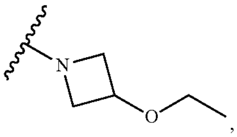,
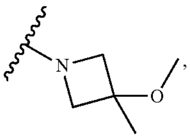,
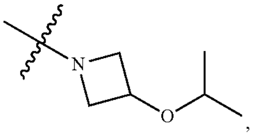,
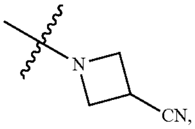,
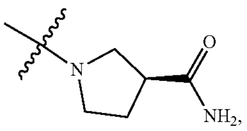,
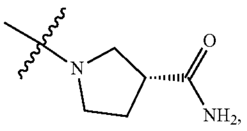, -continued

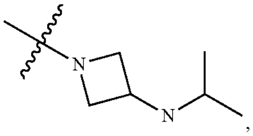,
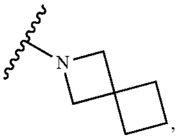,
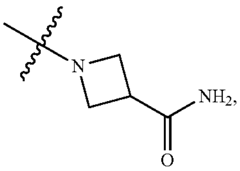,
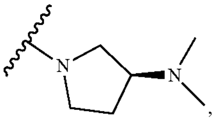,
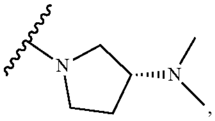,
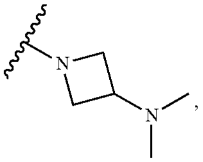,
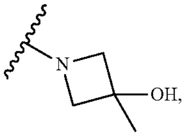,
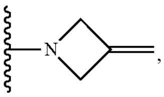,
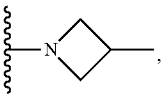,
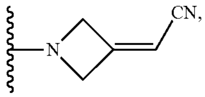,
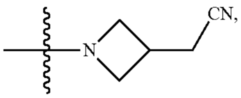,
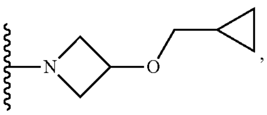,
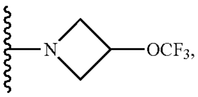, and
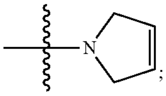;

and all other variables not specifically defined herein are as defined in any one of the appropriate preceding embodiments.

In one embodiment, the present disclosure provides a compound, a salt, hydrate or stereoisomer thereof, wherein R1 is optionally substituted with F, Cl, or CN; and R2 is optionally substituted with F, Cl, or —$OCH_3$; and all other variables not specifically defined herein are as defined in any one of the appropriate preceding embodiments.

In one embodiment, the present disclosure provides a compound, a salt, hydrate or stereoisomer thereof, wherein the compound has one of structural formulae in Table 1.

TABLE 1
| Active Compounds: Structures |
| --- |
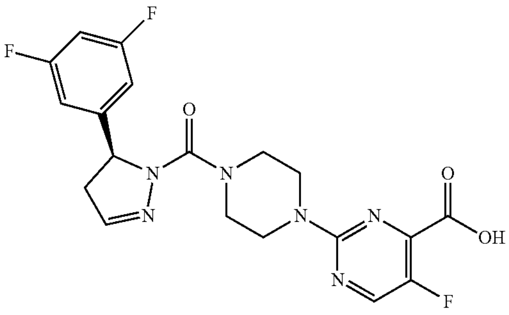 [SMILES: O=C(O)c1nc(N2CCN(C(=O)N3N=CC[C@H]3c3cc(F)cc(F)c3)CC2)ncc1F]
1
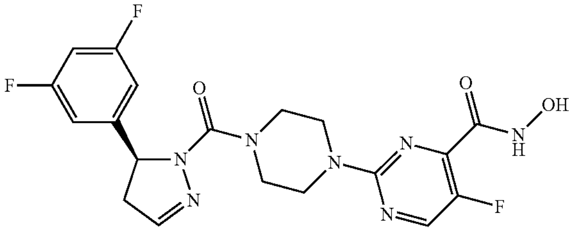 [SMILES: O=C(NO)c1nc(N2CCN(C(=O)N3N=CC[C@H]3c3cc(F)cc(F)c3)CC2)ncc1F]
2
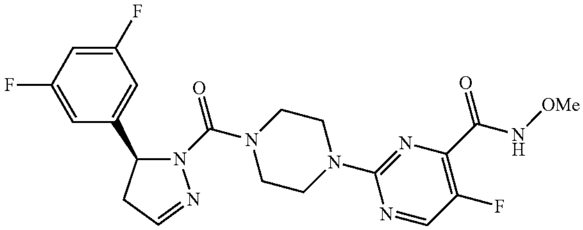 [SMILES: CONC(=O)c1nc(N2CCN(C(=O)N3N=CC[C@H]3c3cc(F)cc(F)c3)CC2)ncc1F]
3
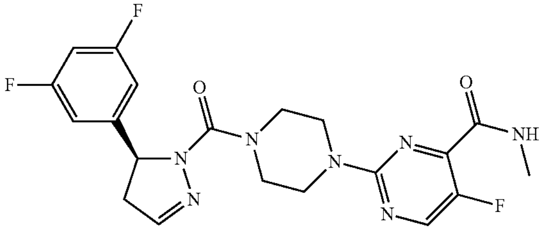 [SMILES: CNC(=O)c1nc(N2CCN(C(=O)N3N=CC[C@H]3c3cc(F)cc(F)c3)CC2)ncc1F]
4
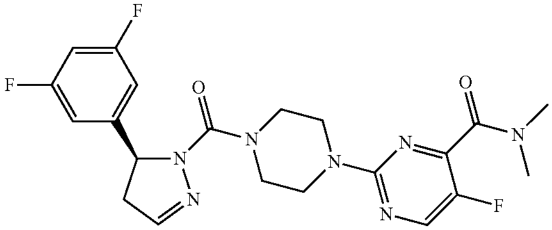 [SMILES: CN(C)C(=O)c1nc(N2CCN(C(=O)N3N=CC[C@H]3c3cc(F)cc(F)c3)CC2)ncc1F]
5
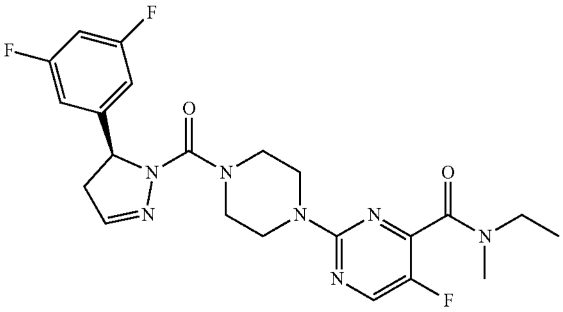 [SMILES: CCN(C)C(=O)c1nc(N2CCN(C(=O)N3N=CC[C@H]3c3cc(F)cc(F)c3)CC2)ncc1F]
6

TABLE 1-continued
| Active Compounds: Structures | |
|---|---|
| 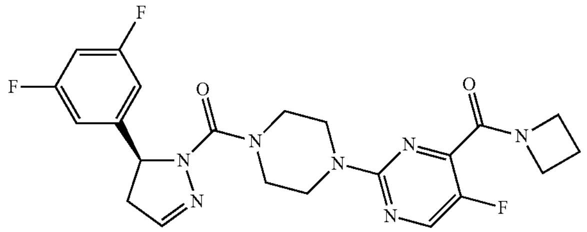 [SMILES: O=C(c1nc(N2CCN(C(=O)N3N=CC[C@H]3c3cc(F)cc(F)c3)CC2)ncc1F)N1CCC1] | 7 |
| 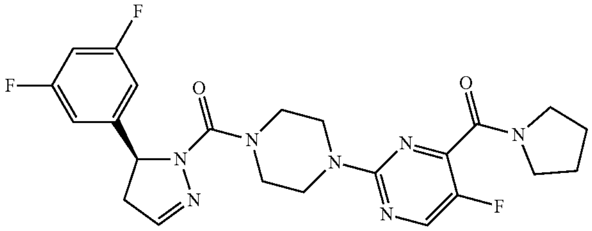 [SMILES: O=C(c1nc(N2CCN(C(=O)N3N=CC[C@H]3c3cc(F)cc(F)c3)CC2)ncc1F)N1CCCC1] | 8 |
| 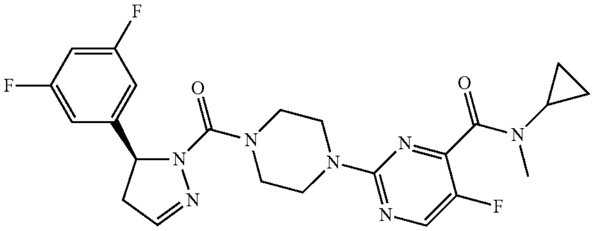 [SMILES: CN(C(=O)c1nc(N2CCN(C(=O)N3N=CC[C@H]3c3cc(F)cc(F)c3)CC2)ncc1F)C1CC1] | 9 |
| 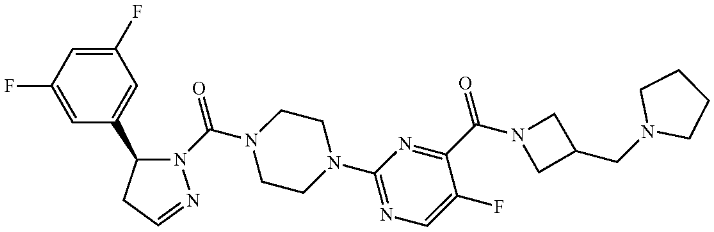 [SMILES: O=C(c1nc(N2CCN(C(=O)N3N=CC[C@H]3c3cc(F)cc(F)c3)CC2)ncc1F)N1CC(CN2CCCC2)C1] | 10 |
| 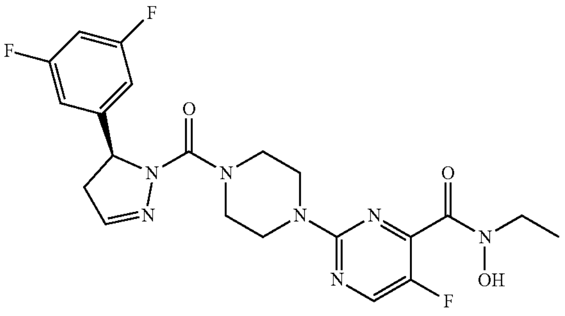 [SMILES: CCN(O)C(=O)c1nc(N2CCN(C(=O)N3N=CC[C@H]3c3cc(F)cc(F)c3)CC2)ncc1F] | 11 |
| 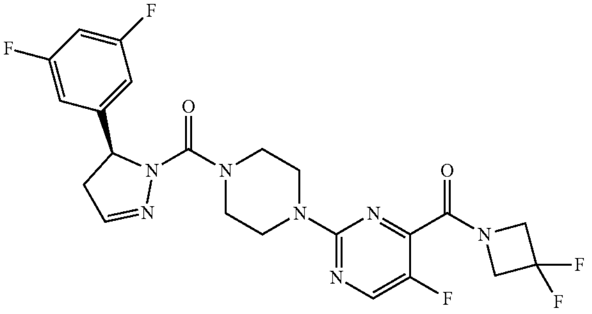 [SMILES: O=C(c1nc(N2CCN(C(=O)N3N=CC[C@H]3c3cc(F)cc(F)c3)CC2)ncc1F)N1CC(F)(F)C1] | 12 |

TABLE 1-continued
| Active Compounds: Structures |
|---|
| 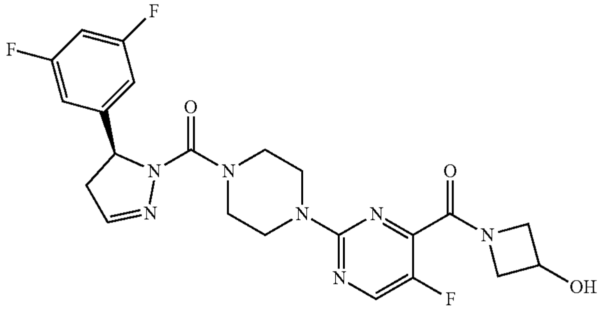 13 |
| 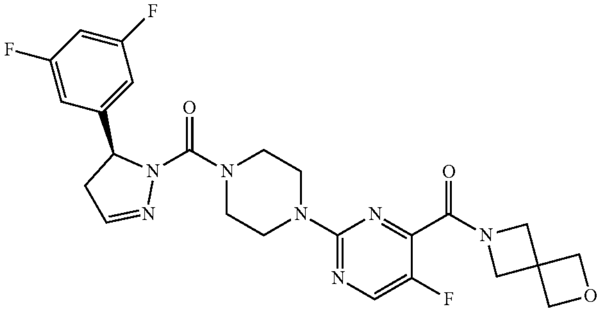 [SMILES: O=C(c1nc(N2CCN(C(=O)N3N=CC[C@H]3c3cc(F)cc(F)c3)CC2)ncc1F)N1CC2(COC2)C1] 14 |
| 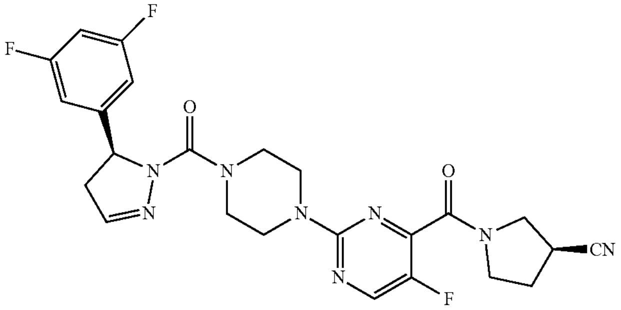 [SMILES: N#C[C@H]1CCN(C(=O)c2nc(N3CCN(C(=O)N4N=CC[C@H]4c4cc(F)cc(F)c4)CC3)ncc2F)C1] 15 |
| 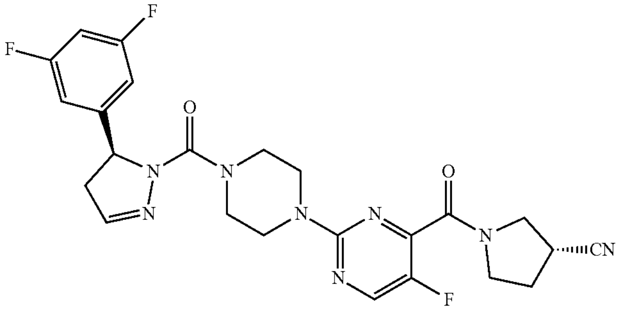 [SMILES: N#C[C@@H]1CCN(C(=O)c2nc(N3CCN(C(=O)N4N=CC[C@H]4c4cc(F)cc(F)c4)CC3)ncc2F)C1] 16 |
| 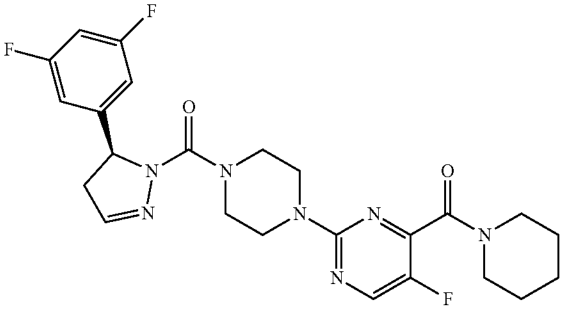 [SMILES: O=C(c1nc(N2CCN(C(=O)N3N=CC[C@H]3c3cc(F)cc(F)c3)CC2)ncc1F)N1CCCCC1] 17 |

TABLE 1-continued
| Active Compounds: Structures | |
|---|---|
| 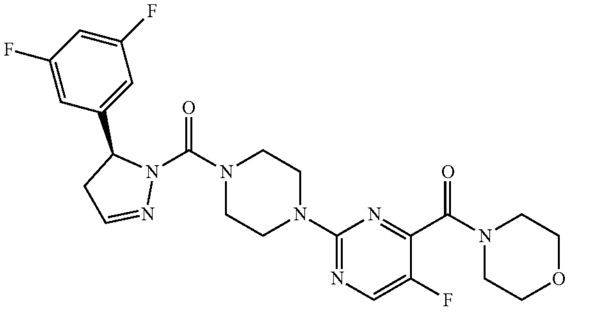 [SMILES: O=C(c1nc(N2CCN(C(=O)N3N=CC[C@H]3c3cc(F)cc(F)c3)CC2)ncc1F)N1CCOCC1] | 18 |
| 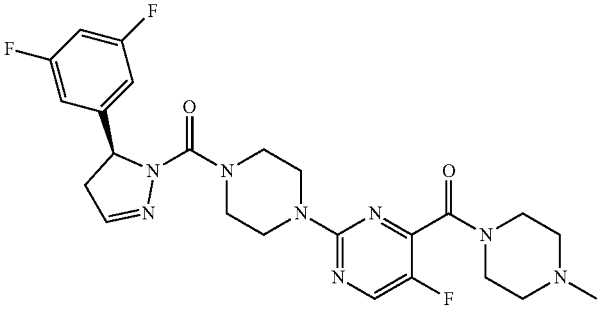 [SMILES: CN1CCN(C(=O)c2nc(N3CCN(C(=O)N4N=CC[C@H]4c4cc(F)cc(F)c4)CC3)ncc2F)CC1] | 19 |
| 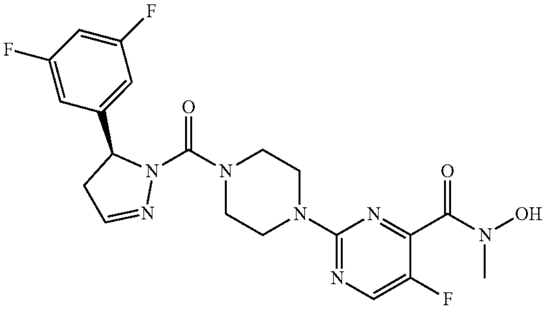 [SMILES: CN(O)C(=O)c1nc(N2CCN(C(=O)N3N=CC[C@H]3c3cc(F)cc(F)c3)CC2)ncc1F] | 20 |
| 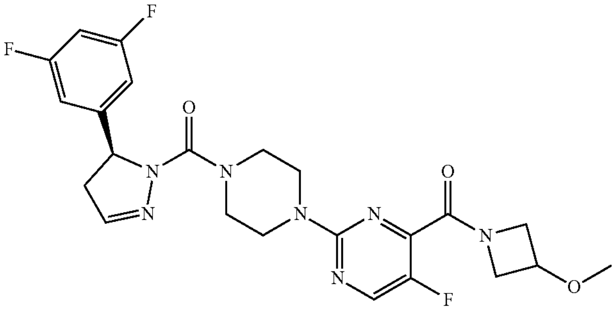 [SMILES: COC1CN(C(=O)c2nc(N3CCN(C(=O)N4N=CC[C@H]4c4cc(F)cc(F)c4)CC3)ncc2F)C1] | 21 |
| 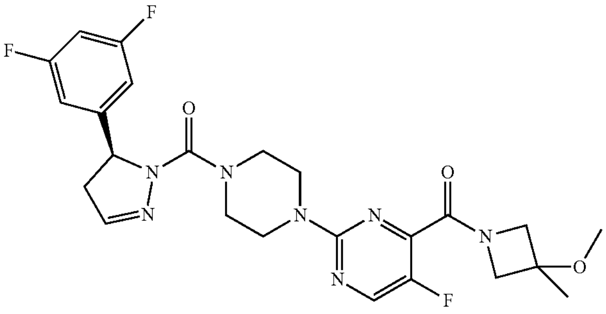 [SMILES: COC1(C)CN(C(=O)c2nc(N3CCN(C(=O)N4N=CC[C@H]4c4cc(F)cc(F)c4)CC3)ncc2F)C1] | 22 |

TABLE 1-continued
| Active Compounds: Structures |
|---|
| 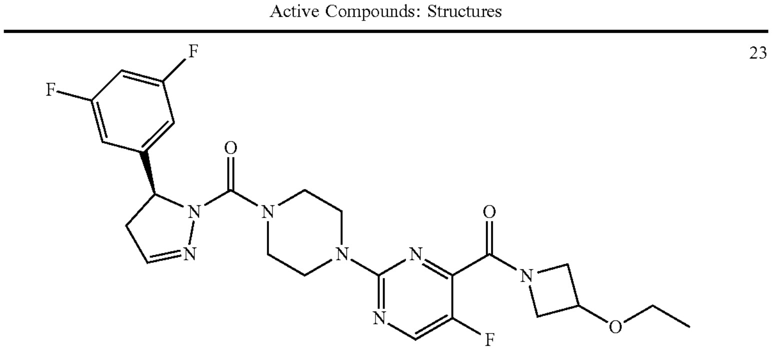 23 |
| 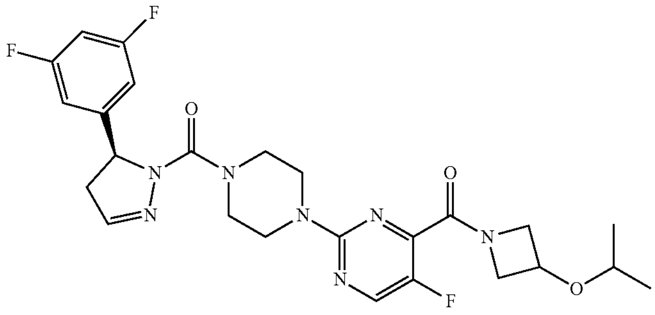 [SMILES: CC(C)OC1CN(C(=O)c2nc(N3CCN(C(=O)N4N=CC[C@H]4c4cc(F)cc(F)c4)CC3)ncc2F)C1] 24 |
| 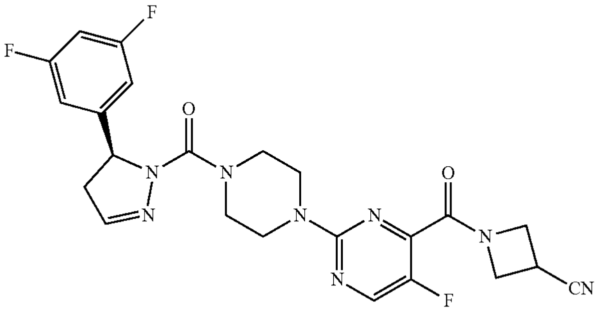 [SMILES: N#CC1CN(C(=O)c2nc(N3CCN(C(=O)N4N=CC[C@H]4c4cc(F)cc(F)c4)CC3)ncc2F)C1] 25 |
| 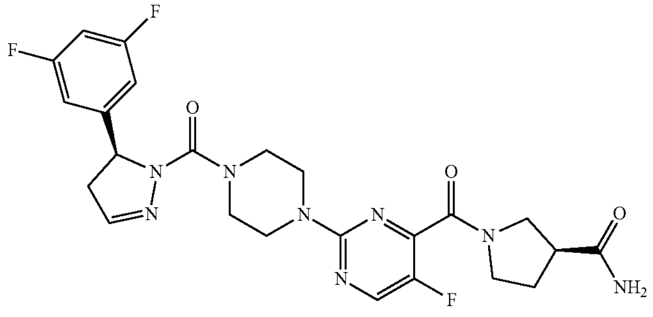 [SMILES: NC(=O)[C@H]1CCN(C(=O)c2nc(N3CCN(C(=O)N4N=CC[C@H]4c4cc(F)cc(F)c4)CC3)ncc2F)C1] 26 |
| 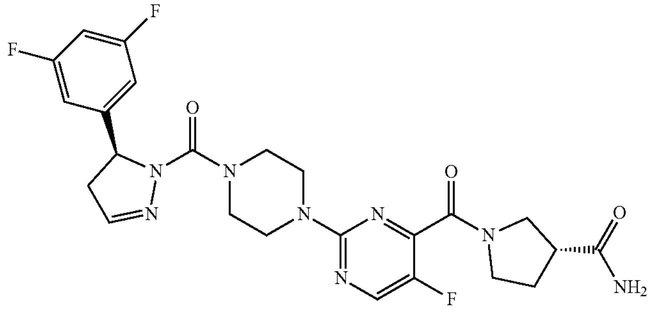 [SMILES: NC(=O)[C@@H]1CCN(C(=O)c2nc(N3CCN(C(=O)N4N=CC[C@H]4c4cc(F)cc(F)c4)CC3)ncc2F)C1] 27 |

TABLE 1-continued
| Active Compounds: Structures |
| --- |
28
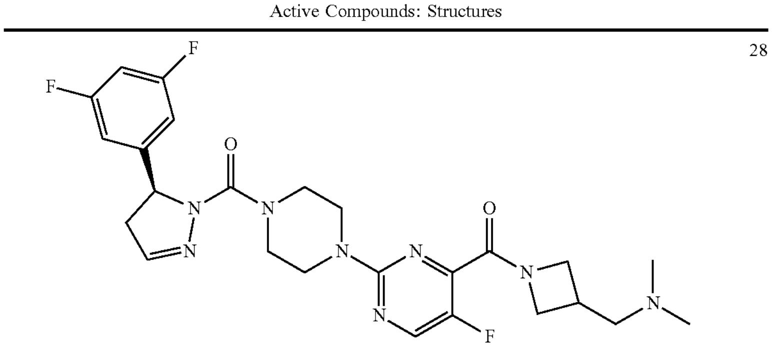
29
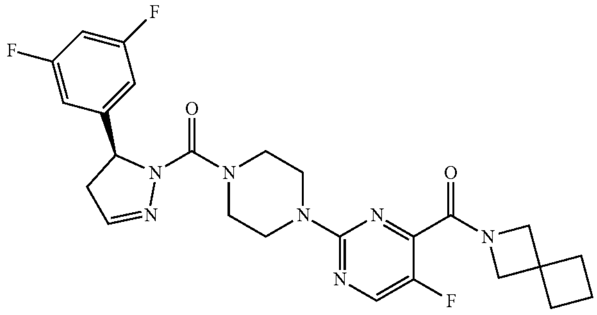 [SMILES: O=C(c1nc(N2CCN(C(=O)N3N=CC[C@H]3c3cc(F)cc(F)c3)CC2)ncc1F)N1CC2(CCC2)C1]
30
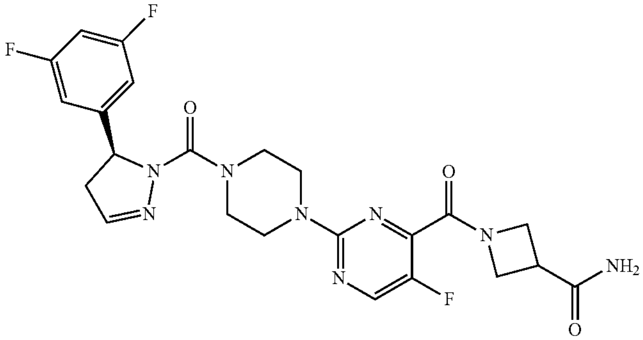 [SMILES: NC(=O)C1CN(C(=O)c2nc(N3CCN(C(=O)N4N=CC[C@H]4c4cc(F)cc(F)c4)CC3)ncc2F)C1]
31
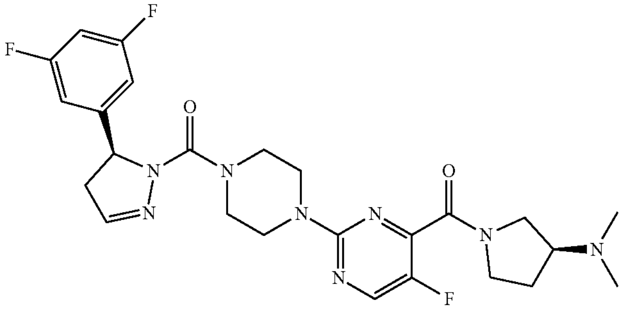 [SMILES: CN(C)[C@H]1CCN(C(=O)c2nc(N3CCN(C(=O)N4N=CC[C@H]4c4cc(F)cc(F)c4)CC3)ncc2F)C1]
32
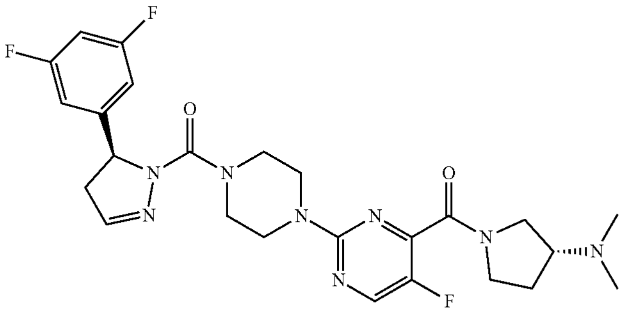 [SMILES: CN(C)[C@@H]1CCN(C(=O)c2nc(N3CCN(C(=O)N4N=CC[C@H]4c4cc(F)cc(F)c4)CC3)ncc2F)C1]

TABLE 1-continued
| Active Compounds: Structures |
| --- |
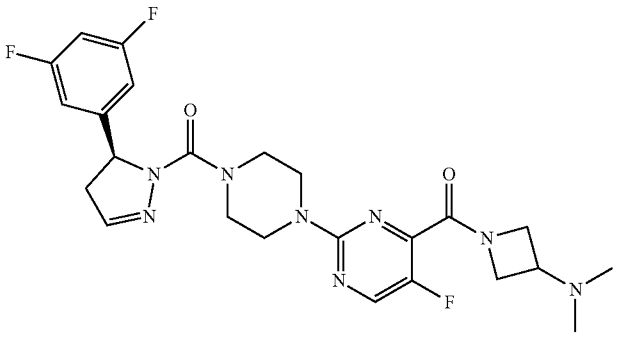 [SMILES: CN(C)C1CN(C(=O)c2nc(N3CCN(C(=O)N4N=CC[C@H]4c4cc(F)cc(F)c4)CC3)ncc2F)C1]
33
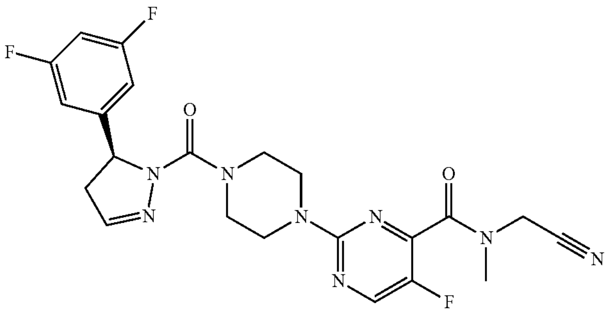 [SMILES: CN(CC#N)C(=O)c1nc(N2CCN(C(=O)N3N=CC[C@H]3c3cc(F)cc(F)c3)CC2)ncc1F]
34
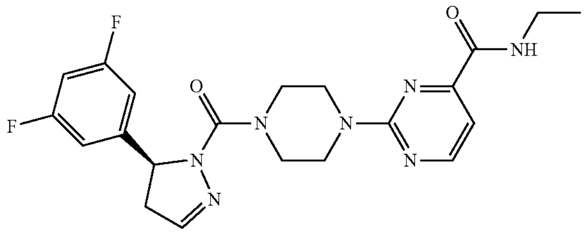 [SMILES: CCNC(=O)c1ccnc(N2CCN(C(=O)N3N=CC[C@H]3c3cc(F)cc(F)c3)CC2)n1]
35
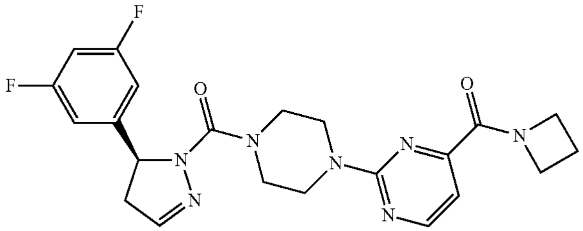 [SMILES: O=C(c1ccnc(N2CCN(C(=O)N3N=CC[C@H]3c3cc(F)cc(F)c3)CC2)n1)N1CCC1]
36
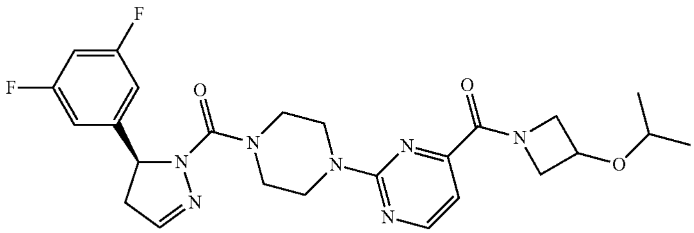 [SMILES: CC(C)OC1CN(C(=O)c2ccnc(N3CCN(C(=O)N4N=CC[C@H]4c4cc(F)cc(F)c4)CC3)n2)C1]
37

TABLE 1-continued
| Active Compounds: Structures |
|---|
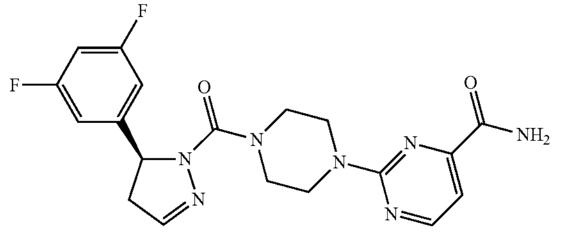 [SMILES: NC(=O)c1ccnc(N2CCN(C(=O)N3N=CC[C@H]3c3cc(F)cc(F)c3)CC2)n1]
38
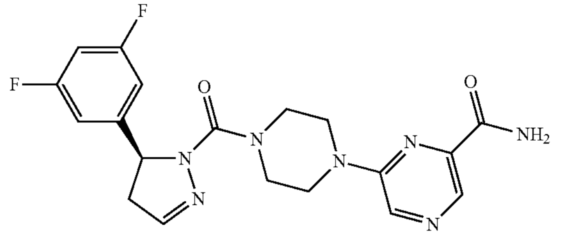 [SMILES: NC(=O)c1cncc(N2CCN(C(=O)N3N=CC[C@H]3c3cc(F)cc(F)c3)CC2)n1]
39
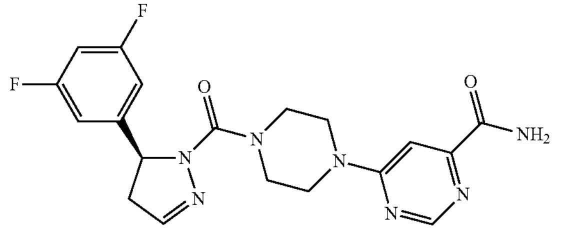 [SMILES: NC(=O)c1cc(N2CCN(C(=O)N3N=CC[C@H]3c3cc(F)cc(F)c3)CC2)ncn1]
40
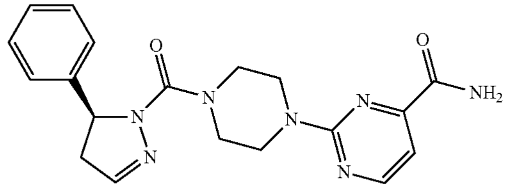 [SMILES: NC(=O)c1ccnc(N2CCN(C(=O)N3N=CC[C@H]3c3ccccc3)CC2)n1]
41
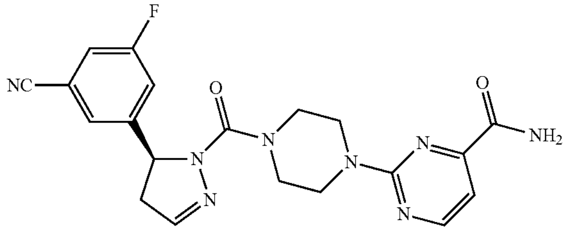 [SMILES: N#Cc1cc(F)cc([C@@H]2CC=NN2C(=O)N2CCN(c3nccc(C(N)=O)n3)CC2)c1]
42
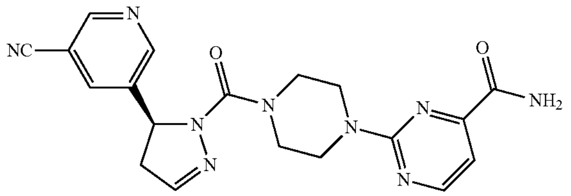 [SMILES: N#Cc1cncc([C@@H]2CC=NN2C(=O)N2CCN(c3nccc(C(N)=O)n3)CC2)c1]
43
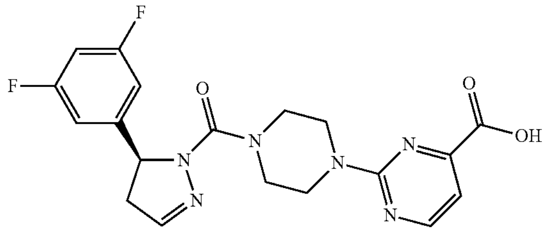 [SMILES: O=C(O)c1ccnc(N2CCN(C(=O)N3N=CC[C@H]3c3cc(F)cc(F)c3)CC2)n1]
44

TABLE 1-continued
| Active Compounds: Structures | |
|---|---|
| 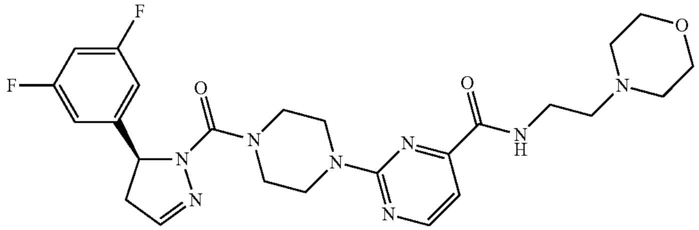 [SMILES: O=C(NCCN1CCOCC1)c1ccnc(N2CCN(C(=O)N3N=CC[C@H]3c3cc(F)cc(F)c3)CC2)n1] | 45 |
| 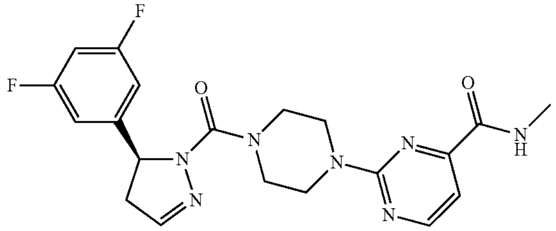 [SMILES: CNC(=O)c1ccnc(N2CCN(C(=O)N3N=CC[C@H]3c3cc(F)cc(F)c3)CC2)n1] | 46 |
| 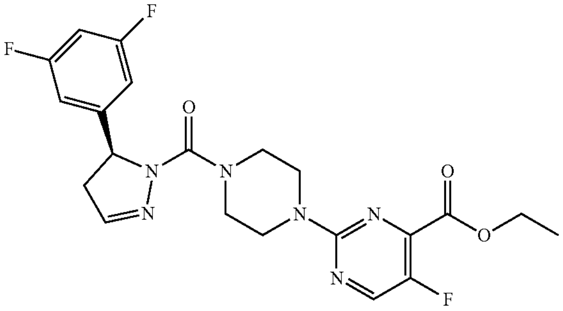 [SMILES: CCOC(=O)c1nc(N2CCN(C(=O)N3N=CC[C@H]3c3cc(F)cc(F)c3)CC2)ncc1F] | 47 |
| 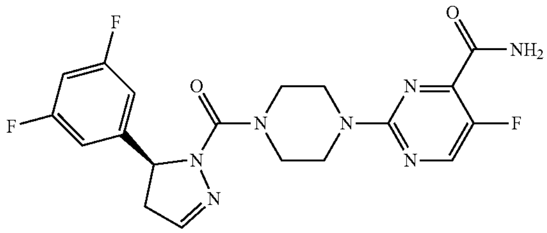 [SMILES: NC(=O)c1nc(N2CCN(C(=O)N3N=CC[C@H]3c3cc(F)cc(F)c3)CC2)ncc1F] | 48 |
| 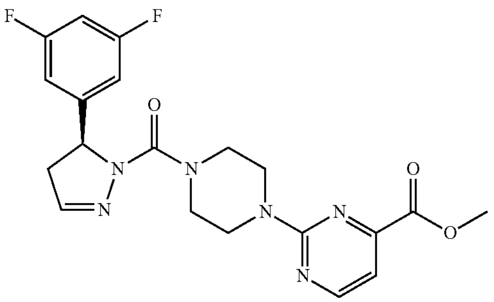 [SMILES: COC(=O)c1ccnc(N2CCN(C(=O)N3N=CC[C@H]3c3cc(F)cc(F)c3)CC2)n1] | 49 |

TABLE 1-continued
| Active Compounds: Structures |
|---|
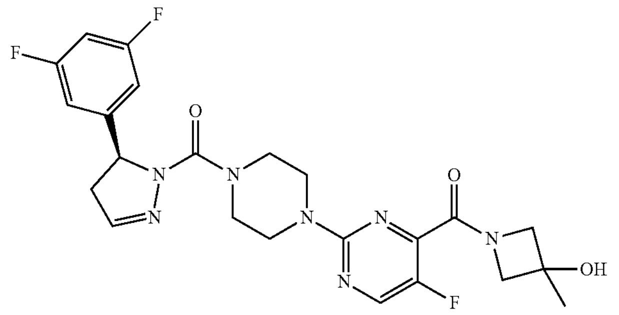 [SMILES: CC1(O)CN(C(=O)c2nc(N3CCN(C(=O)N4N=CC[C@H]4c4cc(F)cc(F)c4)CC3)ncc2F)C1]
50
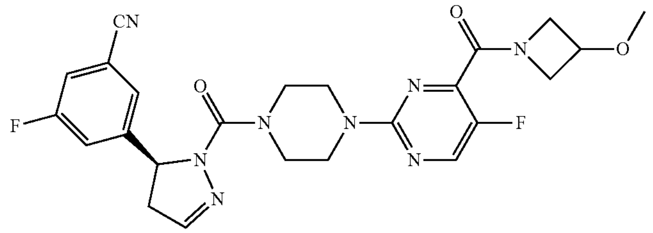 [SMILES: COC1CN(C(=O)c2nc(N3CCN(C(=O)N4N=CC[C@H]4c4cc(F)cc(C#N)c4)CC3)ncc2F)C1]
51
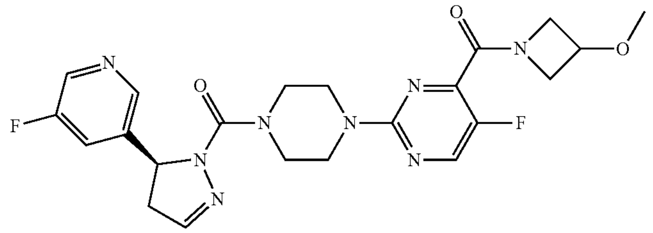 [SMILES: COC1CN(C(=O)c2nc(N3CCN(C(=O)N4N=CC[C@H]4c4cncc(F)c4)CC3)ncc2F)C1]
52
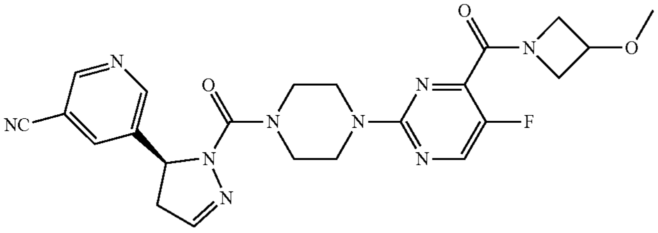 [SMILES: COC1CN(C(=O)c2nc(N3CCN(C(=O)N4N=CC[C@H]4c4cncc(C#N)c4)CC3)ncc2F)C1]
53
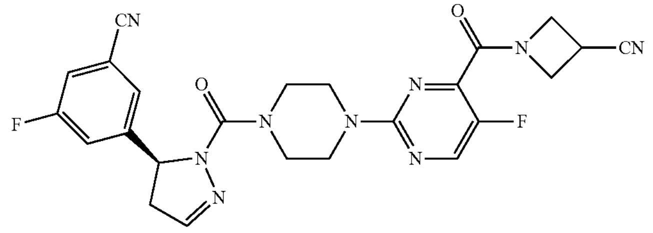 [SMILES: N#Cc1cc(F)cc([C@@H]2CC=NN2C(=O)N2CCN(c3ncc(F)c(C(=O)N4CC(C#N)C4)n3)CC2)c1]
54
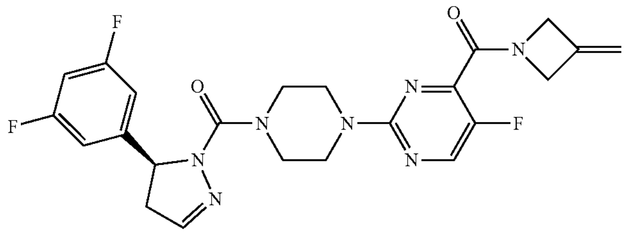 [SMILES: C=C1CN(C(=O)c2nc(N3CCN(C(=O)N4N=CC[C@H]4c4cc(F)cc(F)c4)CC3)ncc2F)C1]
55

TABLE 1-continued
| Active Compounds: Structures |
| --- |
| 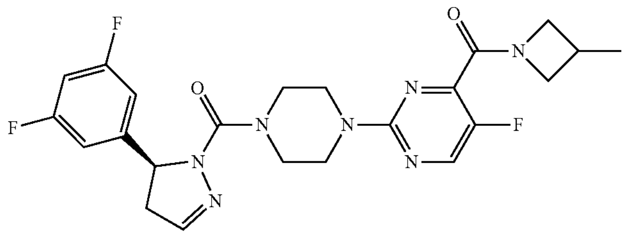 [SMILES: CC1CN(C(=O)c2nc(N3CCN(C(=O)N4N=CC[C@H]4c4cc(F)cc(F)c4)CC3)ncc2F)C1] 56 |
| 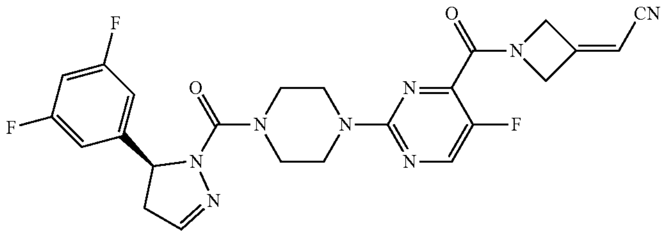 [SMILES: N#CC=C1CN(C(=O)c2nc(N3CCN(C(=O)N4N=CC[C@H]4c4cc(F)cc(F)c4)CC3)ncc2F)C1] 57 |
| 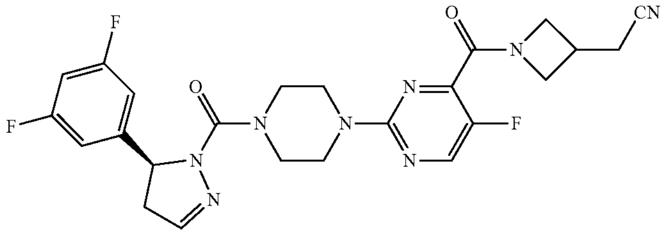 [SMILES: N#CCC1CN(C(=O)c2nc(N3CCN(C(=O)N4N=CC[C@H]4c4cc(F)cc(F)c4)CC3)ncc2F)C1] 58 |
| 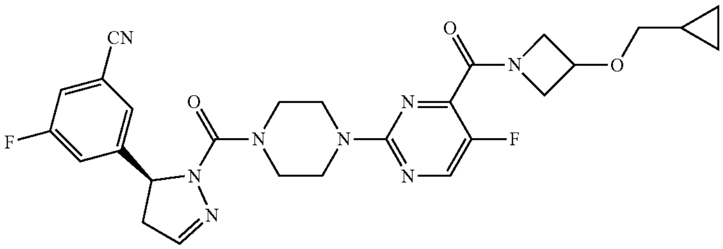 [SMILES: N#Cc1cc(F)cc([C@@H]2CC=NN2C(=O)N2CCN(c3ncc(F)c(C(=O)N4CC(OCC5CC5)C4)n3)CC2)c1] 59 |
| 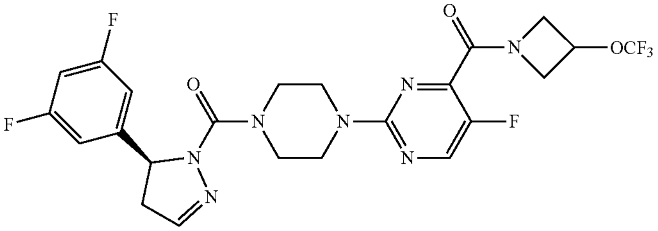 [SMILES: O=C(c1nc(N2CCN(C(=O)N3N=CC[C@H]3c3cc(F)cc(F)c3)CC2)ncc1F)N1CC(OC(F)(F)F)C1] 60 |
| 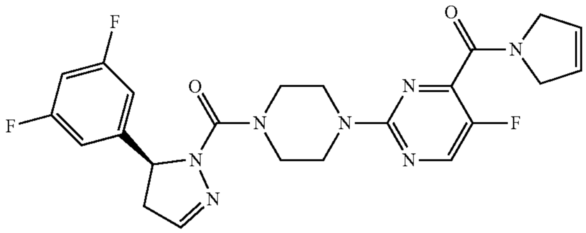 [SMILES: O=C(c1nc(N2CCN(C(=O)N3N=CC[C@H]3c3cc(F)cc(F)c3)CC2)ncc1F)N1CC=CC1] 61 |

TABLE 1-continued
| Active Compounds: Structures | |
|---|---|
| 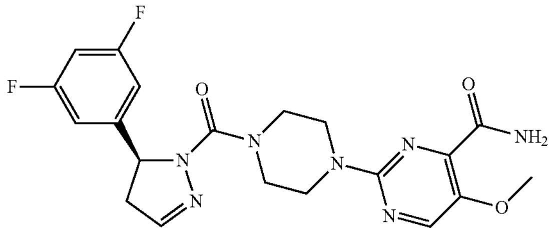 [SMILES: COc1cnc(N2CCN(C(=O)N3N=CC[C@H]3c3cc(F)cc(F)c3)CC2)nc1C(N)=O] | 62 |
| 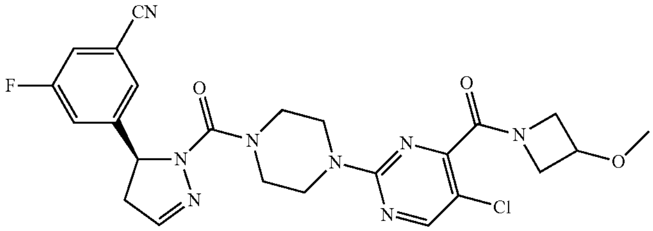 [SMILES: COC1CN(C(=O)c2nc(N3CCN(C(=O)N4N=CC[C@H]4c4cc(F)cc(C#N)c4)CC3)ncc2Cl)C1] | 63 |
| 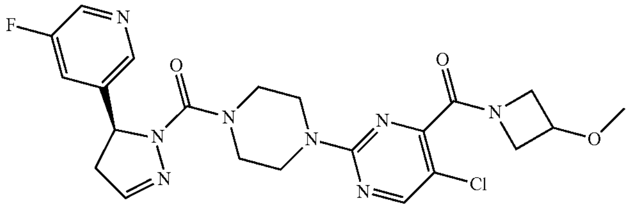 [SMILES: COC1CN(C(=O)c2nc(N3CCN(C(=O)N4N=CC[C@H]4c4cncc(F)c4)CC3)ncc2Cl)C1] | 64 |
| 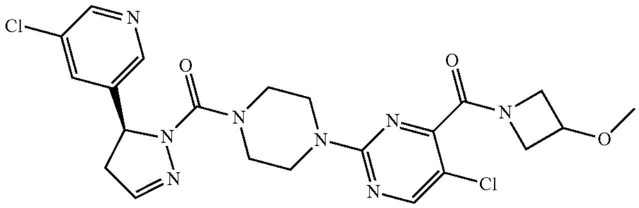 [SMILES: COC1CN(C(=O)c2nc(N3CCN(C(=O)N4N=CC[C@H]4c4cncc(Cl)c4)CC3)ncc2Cl)C1] | 65 |
| 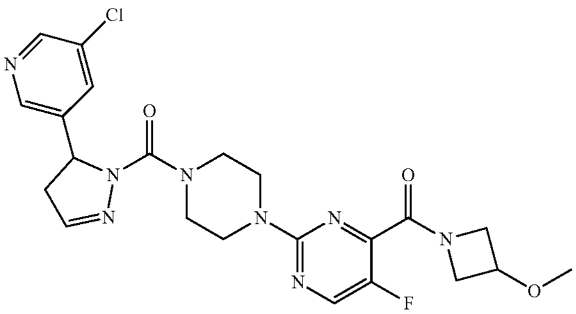 [SMILES: COC1CN(C(=O)c2nc(N3CCN(C(=O)N4N=CCC4c4cncc(Cl)c4)CC3)ncc2F)C1] | 66 |
| 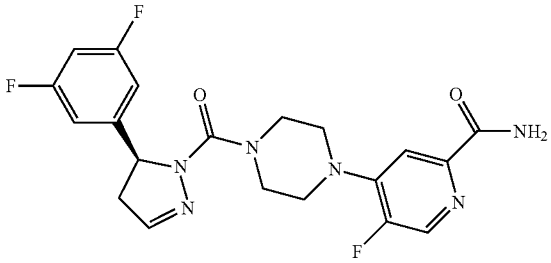 [SMILES: NC(=O)c1cc(N2CCN(C(=O)N3N=CC[C@H]3c3cc(F)cc(F)c3)CC2)c(F)cn1] | 67 |

Cellular RIP1 inhibitory activity of the test compounds 1-67 is summarized in Table 2. In Table 2, activity is provided as follows: +++=0.1 nM≤EC50<100 nM; ++=100 nM≤EC50K<1000 nM; +=1000 nM≤EC50K<10000 nM.

TABLE 2

| Cell activity; Necrosis or Necroptosis Inhibitory Activity | |
|---|---|
| # | EC50 |
| 1 | + |
| 2 | +++ |
| 3 | ++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | +++ |
| 39 | ++ |
| 40 | +++ |
| 41 | +++ |
| 42 | +++ |
| 43 | ++ |
| 44 | + |
| 45 | ++ |
| 46 | +++ |
| 47 | +++ |
| 48 | +++ |
| 49 | +++ |
| 50 | +++ |
| 51 | +++ |
| 52 | +++ |
| 53 | +++ |
| 54 | +++ |
| 55 | +++ |
| 56 | +++ |
| 57 | +++ |
| 58 | +++ |
| 59 | +++ |
| 60 | +++ |
| 61 | +++ |
| 62 | ++ |
| 63 | +++ |
| 64 | ++ |
| 65 | +++ |
| 66 | +++ |
| 67 | ++ |

Example 1

Representative Compound Synthesis

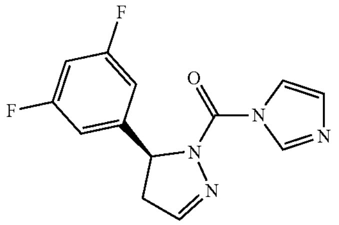

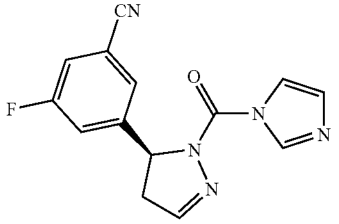

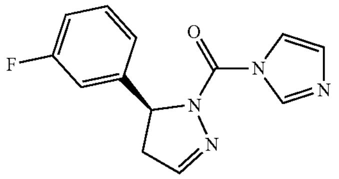

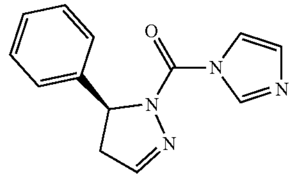

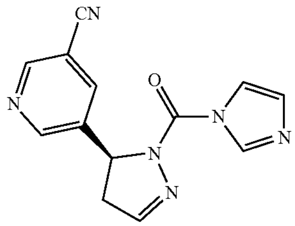

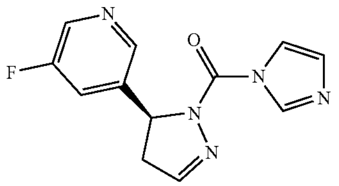

The above intermediates were synthesized and isolated as racemates. Chiral HPLC separation to yield the S-enantiomer of the intermediates, ee %>98%.

Compound 1: (S)-2-(4-(5-(3,5-difluorophenyl)-4,5-dihydro-1H-pyrazole-1-carbonyl)piperazin-1-yl)-5-fluoropyrimidine-4-carboxylic acid

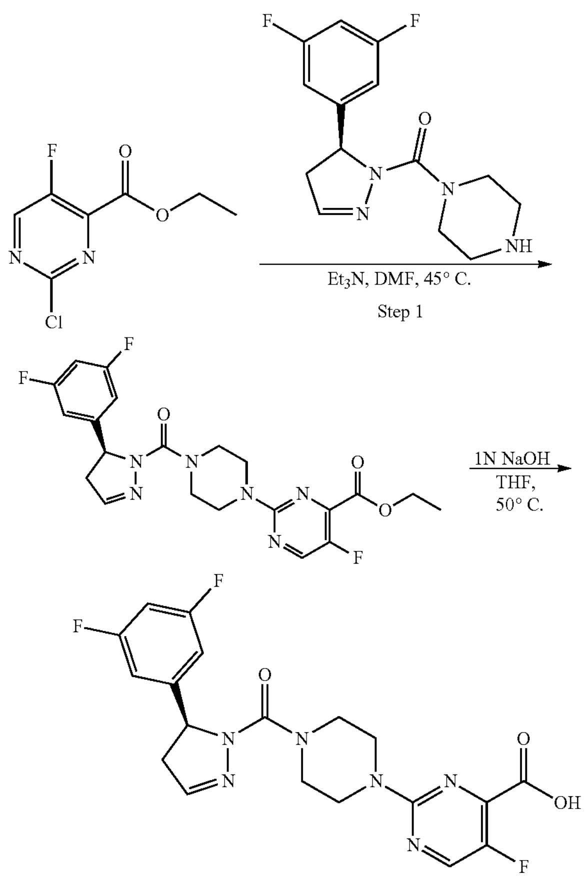

Step 1: To a solution of ethyl 2-chloro-5-fluoropyrimidine-4-carboxylate (3.5 g, 17.0 mmol) in DMF (0 mL) was added (5-(3,5-difluorophenyl)-4,5-dihydro-1H-pyrazol-1-yl)(piperazin-1-yl)methanone (5 g, 17.0 mmol) and TEA (3.44 g, 34.0 mmol). The reaction was stirred at 45° C. for 4 h. The mixture purified by flash column chromatography (EtOAc/PE=0% to 10%). 2.2 g ethyl 2-(4-(5-(3,5-difluorophenyl)-4,5-dihydro-1H-pyrazole-1-carbonyl)piperazin-1-yl)-5-fluoropyrimidine-4-carboxylate was obtained as a yellow solid. Yield: 27.8%. LC-MS (m/z) 463.1 (M+H$^+$).

Step 2: To a solution of ethyl 2-(4-(5-(3,5-difluorophenyl)-4,5-dihydro-1H-pyrazole-1-carbonyl)piperazin-1-yl)-5-fluoropyrimidine-4-carboxylate (2.1 g,) in THF (25 mL) was added 1 N NaOH (25 mL). The reaction mixture was stirred at 50° C. for 2 h. 1.7 g of (S)-2-(4-(5-(3,5-difluorophenyl)-4,5-dihydro-1H-pyrazole-1-carbonyl)piperazin-1-yl)-5-fluoropyrimidine-4-carboxylic acid was obtained as a yellow solid. Yield: 86.2%. LC-MS (m/z) 435.3 (M+H$^+$). $^1$H NMR (400 MHz, $CDCl_3$) δ (ppm): 8.12 (d, J=2.2 Hz, 1H), 6.65 (t, J=1.7 Hz, 1H), 6.62-6.56 (m, 2H), 6.45 (tt, J=8.9, 2.3 Hz, 1H), 5.07 (dd, J=11.7, 9.9 Hz, 1H), 3.70-3.60 (m, 2H), 3.59-3.45 (m, 4H), 3.43-3.32 (m, 2H), 3.14-3.06 (m, 1H), 2.49-2.41 (m, 1H).

Compound 2: (S)-2-(4-(5-(3,5-difluorophenyl)-4,5-dihydro-1H-pyrazole-1-carbonyl)piperazin-1-yl)-5-fluoro-N-hydroxypyrimidine-4-carboxamide

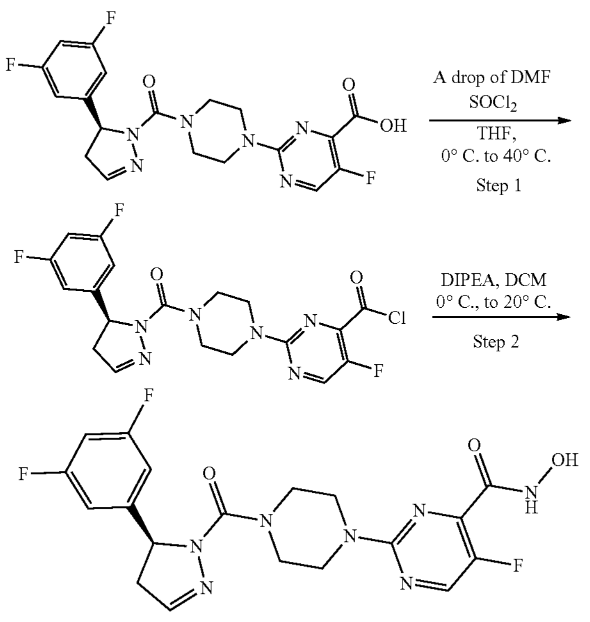

Step 1: To a solution of 2-(4-(5-(3,5-difluorophenyl)-4,5-dihydro-1H-pyrazole-1-carbonyl)piperazin-1-yl)-5-fluoropyrimidine-4-carboxylic acid (600 mg, 1.38 mmol) in THF (20 mL) was added a drop of DMF and $SOCl_2$ (822 mg, 6.91 mmol). The reaction was stirred at 0° C. to 40° C. for 1 h. The solvent was removed under vacuum and the crude product was used to next step directly.

Step 2: To a solution of 2-(4-(5-(3,5-difluorophenyl)-4,5-dihydro-1H-pyrazole-1-carbonyl)piperazin-1-yl)-5-fluoropyrimidine-4-carbonyl chloride (100 mg, 220.8 umol) in DCM (5 mL) was added DIPEA (5 mL) and Hydroxylamine hydrochloride (31 mg, 441.7 umol) at 0° C. under Ar. The reaction mixture was stirred at 20° C. for 1 h. The mixture was purified by reversed-phase chromatography. 36 mg of (S)-2-(4-(5-(3,5-difluorophenyl)-4,5-dihydro-1H-pyrazole-1-carbonyl)piperazin-1-yl)-5-fluoro-N-hydroxypyrimidine-4-carboxamide was obtained as a light yellow solid. Yield: 36.3%. LC-MS (m/z) 450.1 (M+H$^+$). $^1$H NMR (400 MHz, DMSO-$d_6$) δ (ppm): 11.35 (s, 1H), 9.34 (brs, 1H), 8.58 (d, J=2.4 Hz, 1H), 7.14-7.06 (m, 2H), 7.02-6.94 (m, 2H), 5.24 (dd, J=11.6, 9.9 Hz, 1H), 3.84-3.45 (m, 8H), 3.35 (ddd, J=18.3, 11.7, 1.9 Hz, 1H), 2.63 (ddd, J=18.3, 10.0, 1.6 Hz, 1H).

Compound 3: (S)-2-(4-(5-(3,5-difluorophenyl)-4,5-dihydro-1H-pyrazole-1-carbonyl)piperazin-1-yl)-5-fluoro-N-methoxypyrimidine-4-carboxamide

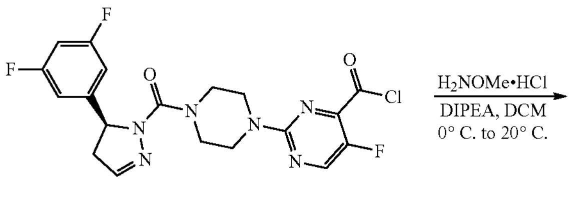

-continued

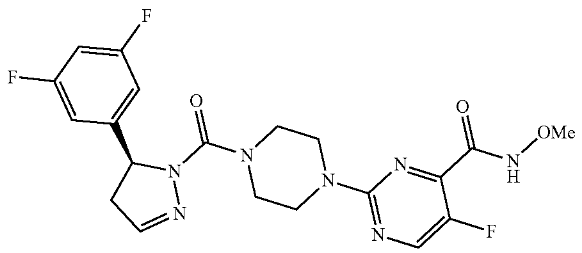

The titled compound 3 was prepared in 62.1% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 464.1 ($M+H^+$). $^1H$ NMR (400 MHz, DMSO-$d_6$) δ (ppm): 11.83 (s, 1H), 8.56 (d, J=2.3 Hz, 1H), 7.14-7.05 (m, 2H), 7.02-6.94 (m, 2H), 5.24 (dd, J=11.6, 9.9 Hz, 1H), 3.86-3.45 (m, 11H), 3.35 ddd, J=18.3, 9.9, 1.6 Hz, 1H), 2.63 (ddd, J=18.3, 9.9, 1.6 Hz, 1H).

Compound 4: (S)-2-(4-(5-(3,5-difluorophenyl)-4,5-dihydro-1H-pyrazole-1-carbonyl)piperazin-1-yl)-5-fluoro-N-methoxypyrimidine-4-carboxamide

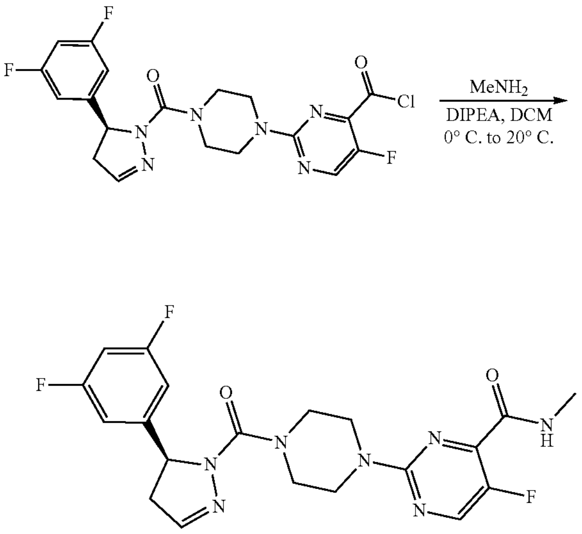

The titled compound 4 was prepared in 65.2% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 448.1 ($M+H^+$). $^1H$ NMR (400 MHz, DMSO-$d_6$) δ (ppm): 8.70 (d, J=4.9 Hz, 1H), 8.60 (d, J=2.8 Hz, 1H), 7.17-7.07 (m, 2H), 7.00 (dt, J=7.0, 2.2 Hz, 2H), 5.26 (dd, J=11.6, 9.9 Hz, 1H), 3.89-3.48 (m, 8H), 3.37 (ddd, J=18.3, 9.9, 1.6 Hz, 1H), 2.78 (d, J=4.8 Hz, 3H), 2.66 (ddd, J=18.3, 9.9, 1.6 Hz, 1H).

Compound 5: 2-(4-(5-(3,5-difluorophenyl)-4,5-dihydro-1H-pyrazole-1-carbonyl) piperazin-1-yl)-5-fluoro-N,N-dimethylpyrimidine-4-carboxamide

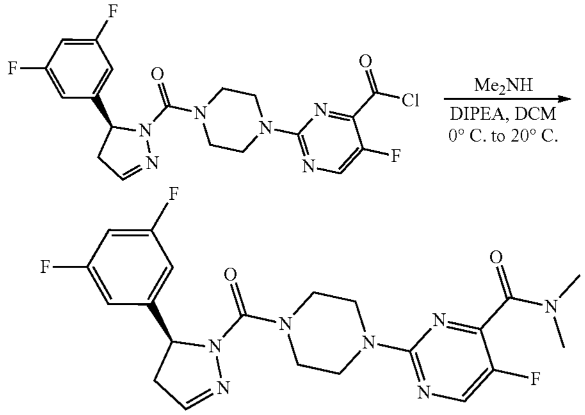

titled compound 5 was prepared in 56.3% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 462.1 ($M+H^+$). $^1H$ NMR (400 MHz, $CDCl_3$) δ (ppm): 8.26 (d, J=1.1 Hz, 1H), 6.87-6.77 (m, 3H), 6.72-6.66 (m, 1H), 5.33 (dd, J=11.7, 9.9 Hz, 1H), 3.92-3.81 (m, 2H), 3.81-3.68 (m, 4H), 3.66-3.56 (m, 2H), 3.31 (ddd, J=18.3, 11.7, 1.8 Hz, 1H), 3.12 (s, 3H), 2.96 (s, 3H), 2.68 (ddd, J=18.3, 9.9, 1.6 Hz, 1H).

Compound 6: (S)-2-(4-(5-(3,5-difluorophenyl)-4,5-dihydro-1H-pyrazole-1-carbonyl)piperazin-1-yl)-N-ethyl-5-fluoro-N-methylpyrimidine-4-carboxamide

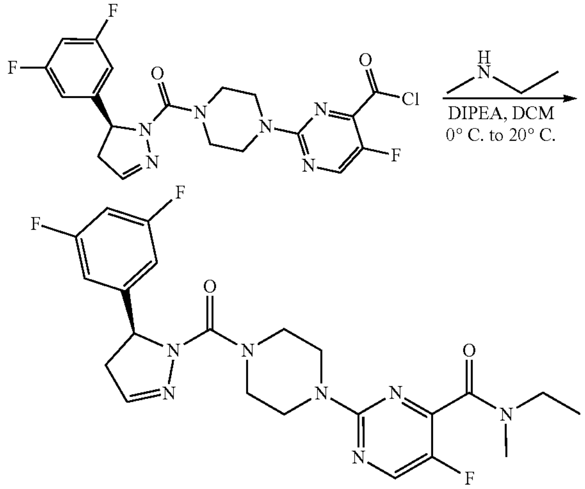

The titled compound 6 was prepared in 58.1% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 476.1 ($M+H^+$). $^1H$ NMR (400 MHz, $CDCl_3$) δ (ppm): 8.26-8.25 (m, 1H), 6.88-6.78 (m, 3H), 6.69 (tt, J=8.9, 2.3 Hz, 1H), 5.33 (dd, J=11.7, 9.9 Hz, 1H), 3.92-3.81 (m, 2H), 3.80-3.69 (m, 4H), 3.65-3.54 (m, 2H), 3.37-3.20 (m, 3H), 3.09 (s, 2H), 2.92 (s, 1H), 2.68 (ddd, J=18.3, 9.9, 1.6 Hz, 1H), 1.29-1.21 (m, 2H), 1.18 (t, J=7.1 Hz, 2H).

Compound 7: (S)-azetidin-1-yl(2-(4-(5-(3,5-difluorophenyl)-4,5-dihydro-1H-pyrazole-1-carbonyl)piperazin-1-yl)-5-fluoropyrimidin-4-yl)methanone

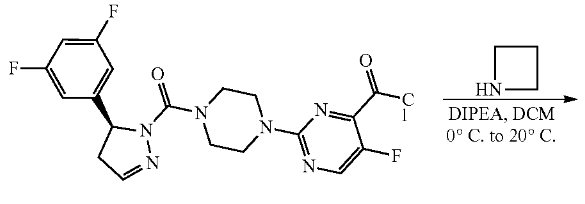

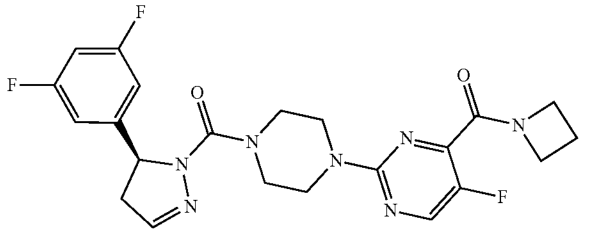

The titled compound 7 was prepared in 69.2% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 474.1 (M+H$^+$). $^1$H NMR (400 MHz, $CDCl_3$) δ (ppm): 8.30 (d, J=1.9 Hz, 1H), 6.89-6.78 (m, 3H), 6.69 (tt, J=8.8, 2.3 Hz, 1H), 5.33 (dd, J=11.7, 9.9 Hz, 1H), 4.37-4.29 (m, 2H), 4.28-4.19 (m, 2H), 3.93-3.56 (m, 8H), 3.32 (ddd, J=18.3, 11.7, 1.8 Hz, 1H), 2.68 (ddd, J=18.3, 9.9, 1.6 Hz, 1H), 2.43-2.29 (m, 2H).

Compound 8: (S)-(5-(3,5-difluorophenyl)-4,5-dihydro-1H-pyrazol-1-yl)(4-(5-fluoro-4-(pyrrolidine-1-carbonyl)pyrimidin-2-yl)piperazin-1-yl)methanone

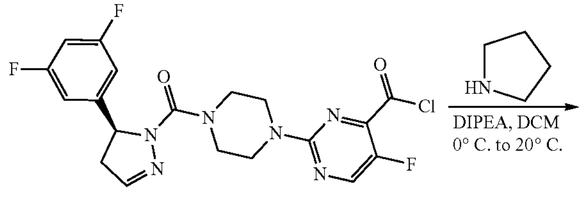

-continued

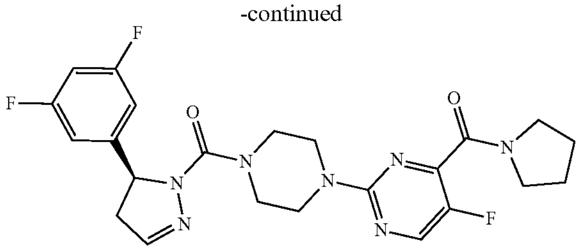

The titled compound 8 was prepared in 73.5% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 488.1 (M+H$^+$). $^1$H NMR (400 MHz, $CDCl_3$) δ (ppm): 8.30 (d, J=1.9 Hz, 1H), 6.89-6.78 (m, 3H), 6.69 (tt, J=8.8, 2.3 Hz, 1H), 5.33 (dd, J=11.7, 9.9 Hz, 1H), 4.37-4.29 (m, 2H), 4.28-4.19 (m, 2H), 3.93-3.56 (m, 12H), 3.37-3.34 (m, 1H), 2.73-2.63 (m, 1H), 1.99-1.91 (m, 4H).

Compound 9: (S)—N-cyclopropyl-2-(4-(5-(3,5-difluorophenyl)-4,5-dihydro-1H-pyrazole-1-carbonyl)piperazin-1-yl)-5-fluoro-N-methylpyrimidine-4-carboxamide

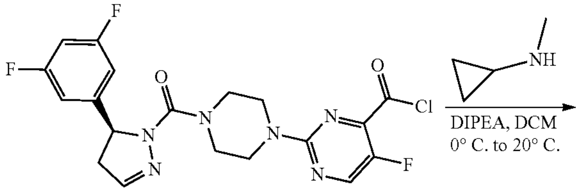

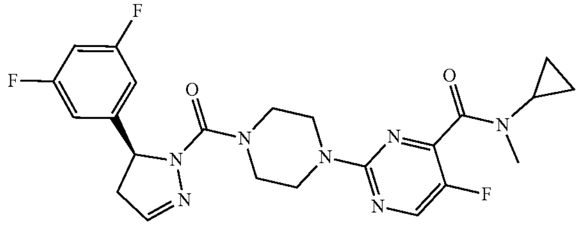

The titled compound 9 was prepared in 63.7% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 488.1 (M+H$^+$). $^1$H NMR (400 MHz, $CDCl_3$) δ (ppm): 8.25 (d, J=1.9 Hz, 1H), 6.87-6.78 (m, 3H), 6.69 (tt, J=8.9, 2.3 Hz, 1H), 5.32 (dd, J=11.7, 9.9 Hz, 1H), 3.90-3.82 (m, 2H), 3.80-3.70 (m, 4H), 3.66-3.57 (m, 2H), 3.31 (ddd, J=18.3, 11.7, 1.8 Hz, 1H), 3.11 (s, 3H), 2.81-2.75 (m, 1H), 2.68 (ddd, J=18.2, 9.9, 1.6 Hz, 1H), 0.64-0.55 (m, 4H).

Compound 10: (5-(3,5-difluorophenyl)-4,5-dihydro-1H-pyrazol-1-yl)(4-(5-fluoro-4-(3-(pyrrolidin-1-ylmethyl)azetidine-1-carbonyl)pyrimidin-2-yl)piperazin-1-yl)methanone

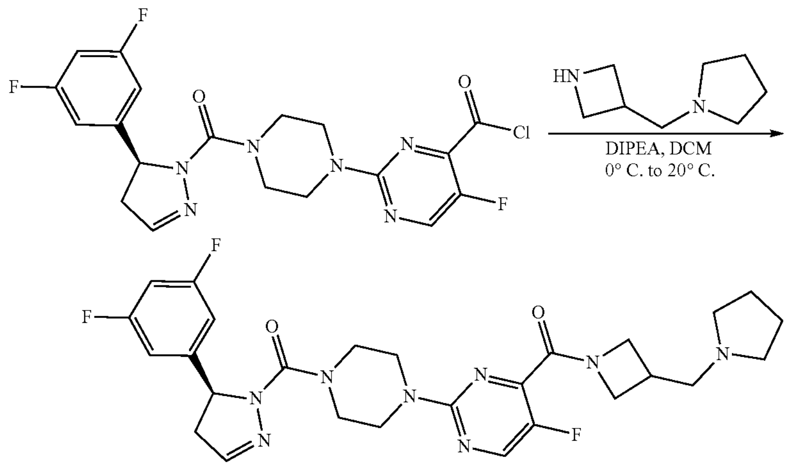

The titled compound 10 was prepared in 63.7% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 557.2 (M+H$^+$). $^1$H NMR (400 MHz, $CDCl_3$) δ (ppm): 8.30 (d, J=2.0 Hz, 1H), 6.88-6.77 (m, 3H), 6.68 (tt, J=8.8, 2.3 Hz, 1H), 5.33 (dd, J=11.7, 9.9 Hz, 1H), 4.57 (t, J=8.6 Hz, 1H), 4.36 (dd, J=10.8, 7.8 Hz, 1H), 4.19 (dd, J=9.8, 4.7 Hz, 1H), 3.96-3.56 (m, 9H), 3.31 (ddd, J=18.3, 11.8, 1.8 Hz, 1H), 3.19-3.17 (m, 3H), 3.00-2.93 (d, J=28.0 Hz, 4H), 2.68 (ddd, J=18.3, 9.8, 1.6 Hz, 1H), 2.01-1.97 (m, 4H).

Compound 11: (S)-2-(4-(5-(3,5-difluorophenyl)-4,5-dihydro-1H-pyrazole-1-carbonyl)piperazin-1-yl)-N-ethyl-5-fluoro-N-hydroxypyrimidine-4-carboxamide

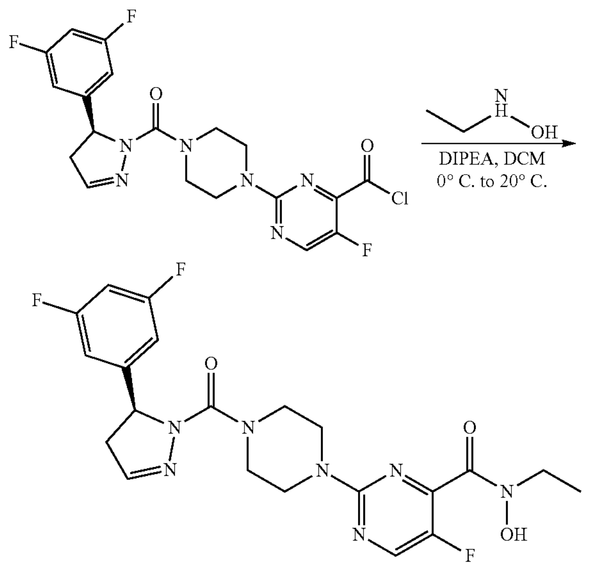

The titled compound 11 was prepared in 43.5% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 478.1 (M+H$^+$). $^1$H NMR (400 MHz, $CDCl_3$) δ (ppm): 8.72 (d, J=1.8 Hz, 1H), 7.27-7.16 (m, 3H), 7.09 (tt, J=9.1, 2.4 Hz, 1H), 5.72 (dd, J=11.7, 10.0 Hz, 1H), 4.33-3.94 (m, 8H), 3.79-3.63 (m, 1H), 3.15-3.00 (m, 1H), 2.12-1.96 (br, 1H), 1.78-1.67 (m, 2H), 1.63 (t, J=7.0 Hz, 3H).

Compound 12: (S)-(3,3-difluoroazetidin-1-yl)(2-(4-(5-(3,5-difluorophenyl)-4,5-dihydro-1H-pyrazole-1-carbonyl)piperazin-1-yl)-5-fluoropyrimidin-4-yl)methanone

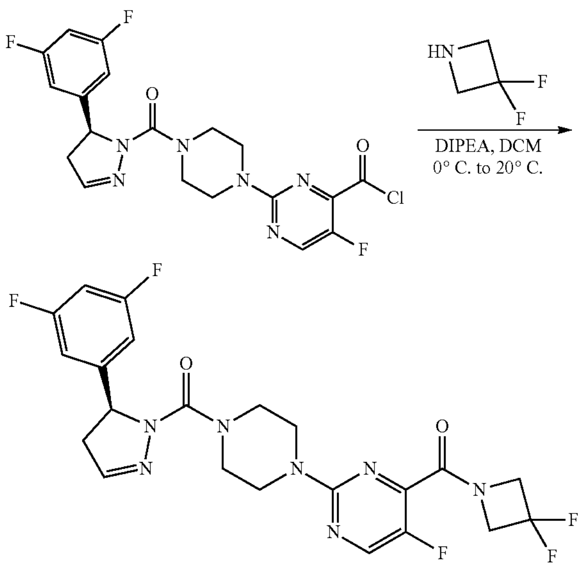

The titled compound 12 was prepared in 39.2% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 510.1 ($M+H^+$).

$^1H$ NMR (400 MHz, $CDCl_3$) δ (ppm): 8.37 (d, J=2.2 Hz, 1H), 6.89-6.79 (m, 3H), 6.70 (tt, J=8.9, 2.3 Hz, 1H), 5.34 (dd, J=11.7, 10.0 Hz, 1H), 4.73 (td, J=11.8, 1.4 Hz, 2H), 4.50 (td, J=11.8, 1.4 Hz, 2H), 3.90-3.59 (m, 8H), 3.33 (ddd, J=18.3, 11.8, 1.8 Hz, 1H), 2.69 (ddd, J=18.3, 9.8, 1.6 Hz, 1H).

Compound 13: (5-(3,5-difluorophenyl)-4,5-dihydro-1H-pyrazol-1-yl)(4-(5-fluoro-4-(3-hydroxyazetidine-1-carbonyl)pyrimidin-2-yl)piperazin-1-yl)methanone

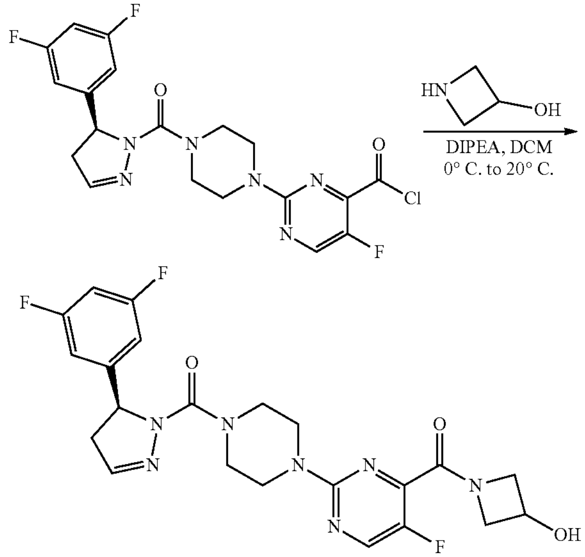

The titled compound 13 was prepared in 67.3% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 490.1 ($M+H^+$). $^1H$ NMR (400 MHz, $CDCl_3$) δ (ppm): 8.31 (d, J=2.0 Hz, 1H), 6.88-6.79 (m, 3H), 6.69 (tt, J=8.9, 2.3 Hz, 1H), 5.34 (dd, J=11.7, 10.0 Hz, 1H), 4.76-4.71 (m, 1H), 4.56-4.50 (m, 1H), 4.49-4.41 (m, 1H), 4.26-4.22 (m, 1H), 4.08-4.04 (m, 1H), 3.91-3.56 (m, 8H), 3.32 (ddd, J=18.3, 11.7, 1.8 Hz, 1H), 2.69 (ddd, J=18.3, 9.8, 1.6 Hz, 1H).

Compound 14: (5-(3,5-difluorophenyl)-4,5-dihydro-1H-pyrazol-1-yl)(4-(5-fluoro-4-(2-oxa-6-azaspiro[3.3]heptane-6-carbonyl)pyrimidin-2-yl)piperazin-1-yl)methanone

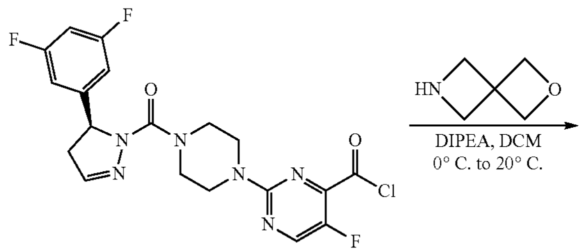

-continued

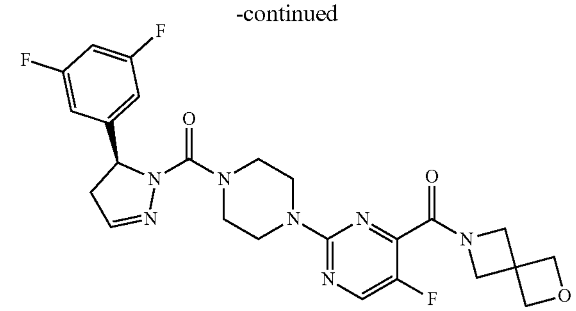

The titled compound 14 was prepared in 42.6% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 516.1 ($M+H^+$). $^1H$ NMR (400 MHz, $CDCl_3$) δ (ppm): 8.32 (d, J=2.0 Hz, 1H), 6.89-6.80 (m, 3H), 6.70 (tt, J=8.9, 2.3 Hz, 1H), 5.34 (dd, J=11.7, 10.0 Hz, 1H), 4.87-4.77 (m, 4H), 4.51 (d, J=1.2 Hz, 2H), 4.35 (d, J=1.1 Hz, 2H), 3.92-3.58 (m, 8H), 3.33 (ddd, J=18.3, 11.7, 1.8 Hz, 1H), 2.69 (ddd, J=18.3, 9.8, 1.6 Hz, 1H).

Compound 15: (3S)-1-(2-(4-(5-(3,5-difluorophenyl)-4,5-dihydro-1H-pyrazole-1-carbonyl)piperazin-1-yl)-5-fluoropyrimidine-4-carbonyl)pyrrolidine-3-carbonitrile

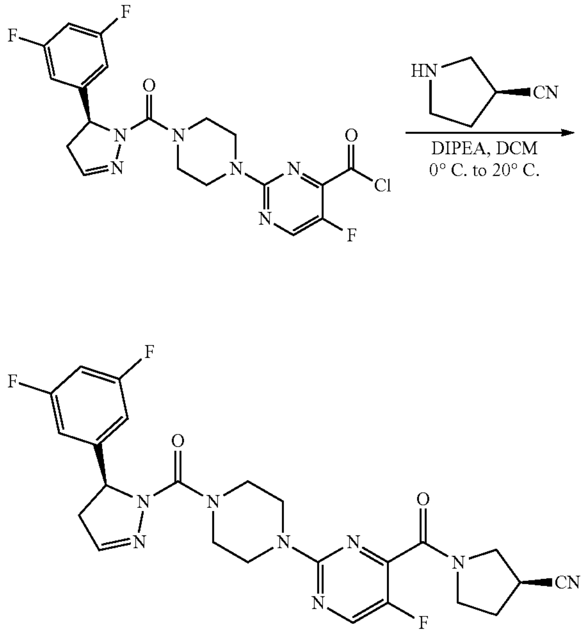

The titled compound 15 was prepared in 63.8% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 513.1 ($M+H^+$). $^1H$ NMR (400 MHz, $CDCl_3$) δ (ppm): 8.32 (dd, J=4.5, 1.3 Hz, 1H), 6.87-6.77 (m, 3H), 6.69 (tt, J=8.8, 2.3 Hz, 1H), 5.34 (dd, J=11.7, 10.0 Hz, 1H), 4.10-3.54 (m, 11H), 3.39-3.15 (m, 2H), 2.69 (ddd, J=18.3, 9.9, 1.6 Hz, 1H), 2.48-2.25 (m, 2H).

Compound 16: (3R)-1-(2-(4-(5-(3,5-difluorophenyl)-4,5-dihydro-1H-pyrazole-1-carbonyl)piperazin-1-yl)-5-fluoropyrimidine-4-carbonyl)pyrrolidine-3-carbonitrile

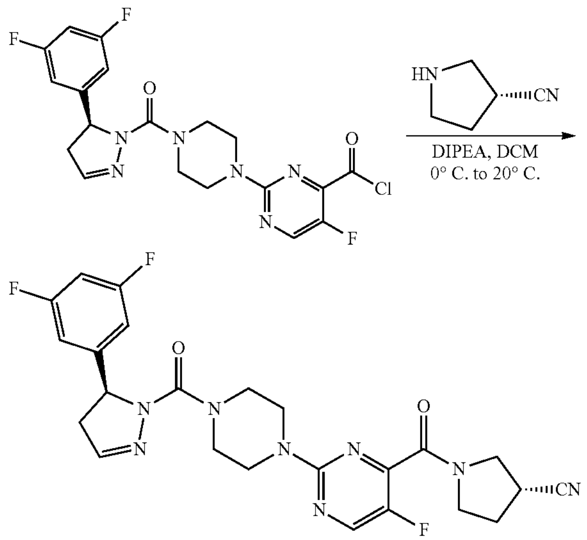

The titled compound 16 was prepared in 65.3% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 513.1 (M+H$^+$). $^1$H NMR (400 MHz, $CDCl_3$) δ (ppm): 8.32 (dd, J=4.5, 1.3 Hz, 1H), 6.87-6.77 (m, 3H), 6.69 (tt, J=8.8, 2.3 Hz, 1H), 5.34 (dd, J=11.7, 10.0 Hz, 1H), 4.10-3.54 (m, 11H), 3.39-3.15 (m, 2H), 2.69 (ddd, J=18.3, 9.9, 1.6 Hz, 1H), 2.48-2.25 (m, 2H).

Compound 17: (5-(3,5-difluorophenyl)-4,5-dihydro-1H-pyrazol-1-yl)(4-(5-fluoro-4-(piperidine-1-carbonyl)pyrimidin-2-yl)piperazin-1-yl)methanone

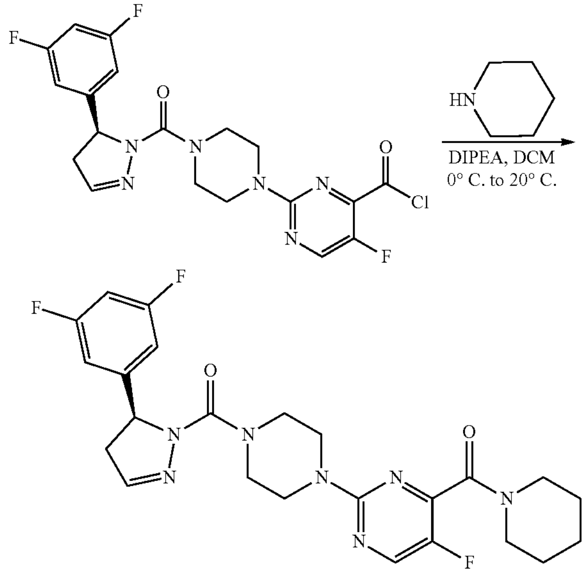

The titled compound 17 was prepared in 68.2% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 502.1 (M+H$^+$). $^1$H NMR (400 MHz, $CDCl_3$) δ (ppm): 8.24 (d, J=1.0 Hz, 1H), 6.86-6.78 (m, 3H), 6.69 (tt, J=8.8, 2.3 Hz, 1H), 5.34 (dd, J=11.7, 10.0 Hz, 1H), 3.93-3.53 (m, 12H), 3.32 (ddd, J=18.3, 11.8, 1.8 Hz, 1H), 2.68 (ddd, J=18.3, 9.9, 1.6 Hz, 1H), 1.93-1.53 (m, 6H).

Compound 18: (5-(3,5-difluorophenyl)-4,5-dihydro-1H-pyrazol-1-yl)(4-(5-fluoro-4-(morpholine-4-carbonyl)pyrimidin-2-yl)piperazin-1-yl)methanone

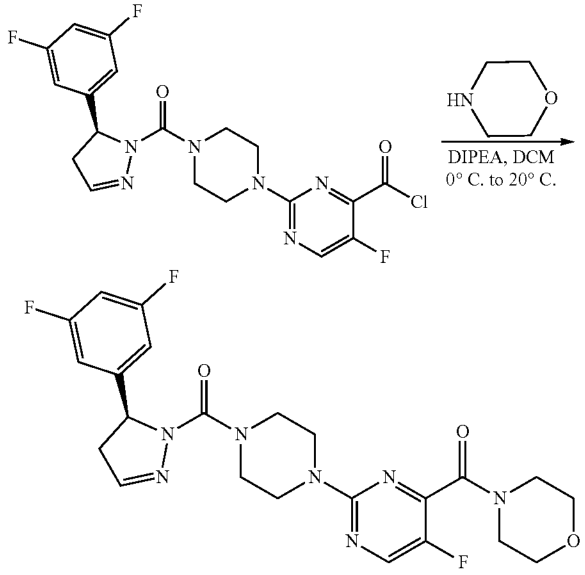

The titled compound 18 was prepared in 61.7% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 504.1 (M+H$^+$).

$^1$H NMR (400 MHz, $CDCl_3$) δ (ppm): 8.27 (d, J=1.0 Hz, 1H), 6.87-6.79 (m, 3H), 6.69 (tt, J=8.9, 2.3 Hz, 1H), 5.34 (dd, J=11.7, 10.0 Hz, 1H), 3.91-3.54 (m, 16H), 3.32 (ddd, J=18.3, 11.8, 1.8 Hz, 1H), 2.68 (ddd, J=18.3, 9.9, 1.6 Hz, 1H).

Compound 19: (5-(3,5-difluorophenyl)-4,5-dihydro-1H-pyrazol-1-yl)(4-(5-fluoro-4-(4-methylpiperazine-1-carbonyl)pyrimidin-2-yl)piperazin-1-yl)methanone

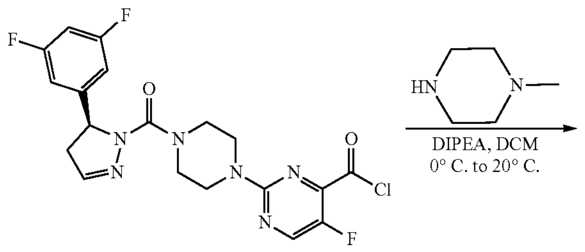

-continued

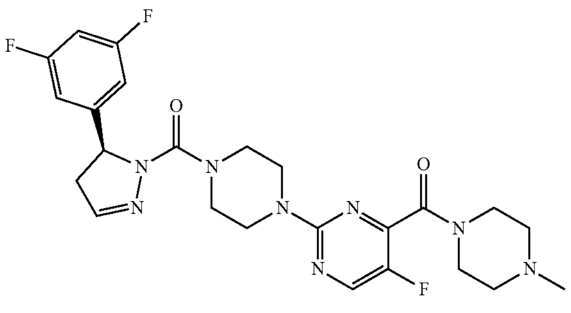

The titled compound 19 was prepared in 56.3% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 517.2 ($M+H^+$). $^1H$ NMR (400 MHz, $CDCl_3$) δ (ppm): 8.26 (d, J=1.0 Hz, 1H), 6.88-6.78 (m, 3H), 6.69 (tt, J=8.9, 2.3 Hz, 1H), 5.34 (dd, J=11.7, 10.0 Hz, 1H), 3.91-3.54 (m, 12H), 3.32 (ddd, J=18.3, 11.8, 1.8 Hz, 1H), 2.68 (ddd, J=18.3, 9.9, 1.6 Hz, 1H), 2.50 (t, J=5.1 Hz, 2H), 2.44-2.37 (m, 2H), 2.33 (s, 3H).

Compound 20: (S)-2-(4-(5-(3,5-difluorophenyl)-4,5-dihydro-1H-pyrazole-1-carbonyl)piperazin-1-yl)-5-fluoro-N-hydroxy-N-methylpyrimidine-4-carboxamide

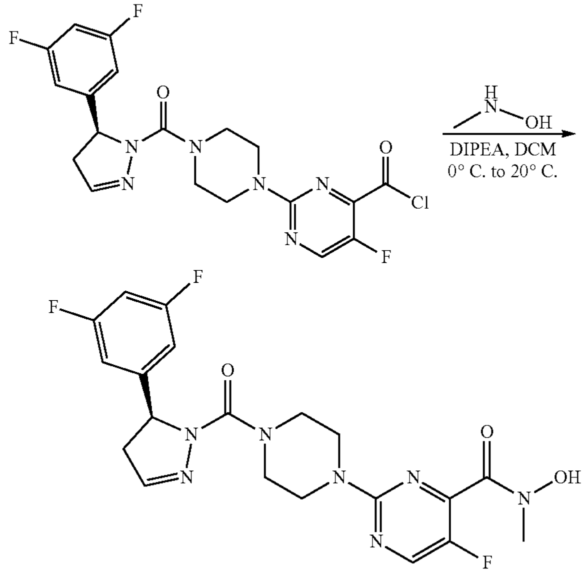

The titled compound 20 was prepared in 45.8% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 464.1 ($M+H^+$). $^1H$ NMR (400 MHz, $CDCl_3$) δ (ppm): 8.31 (dd, J=13.6, 1.3 Hz, 1H), 6.88-6.78 (m, 3H), 6.69 (tt, J=8.9, 2.4 Hz, 1H), 5.34 (dd, J=11.7, 10.0 Hz, 1H), 3.93-3.58 (m, 8H), 3.41 (s, 3H), 3.32 (ddd, J=18.3, 11.8, 1.8 Hz, 1H), 2.69 (ddd, J=18.3, 9.9, 1.7 Hz, 1H).

Compound 21: (S)-(5-(3,5-difluorophenyl)-4,5-dihydro-1H-pyrazol-1-yl)(4-(5-fluoro-4-(3-methoxyazetidine-1-carbonyl)pyrimidin-2-yl)piperazin-1-yl)methanone

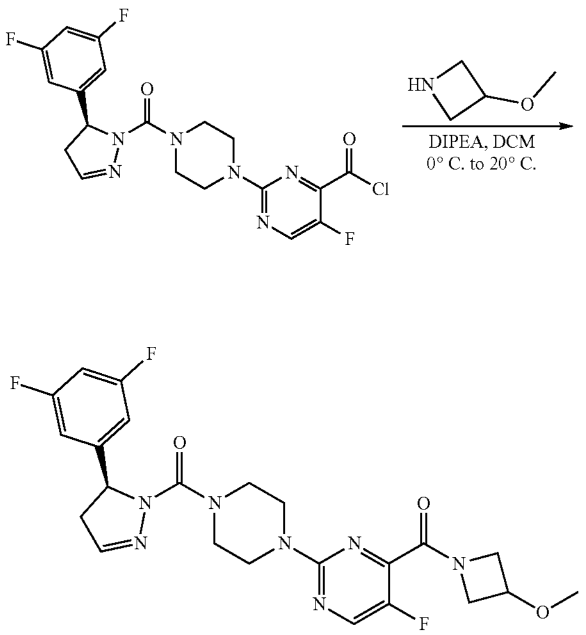

The titled compound was prepare in 46.1% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 504.1 ($M+H^+$). $^1H$ NMR (400 MHz, $CDCl_3$) δ (ppm): 8.31 (d, J=2.0 Hz, 1H), 6.88-6.78 (m, 3H), 6.69 (tt, J=8.9, 2.3 Hz, 1H), 5.34 (dd, J=11.7, 10.0 Hz, 1H), 4.52-4.32 (m, 2H), 4.3-4.18 (m, 2H), 4.07 (ddd, J=11.1, 3.8, 1.4 Hz, 1H), 3.93-3.56 (m, 8H), 3.36-3.28 (m, 4H), 2.69 (ddd, J=18.3, 9.8, 1.6 Hz, 1H).

Compound 22: (S)-(5-(3,5-difluorophenyl)-4,5-dihydro-1H-pyrazol-1-yl)(4-(5-fluoro-4-(3-methoxy-3-methylazetidine-1-carbonyl)pyrimidin-2-yl)piperazin-1-yl)methanone

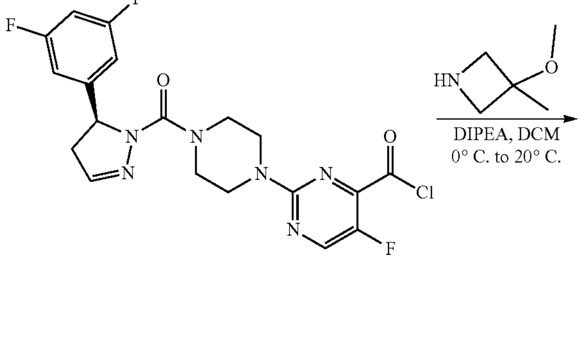

-continued

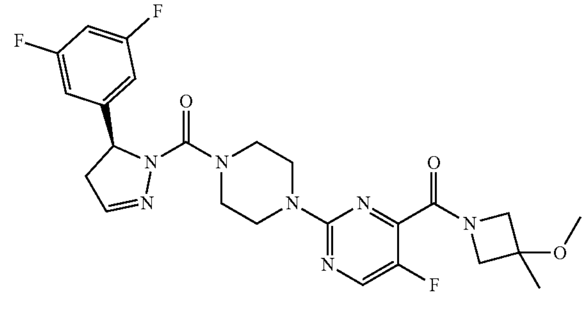

The titled compound 22 was prepared in 42.5% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 518.1 ($M+H^+$). $^1H$ NMR (400 MHz, $CDCl_3$) δ (ppm): 8.31 (d, J=2.0 Hz, 1H), 6.88-6.78 (m, 3H), 6.69 (tt, J=8.9, 2.3 Hz, 1H), 5.34 (dd, J=11.7, 10.0 Hz, 1H), 4.30 (dd, J=9.8, 3.6 Hz, 1H), 4.16 (d, J=10.8 Hz, 1H), 4.04 (ddd, J=9.7, 3.6, 1.5 Hz, 1H), 3.95 (dd, J=10.7, 1.4 Hz, 1H), 3.90-3.56 (m, 11H), 3.32 (ddd, J=18.3, 11.7, 1.9 Hz, 1H), 3.26 (d, J=0.4 Hz, 3H), 2.69 (ddd, J=18.3, 9.8, 1.6 Hz, 1H).

Compound 23: (S)-(5-(3,5-difluorophenyl)-4,5-dihydro-1H-pyrazol-1-yl)(4-(4-(3-ethoxyazetidine-1-carbonyl)-5-fluoropyrimidin-2-yl)piperazin-1-yl)methanone

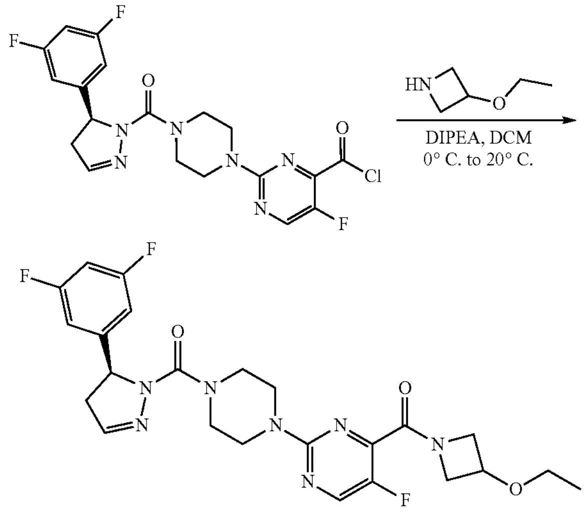

The titled compound 23 was prepared in 39.4% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 518.1 ($M+H^+$). $^1H$ NMR (400 MHz, $CDCl_3$) δ (ppm): 8.31 (d, J=2.0 Hz, 1H), 6.88-6.78 (m, 3H), 6.69 (tt, J=8.9, 2.3 Hz, 1H), 5.34 (dd, J=11.7, 10.0 Hz, 1H), 4.5-4.43 (m, 1H), 4.41-4.30 (m, 2H), 4.27-4.19 (m, 1H), 4.13-4.02 (m, 1H), 3.92-3.56 (m, 8H), 3.53-3.39 (m, 2H), 3.32 (ddd, J=18.3, 11.8, 1.8 Hz, 1H), 2.69 (ddd, J=18.3, 9.8, 1.6 Hz, 1H), 1.23 (td, J=7.0, 2.5 Hz, 3H).

Compound 24: (S)-(5-(3,5-difluorophenyl)-4,5-dihydro-1H-pyrazol-1-yl)(4-(5-fluoro-4-(3-isopropoxyazetidine-1-carbonyl)pyrimidin-2-yl)piperazin-1-yl)methanone

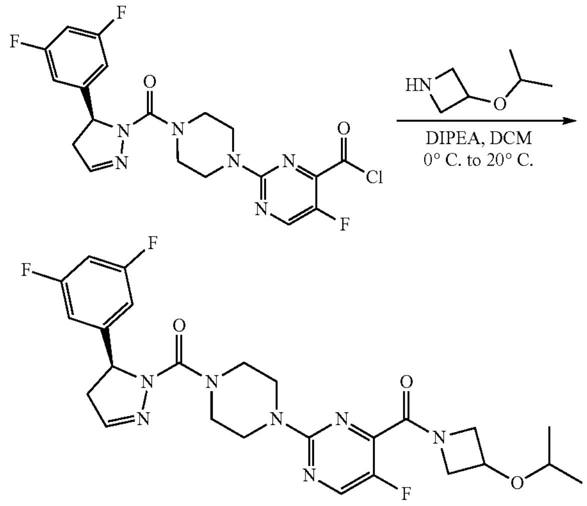

The titled compound 24 was prepared in 45.3% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 532.1 ($M+H^+$). $^1H$ NMR (400 MHz, $CDCl_3$) δ (ppm): 8.30 (d, J=1.9 Hz, 1H), 6.87-6.79 (m, 3H), 6.69 (tt, J=8.9, 2.3 Hz, 1H), 5.33 (dd, J=11.7, 10.0 Hz, 1H), 4.51-4.34 (m, 3H), 4.26-4.18 (m, 1H), 4.11-4.02 (m, 1H), 3.92-3.54 (m, 9H), 3.32 (ddd, J=18.3, 11.7, 1.8 Hz, 1H), 2.69 (ddd, J=18.3, 9.8, 1.6 Hz, 1H), 1.16 (dd, J=8.5, 6.1 Hz, 6H).

Compound 25: (S)-1-(2-(4-(5-(3,5-difluorophenyl)-4,5-dihydro-1H-pyrazole-1-carbonyl)piperazin-1-yl)-5-fluoropyrimidine-4-carbonyl)azetidine-3-carbonitrile

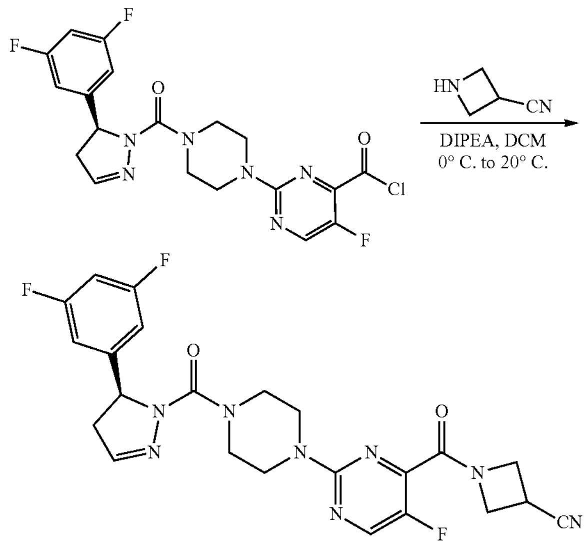

The titled compound 25 was prepared in 56.2% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 499.1 ($M+H^+$). $^1H$ NMR (400 MHz, $CDCl_3$) δ (ppm): 8.36 (d, J=2.2 Hz, 1H), 6.89-6.78 (m, 3H), 6.69 (tt, J=8.8, 2.3 Hz, 1H), 5.33 (dd, J=11.7, 10.0 Hz, 1H), 4.77-4.67 (m, 2H), 4.56-4.47 (m, 1H), 4.42 (dd, J=10.5, 6.4 Hz, 1H), 3.89-3.52 (m, 9H), 3.39-3.26 (m, 1H), 2.69 (ddd, J=18.3, 9.8, 1.6 Hz, 1H).

Compound 26: (S)-1-(2-(4-((S)-5-(3,5-difluorophenyl)-4,5-dihydro-1H-pyrazole-1-carbonyl)piperazin-1-yl)-5-fluoropyrimidine-4-carbonyl)pyrrolidine-3-carboxamide

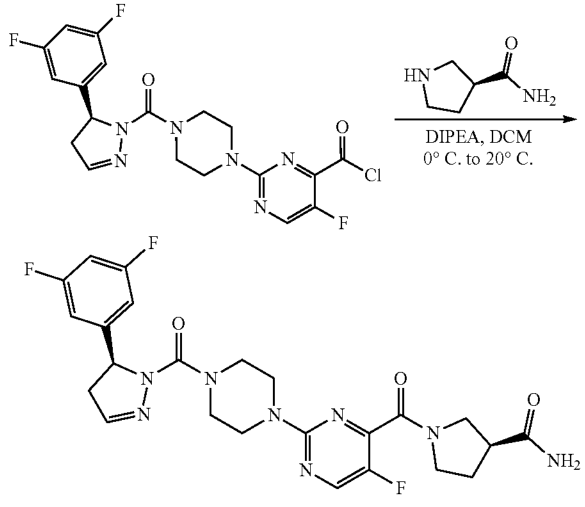

The titled compound 26 was prepared in 53.6% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 531.1 ($M+H^+$). $^1H$ NMR (400 MHz, $CDCl_3$) δ (ppm): 8.28 (d, J=1.2 Hz, 1H), 6.89-6.78 (m, 3H), 6.69 (dddt, J=10.4, 8.0, 2.5, 1.3 Hz, 1H), 5.65 (br, 1H), 5.50 (br, 1H), 5.33 (dd, J=11.7, 9.8 Hz, 1H), 4.07-3.44 (m, 12H), 3.38-3.20 (m, 1H), 3.03 (ddd, J=12.7, 8.1, 4.7 Hz, 1H), 2.68 (ddt, J=18.1, 10.0, 1.6 Hz, 1H), 2.37-2.12 (m, 2H).

Compound 27: (R)-1-(2-(4-((S)-5-(3,5-difluorophenyl)-4,5-dihydro-1H-pyrazole-1-carbonyl)piperazin-1-yl)-5-fluoropyrimidine-4-carbonyl)pyrrolidine-3-carboxamide

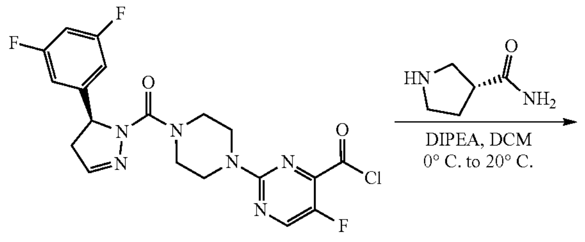

-continued

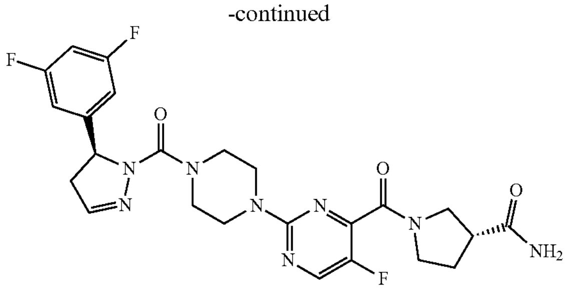

The titled compound 27 was prepared in 55.2% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 531.1 ($M+H^+$). $^1H$ NMR (400 MHz, $CDCl_3$) δ (ppm): 8.28 (d, J=1.2 Hz, 1H), 6.89-6.78 (m, 3H), 6.69 (dddt, J=10.4, 8.0, 2.5, 1.3 Hz, 1H), 5.65 (br, 1H), 5.50 (br, 1H), 5.33 (dd, J=11.7, 9.8 Hz, 1H), 4.07-3.44 (m, 12H), 3.38-3.20 (m, 1H), 3.03 (ddd, J=12.7, 8.1, 4.7 Hz, 1H), 2.68 (ddt, J=18.1, 10.0, 1.6 Hz, 1H), 2.37-2.12 (m, 2H).

Compound 28: (S)-(5-(3,5-difluorophenyl)-4,5-dihydro-1H-pyrazol-1-yl)(4-(4-(3-((dimethylamino)methyl)azetidine-1-carbonyl)-5-fluoropyrimidin-2-yl)piperazin-1-yl) methanone

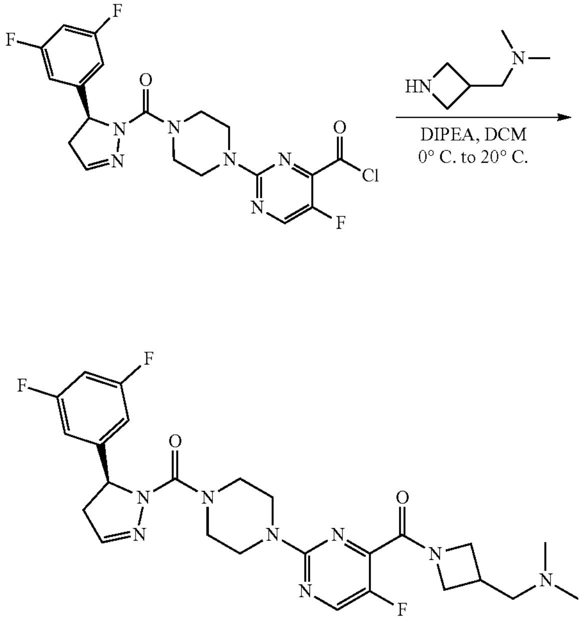

The titled compound 28 was prepared in 37.6% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 531.2 ($M+H^+$).

$^1H$ NMR (400 MHz, $CDCl_3$) δ (ppm): 8.30 (d, J=1.9 Hz, 1H), 6.89-6.77 (m, 3H), 6.69 (tt, J=8.9, 2.3 Hz, 1H), 5.33 (dd, J=11.7, 9.8 Hz, 1H), 4.44 (t, J=9.0 Hz, 1H), 4.36-4.27 (m, 1H), 3.99 (t, J=7.7 Hz, 1H), 3.91-3.55 (m, 12H), 3.32 (ddd, J=18.3, 11.7, 1.8 Hz, 1H), 3.00-2.85 (m, 1H), 2.76-2.62 (m, 1H), 2.31 (s, 6H).

Compound 29: (S)-(5-(3,5-difluorophenyl)-4,5-dihydro-1H-pyrazol-1-yl)(4-(5-fluoro-4-(2-azaspiro[3.3]heptane-2-carbonyl)pyrimidin-2-yl)piperazin-1-yl)methanone

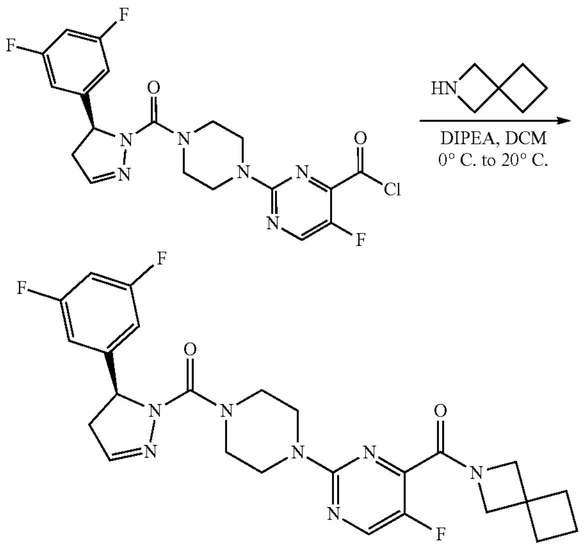

The titled compound 29 was prepared in 41.5% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 531.2 ($M+H^+$). $^1H$ NMR (400 MHz, $CDCl_3$) δ (ppm): 8.29 (d, J=2.0 Hz, 1H), 6.88-6.79 (m, 3H), 6.69 (tt, J=8.8, 2.3 Hz, 1H), 5.33 (dd, J=11.7, 9.8 Hz, 1H), 4.22 (s, 2H), 4.15 (s, 2H), 3.92-3.57 (m, 8H), 3.32 (ddd, J=18.3, 11.8, 1.8 Hz, 1H), 2.69 (ddd, J=18.3, 9.9, 1.6 Hz, 1H), 2.24-2.14 (m, 2H), 1.26-1.20 (m, 4H).

Compound 30: (S)-1-(2-(4-(5-(3,5-difluorophenyl)-4,5-dihydro-1H-pyrazole-1-carbonyl)piperazin-1-yl)-5-fluoropyrimidine-4-carbonyl)azetidine-3-carboxamide

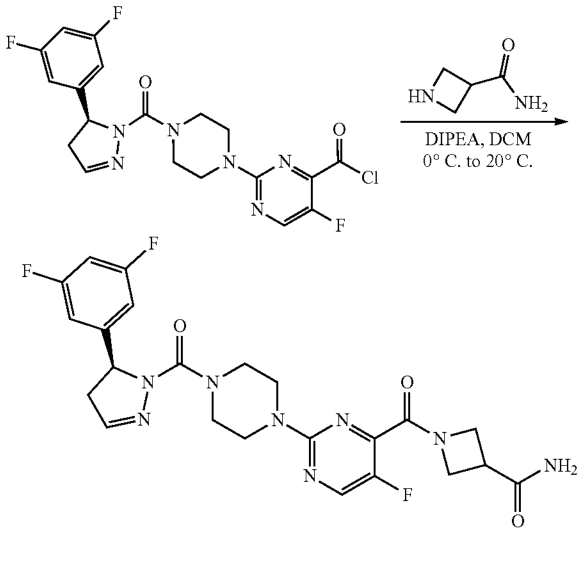

The titled compound 30 was prepared in 63.1% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 517.1 ($M+H^+$). $^1H$ NMR (400 MHz, $CDCl_3$) δ (ppm): 8.33 (d, J=2.1 Hz, 1H), 6.88-6.78 (m, 3H), 6.74-6.64 (m, 1H), 5.79 (br, 1H), 5.64 (br, 1H), 5.33 (dd, J=11.7, 9.8 Hz, 1H), 4.70-4.60 (m, 1H), 4.56-4.51 (m, 1H), 4.43-4.33 (m, 2H), 3.94-3.55 (m, 8H), 3.43-3.40 (m, 1H), 3.32 (ddd, J=18.3, 11.8, 1.8 Hz, 1H), 2.69 (ddd, J=18.3, 9.9, 1.6 Hz, 1H).

Compound 31: ((S)-5-(3,5-difluorophenyl)-4,5-dihydro-1H-pyrazol-1-yl)(4-(4-((S)-3-(dimethylamino)pyrrolidine-1-carbonyl)-5-fluoropyrimidin-2-yl)piperazin-1-yl)methanone

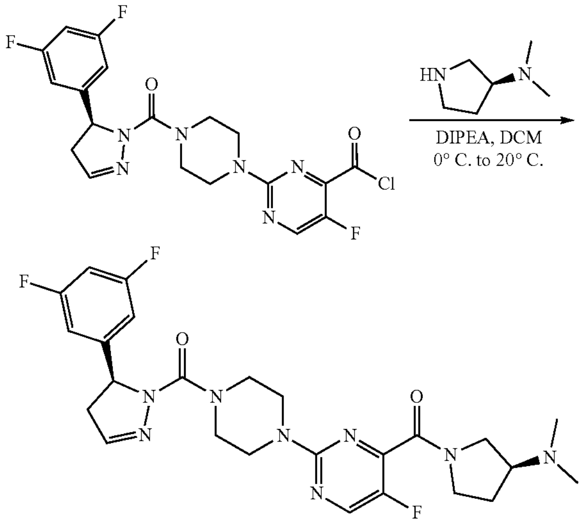

The titled compound 31 was prepared in 76.2% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 531.1 ($M+H^+$). $^1H$ NMR (400 MHz, $CDCl_3$) δ (ppm): 8.29 (dd, J=5.3, 1.3 Hz, 1H), 6.86-6.77 (m, 3H), 6.69 (ttd, J=8.9, 2.4, 1.2 Hz, 1H), 5.33 (dd, J=11.7, 9.8 Hz, 1H), 4.06-3.44 (m, 12H), 3.31 (ddd, J=18.3, 9.9, 1.6 Hz, 1H), 2.92-2.83 (m, 1H), 2.68 (ddd, J=18.3, 9.9, 1.6 Hz, 1H), 2.36 (s, 3H), 2.28 (s, 3H), 2.23-2.15 (m, 1H), 2.02-1.82 (m, 1H).

Compound 32: ((S)-5-(3,5-difluorophenyl)-4,5-dihydro-1H-pyrazol-1-yl)(4-(4-((R)-3-(dimethylamino)pyrrolidine-1-carbonyl)-5-fluoropyrimidin-2-yl)piperazin-1-yl)methanone

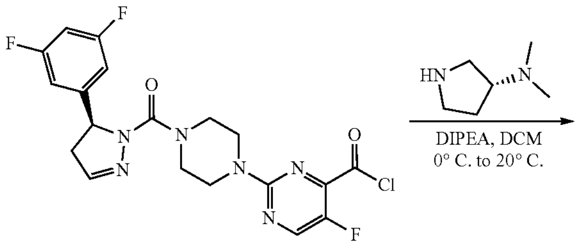

-continued

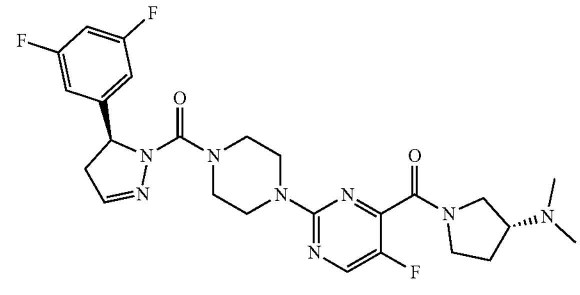

The titled compound 32 was prepared in 78.1% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 531.1 (M+H$^+$). $^1$H NMR (400 MHz, $CDCl_3$) δ (ppm): 8.29 (dd, J=5.3, 1.3 Hz, 1H), 6.86-6.77 (m, 3H), 6.69 (ttd, J=8.9, 2.4, 1.2 Hz, 1H), 5.33 (dd, J=11.7, 9.8 Hz, 1H), 4.06-3.44 (m, 12H), 3.31 (ddd, J=18.3, 9.9, 1.6 Hz, 1H), 2.92-2.83 (m, 1H), 2.68 (ddd, J=18.3, 9.9, 1.6 Hz, 1H), 2.36 (s, 3H), 2.28 (s, 3H), 2.23-2.15 (m, 1H), 2.02-1.82 (m, 1H).

Compound 33: (S)-(5-(3,5-difluorophenyl)-4,5-dihydro-1H-pyrazol-1-yl)(4-(4-(3-(dimethylamino) azetidine-1-carbonyl)-5-fluoropyrimidin-2-yl)piperazin-1-yl)methanone

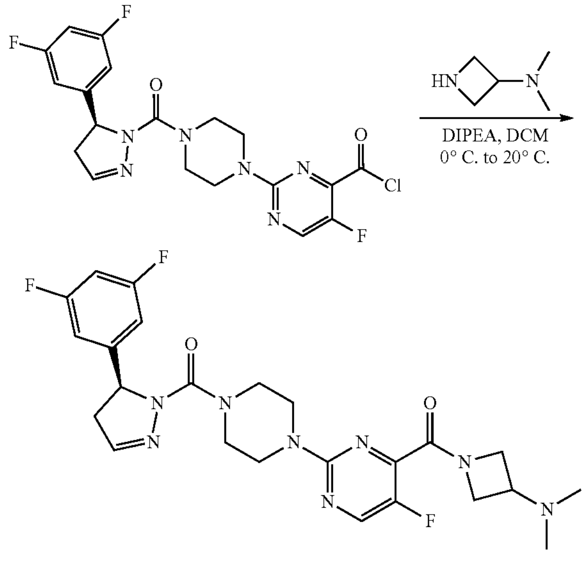

The titled compound 33 was prepared in 75.8% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 517.1 (M+H$^+$). $^1$H NMR (400 MHz, $CDCl_3$) δ (ppm): 8.26 (dd, J=7.3, 1.0 Hz, 1H), 6.87-6.78 (m, 3H), 6.69 (tt, J=8.9, 2.3 Hz, 1H), 5.33 (dd, J=11.7, 9.8 Hz, 1H), 3.94-3.54 (m, 13H), 3.31 (ddd, J=18.3, 9.9, 1.6 Hz, 1H), 3.22 (s, 3H), 2.68 (ddd, J=18.3, 9.9, 1.6 Hz, 1H), 2.31 (s, 3H).

Compound 34: (S)—N-(cyanomethyl)-2-(4-(5-(3,5-difluorophenyl)-4,5-dihydro-1H-pyrazole-1-carbonyl)piperazin-1-yl)-5-fluoro-N-methylpyrimidine-4-carboxamide

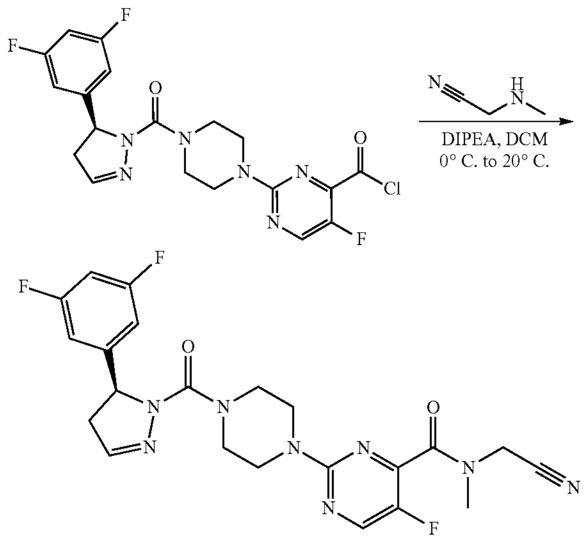

The titled compound 34 was prepared in 82.4% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 487.1 (M+H$^+$). $^1$H NMR (400 MHz, $CDCl_3$) δ (ppm): 8.33 (dd, J=13.1, 1.1 Hz, 1H), 6.89-6.78 (m, 3H), 6.74-6.64 (m, 1H), 5.33 (dd, J=11.7, 9.8 Hz, 1H), 4.53 (s, 2H), 3.96-3.57 (m, 8H), 3.32 (ddt, J=18.2, 11.7, 2.1 Hz, 1H), 3.24 (s, 1H), 3.12 (s, 2H), 2.68 (ddt, J=18.3, 9.9, 1.9 Hz, 1H).

Compound 35: (S)-2-(4-(5-(3,5-difluorophenyl)-4,5-dihydro-1H-pyrazole-1-carbonyl)piperazin-1-yl)-N-ethylpyrimidine-4-carboxamide

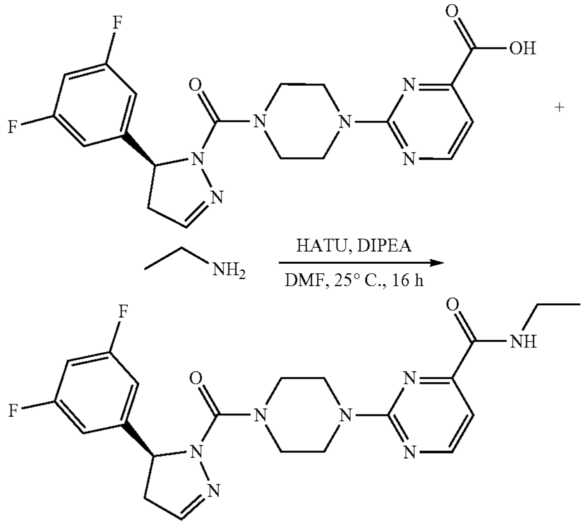

The titled compound 35 was prepared in 25.6% yield from (S)-2-(4-(5-(3,5-difluorophenyl)-4,5-dihydro-1H-pyrazole-1-carbonyl)piperazin-1-yl)pyrimidine-4-carboxylic acid according to the procedure outlined for compound 2. LC-MS (m/z) 444.1 (M+H$^+$). $^1$H NMR (400 MHz, $CDCl_3$) δ (ppm): δ 8.53 (d, J=4.8 Hz, 1H), 7.70 (brs, 1H), 7.33 (d, J=4.8 Hz, 1H), 6.82-6.87 (m, 3H), 6.68-6.73 (m, 1H), 5.34 (dd, J=10.0, 12.0 Hz, 1H), 3.92-3.98 (m, 2H), 3.77-3.87 (m, 4H), 3.64-3.70 (m, 2H), 3.49 (q, J=7.2 Hz, 2H), 3.33 (ddd, J=2.0, 12.0, 13.6 Hz, 1H), 2.70 (ddd, J=1.6, 9.6, 11.2 Hz, 1H), 1.27 (t, J=7.2 Hz, 3H). Mass (ESI): m/z calcd for $C_{21}H_{23}F_2N_7O_2$ 443.5, found 444.6 [M+H]$^+$.

Compound 36: (S)-azetidin-1-yl(2-(4-(5-(3,5-difluorophenyl)-4,5-dihydro-1H-pyrazole-1-carbonyl)piperazin-1-yl)pyrimidin-4-yl)methanone

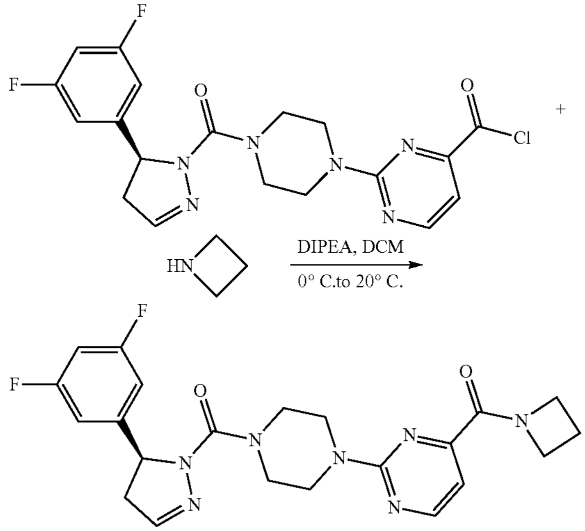

The titled compound 36 was prepared in analogous manner to the preparation of compound 2. H NMR (400 MHz, $CDCl_3$) δ 7.76-7.49 (m, 1H), 6.90-6.49 (m, 4H), 5.48-5.13 (m, 2H), 4.70-4.00 (m, 8H), 3.36 (dd, J=18.3, 12.5 Hz, 1H), 2.71 (dd, J=18.8, 6.4 Hz, 1H), 2.38-2.16 (m, 2H), 1.81-1.51 (m, 2H), 1.07-0.64 (m, 2H).

Compound 37: (S)-(5-(3,5-difluorophenyl)-4,5-dihydro-1H-pyrazol-1-yl)(4-(4-(3-isopropoxyazetidine-1-carbonyl)pyrimidin-2-yl)piperazin-1-yl)methanone

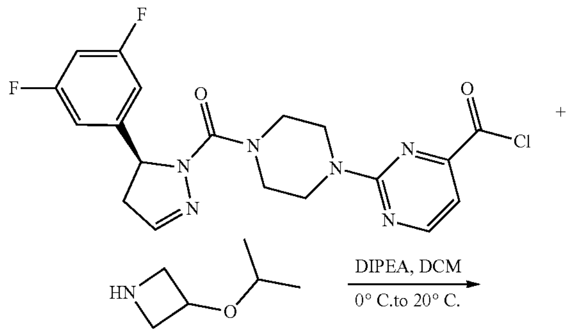

-continued

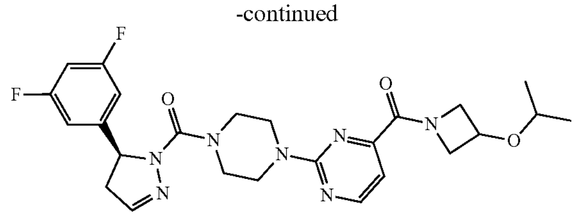

The titled compound 37 was prepared in analogous manner to the preparation of compound 2. $^1$H NMR (400 MHz, $CDCl_3$) δ 8.45 (d, J=4.8 Hz, 1H), 7.19 (d, J=4.8 Hz, 1H), 6.89-6.76 (m, 2H), 6.72-6.65 (m, 1H), 5.33 (dd, J=10, 11.6 Hz, 1H), 4.92-4.74 (m, 1H), 4.58-4.45 (m, 1H), 4.46-4.24 (m, 2H), 4.12-3.99 (m, 1H), 3.96-3.55 (m, 8H), 3.32 (ddd, J=18.3, 11.7, 1.8 Hz, 1H), 2.69 (ddd, J=18.3, 9.9, 1.6 Hz, 1H), 1.21-1.11 (m, 6H).

Compound 38: 2-(4-(5-(3,5-difluorophenyl)-4,5-dihydro-1H-pyrazole-1-carbonyl) piperazin-1-yl) pyrimidine-4-carboxamide

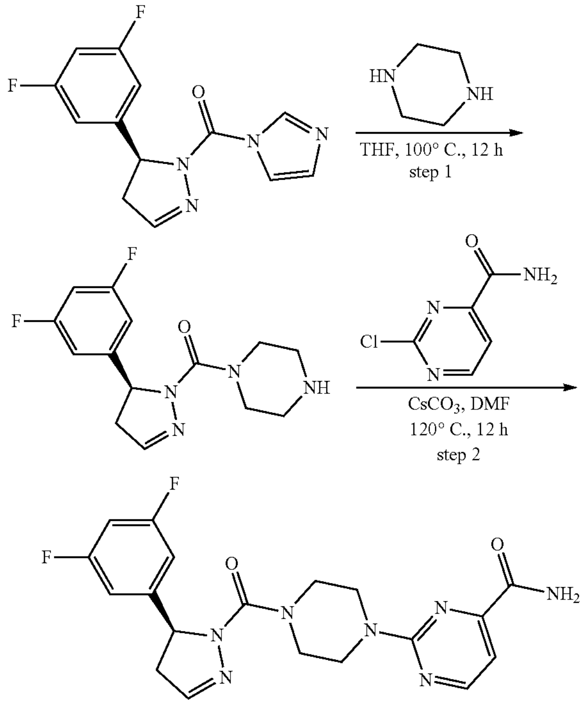

Step 1:

(S)-(5-(3,5-difluorophenyl)-4,5-dihydro-1H-pyrazol-1-yl)(1H-imidazol-1-yl)methanone (1 g, 3.62 mmol) was dissolved in 30 ml of dry THF, piperazine (6.24 g, 72.4 mmol) was added.

The mixture was stirred at 100° C. for 12 h. The mixture was extracted with DCM, washed with brine, dried ($Na_2SO_4$), and concentrated to dryness to give the desired product. LC-MS (m/z) 295.1 (M+H$^+$).

Step 2: To a solution of (S)-(5-(3,5-difluorophenyl)-4,5-dihydro-1H-pyrazol-1-yl)(piperazin-1-yl)methanone (200 mg, 0.680 mmol) in DMF (3 mL) was added 2-chloropyrimidine-4-carboxamide (118 mg, 0.748 mmol). The reaction mixture was stirred at 120° C. for 12 h. The crude purified by reversed-phase chromatography. 180 mg target compound 38 was obtained as a white solid, Yield: 63.8%. LC-MS (m/z) 416.1 (M+H$^+$). $^1$H NMR (400 MHz, $CDCl_3$) δ (ppm): 8.55 (d, J=4.8, 1H), 7.56 (s, 1H), 7.31 (d, J=4.8, 1H), 6.86-6.81 (m, 3H), 6.72-6.67 (m, 1H), 5.67 (s, 1H), 5.34 (dd, J=11.7, 9.8 Hz, 1H), 3.98-3.93 (m, 2H), 3.87-3.76 (m, 4H), 3.68-3.63 (m, 2H), 3.33 (ddd, J=18.3, 11.7, 1.8 Hz, 1H), 2.70 (ddd, J=18.3, 9.8, 1.6 Hz, 1H).

Compound 39: (S)-6-(4-(5-(3,5-difluorophenyl)-4,5-dihydro-1H-pyrazole-1-carbonyl)piperazin-1-yl)pyrazine-2-carboxamide

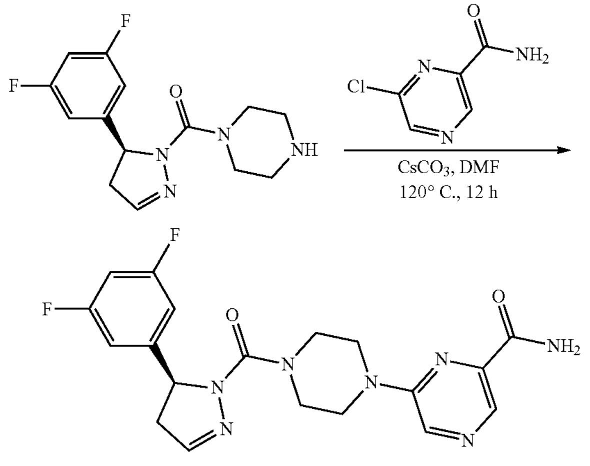

To a solution of (S)-(5-(3,5-difluorophenyl)-4,5-dihydro-1H-pyrazol-1-yl)(piperazin-1-yl)methanone (200 mg, 679.6 umol) in DMF (5 mL) was added 6-chloropyrazine-2-carboxamide (117.7 mg, 747.5 umol) and $CsCO_3$ (263 mg, 1.36 mmol). The reaction mixture was stirred at 120° C. for 12 h. The crude was purified by Pre-HPLC. 130 mg target was obtained as a white solid. Yield: 46.1%. LC-MS (m/z) 416.3 (M+H$^+$).

$^1$H NMR (400 MHz, DMSO-$d_6$) δ (ppm): 8.46 (s, 1H), 8.35 (s, 1H), 8.09 (s, 1H), 7.65 (s, 1H), 7.16-7.05 (m, 2H), 6.98 (dt, J=7.0, 2.1 Hz, 2H), 5.24 (dd, J=11.6, 9.9 Hz, 1H), 3.83-3.47 (m, 8H), 3.35 (ddd, J=18.3, 11.6, 1.9 Hz, 1H), 2.64 (ddd, J=18.3, 9.8, 1.6 Hz, 1H).

Compound 40: (S)-6-(4-(5-(3,5-difluorophenyl)-4,5-dihydro-1H-pyrazole-1-carbonyl)piperazin-1-yl)pyrimidine-4-carboxamide

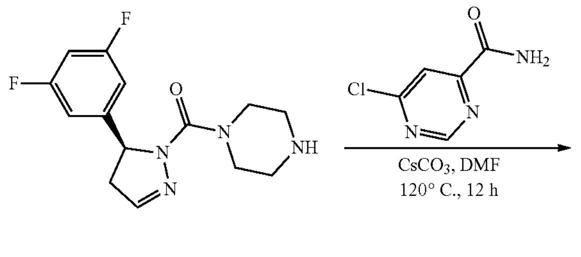

-continued

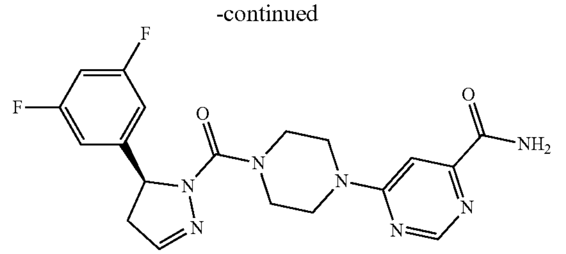

The titled compound 40 was prepared in 67.1% yield from 6-chloropyrimidine-4-carboxamide and (S)-(5-(3,5-difluorophenyl)-4,5-dihydro-1H-pyrazol-1-yl)(piperazin-1-yl)methanone according to the procedure outlined for compound 38. LC-MS (m/z) 416.1 (M+H$^+$)$^1$H NMR (400 MHz, DMSO-$d_6$) δ (ppm): 8.62 (d, J=0.9 Hz, 1H), 8.25 (s, 1H), 7.95 (s, 1H), 7.42 (S, 1H), 7.15-7.04 (m, 2H), 7.00-6.97 (m, 2H), 5.24 (dd, J=11.6, 9.9 Hz, 1H), 3.86-3.51 (m, 8H), 3.35 (ddd, J=18.4, 11.7, 1.9 Hz, 1H), 2.64 (ddd, J=18.4, 9.9, 1.7 Hz, 1H).

Compound 41: (S)-2-(4-(5-phenyl-4,5-dihydro-1H-pyrazole-1-carbonyl)piperazin-1-yl)pyrimidine-4-carboxamide

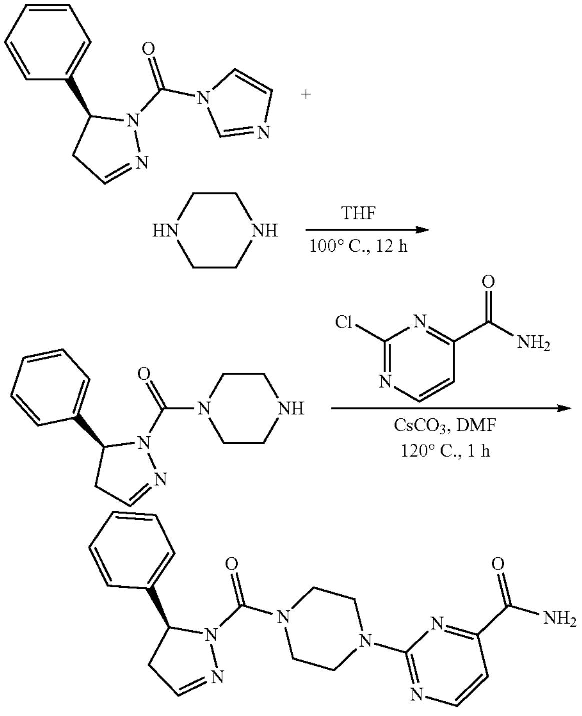

The titled compound 41 was prepared in two steps 53.1% yield from (S)-(1H-imidazol-1-yl)(5-phenyl-4,5-dihydro-1H-pyrazol-1-yl)methanone according to the procedure outlined for compound 38. LC-MS (m/z) 380.1 (M+H$^+$). $^1$H NMR (400 MHz, $CDCl_3$) δ (ppm): 8.54 (d, J=4.8 Hz, 1H), 7.57 (s, 1H), 7.37-7.28 (m, 6H), 6.86 (t, J=1.7 Hz, 1H), 5.63 (s, 1H), 5.38 (dd, J=11.8, 9.7 Hz, 1H), 3.98-3.58 (m, 8H), 3.33 (ddd, J=18.3, 11.8, 1.8 Hz, 1H), 2.76 (ddd, J=18.3, 9.7, 1.6 Hz, 1H).

Compound 42: (S)-2-(4-(5-(3-cyano-5-fluorophenyl)-4,5-dihydro-1H-pyrazole-1-carbonyl)piperazin-1-yl)pyrimidine-4-carboxamide

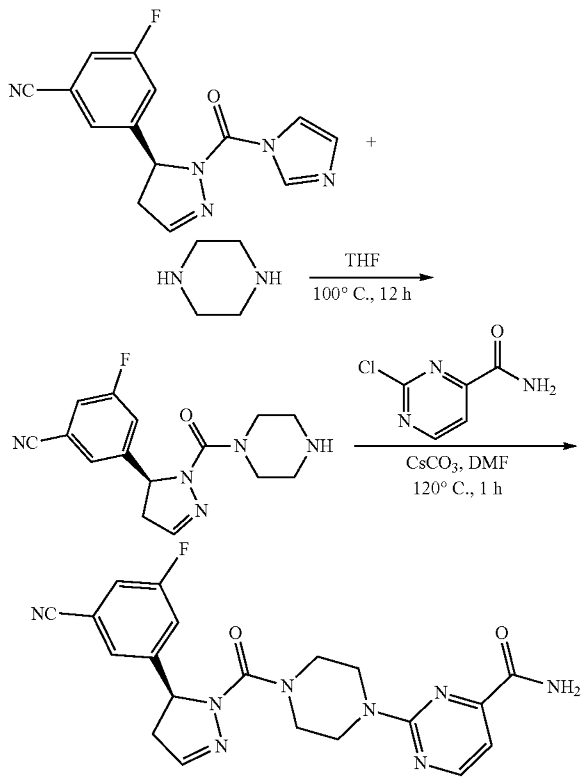

The titled compound 42 was prepared in two steps 65.2% yield from (S)-3-(1-(1H-imidazole-1-carbonyl)-4,5-dihydro-1H-pyrazol-5-yl)-5-fluorobenzonitrile according to the procedure outlined for compound 38. LC-MS (m/z) 443.1 $(M+H^+)$. $^1$H NMR (400 MHz, $CDCl_3$) δ (ppm): 8.55 (d, J=4.8 Hz, 1H), 7.57 (s, 1H), 7.42 (t, J=1.5 Hz, 1H), 7.31 (d, J=4.8 Hz, 1H), 7.30-7.21 (m, 2H), 6.91-6.87 (m, 1H), 5.67 (s, 1H), 5.37 (dd, J=11.7, 10.0 Hz, 1H), 4.02-3.59 (m, 8H), 3.36 (ddd, J=18.3, 11.7, 1.8 Hz, 1H), 2.70 (ddd, J=18.3, 10.0, 1.6 Hz, 1H).

Compound 43: (S)-2-(4-(5-(5-cyanopyridin-3-yl)-4,5-dihydro-1H-pyrazole-1-carbonyl)piperazin-1-yl)pyrimidine-4-carboxamide

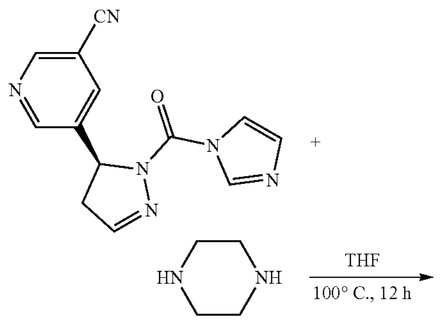

-continued

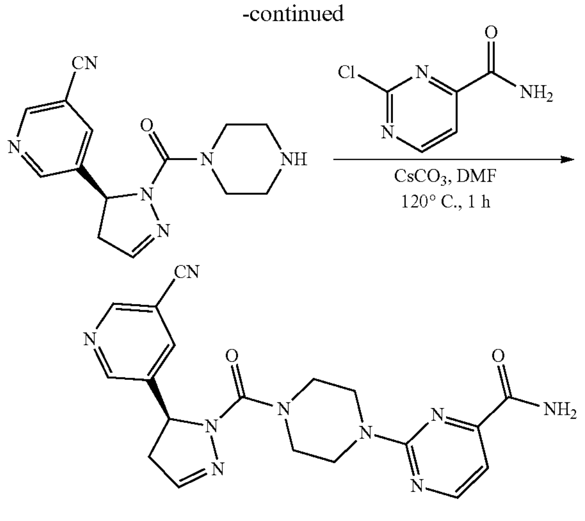

The titled compound 43 was prepared in two steps 42.6% yield from (S)-5-(1-(1H-imidazole-1-carbonyl)-4,5-dihydro-1H-pyrazol-5-yl)nicotinonitrile according to the procedure outlined for compound 38. LC-MS (m/z) 406.1 $(M+H^+)$. $^1$H NMR (400 MHz, $CDCl_3$) δ (ppm): 8.80 (dd, J=3.8, 2.1 Hz, 2H), 8.55 (d, J=4.8 Hz, 1H), 7.91 (t, J=2.1 Hz, 1H), 7.56 (s, 1H), 7.32 (d, J=4.8 Hz, 1H), 6.94 (t, J=1.7 Hz, 1H), 5.64 (s, 1H), 5.42 (dd, J=11.7, 10.3 Hz, 1H), 4.08-3.52 (m, 8H), 3.40 (ddd, J=18.2, 11.7, 1.9 Hz, 1H), 2.75 (ddd, J=18.2, 10.2, 1.6 Hz, 1H).

Compound 44: (S)-2-(4-(5-(3,5-difluorophenyl)-4,5-dihydro-1H-pyrazole-1-carbonyl)piperazin-1-yl)pyrimidine-4-carboxylic acid

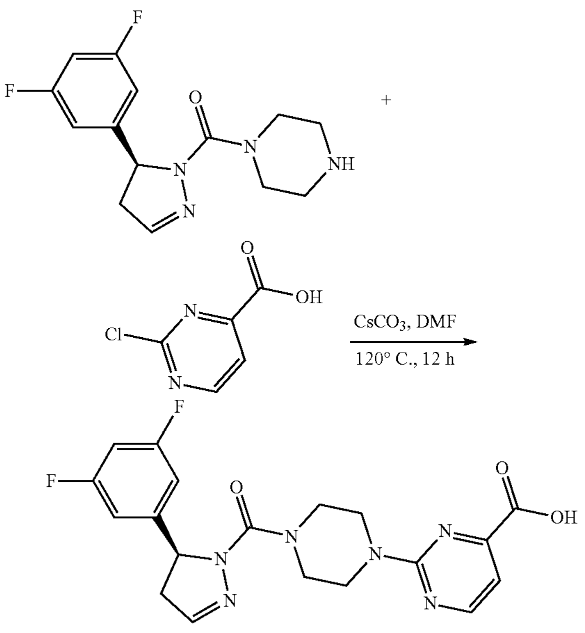

The titled compound 44 was prepared in 76.2% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 38. LC-MS (m/z) 417.1 (M+H$^+$). $^1$H NMR (400 MHz, $CDCl_3$) δ (ppm): δ 8.62 (d, J=4.8 Hz, 1H), 7.31 (d, J=4.8 Hz, 1H), 6.87 (t, J=1.6 Hz, 1H), 6.81-6.84 (m, 2H), 6.68-6.73 (m, 1H), 5.34 (dd, J=10.0, 11.6 Hz, 1H), 3.93-4.00 (m, 2H), 3.78-3.89 (m, 4H), 3.65-3.70 (m, 2H), 3.34 (ddd, J=1.6, 11.6, 13.6 Hz, 1H), 2.71 (ddd, J=1.6, 9.6, 11.2 Hz, 1H).

Compound 45: (S)-2-(4-(5-(3,5-difluorophenyl)-4,5-dihydro-1H-pyrazole-1-carbonyl)piperazin-1-yl)-N-(2-morpholinoethyl)pyrimidine-4-carboxamide

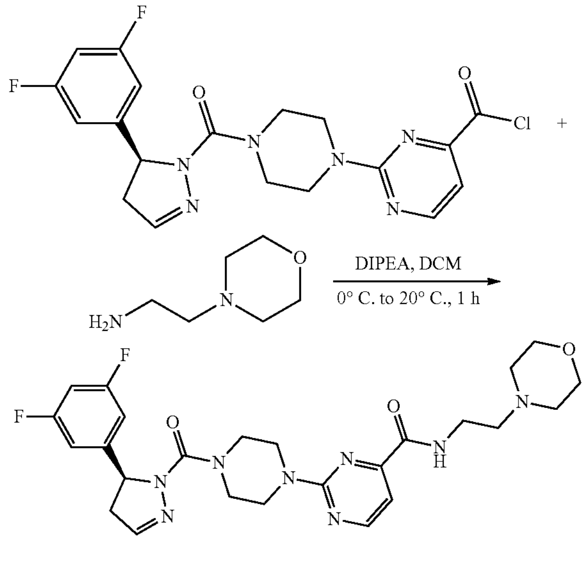

The titled compound 45 was prepared in 32.2% yield from (S)-2-(4-(5-(3,5-difluorophenyl)-4,5-dihydro-1H-pyrazole-1-carbonyl)piperazin-1-yl)pyrimidine-4-carboxylic acid according to the procedure outlined for compound 2. Mass (ESI): m/z calcd for $C_{25}H_{30}F_2N_8O_3$ 528.6, found 529.7 [M+H]$^+$. $^1$H NMR (400 MHz, $CDCl_3$) δ (ppm): δ 8.69 (t, J=1.2 Hz, 1H), 8.52 (d, J=4.8 Hz, 1H), 7.18 (d, J=4.8 Hz, 1H), 6.85 (t, J=1.6 Hz, 1H), 6.77-6.82 (m, 2H), 6.67-6.73 (m, 1H), 5.31 (dd, J=9.6, 11.6 Hz, 1H), 3.78-4.05 (m, 10H), 3.58-3.77 (m, 6H), 3.49 (t, J=5.6 Hz, 2H), 3.32 (ddd, J=2.0, 12.0, 13.2 Hz, 1H), 2.92-3.05 (m, 2H), 2.68 (ddd, J=1.6, 9.6, 11.2 Hz, 1H).

Compound 46: (S)-2-(4-(5-(3,5-difluorophenyl)-4,5-dihydro-1H-pyrazole-1-carbonyl)piperazin-1-yl)-N-methylpyrimidine-4-carboxamide

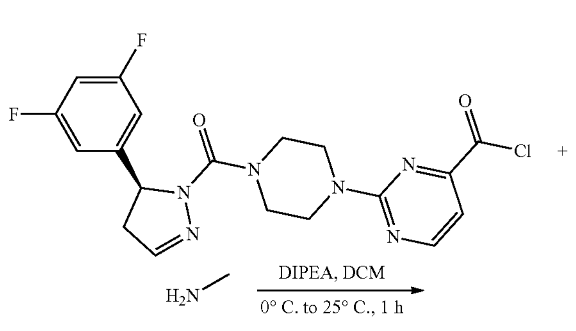

-continued

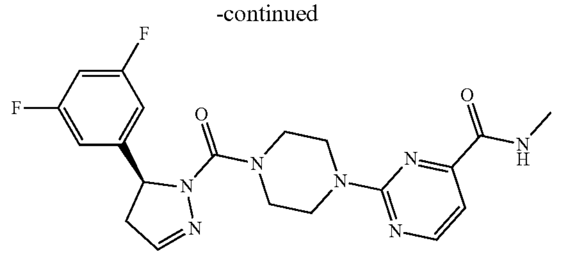

The titled compound 46 was prepared in 30.4% yield from (S)-2-(4-(5-(3,5-difluorophenyl)-4,5-dihydro-1H-pyrazole-1-carbonyl)piperazin-1-yl)pyrimidine-4-carboxylic acid according to the procedure outlined for compound 2. Mass (ESI): m/z calcd for $C_{20}H_{21}F_2N_7O_2$ 429.4, found 430.3 [M+H]$^+$. $^1$H NMR (400 MHz, $CDCl_3$) δ (ppm): δ 8.51 (d, J=4.8 Hz, 1H), 7.74 (d, J=4.4 Hz, 1H), 7.30 (d, J=4.8 Hz, 1H), 6.79-6.85 (m, 3H), 6.66-6.71 (m, 1H), 5.32 (dd, J=10.0, 11.6 Hz, 1H), 3.89-3.96 (m, 2H), 3.74-3.85 (m, 4H), 3.61-3.68 (m, 2H), 3.31 (ddd, J=2.0, 11.6, 13.6 Hz, 1H), 3.00 (d, J=4.2 Hz, 3H), 2.68 (ddd, J=1.6, 9.6, 11.2 Hz, 1H).

Compound 47: (S)-2-(4-(5-(3,5-difluorophenyl)-4,5-dihydro-1H-pyrazole-1-carbonyl)piperazin-1-yl)-5-fluoropyrimidine-4-carboxylate

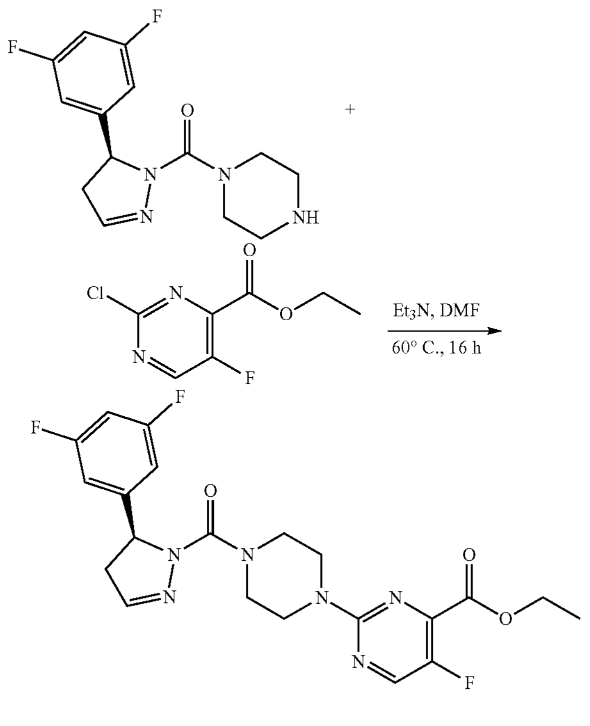

(S)-(5-(3,5-difluorophenyl)-4,5-dihydro-1H-pyrazol-1-yl)(piperazin-1-yl)methanone (6 mg, 0.204 mmoL) and ethyl 2-chloro-5-fluoropyrimidine-4-carboxylate (38.9 mg, 0.19 mmoL) were dissolved in 11.7 mL DMF. TEA (59 ul) was added. Let it stir at 60° C. under nitrogen for 16 hrs. The solvent was evaporated to dryness and purified by Prep-TLC (PE/EA=1/2) to give 20 mg of 47 as a light yellow solid. Yield: 21.2%. Mass (ESI): m/z calcd for $C_{21}H_{21}F_3N_6O_3$ 462.4, found 463.3 [M+H]. $^1$H NMR (400 MHz, $CDCl_3$) δ (ppm): δ 8.34 (d, J=2.0 Hz, 1H), 6.78-6.85 (m, 3H), 6.66-

6.71 (m, 1H), 5.32 (dd, J=10.0, 11.2 Hz, 1H), 4.43 (q, J=7.2 Hz, 2H), 3.86-3.91 (m, 2H), 3.72-3.81 (m, 4H), 3.59-3.65 (m, 2H), 3.30 (ddd, J=1.6, 11.6, 13.6 Hz, 1H), 2.68 (ddd, J=1.6, 10.0, 11.6 Hz, 1H), 1.40 (t, J=7.2 Hz, 3H).

Compound 48: (S)-2-(4-(5-(3,5-difluorophenyl)-4,5-dihydro-1H-pyrazole-1-carbonyl)piperazin-1-yl)-5-fluoropyrimidine-4-carboxamide

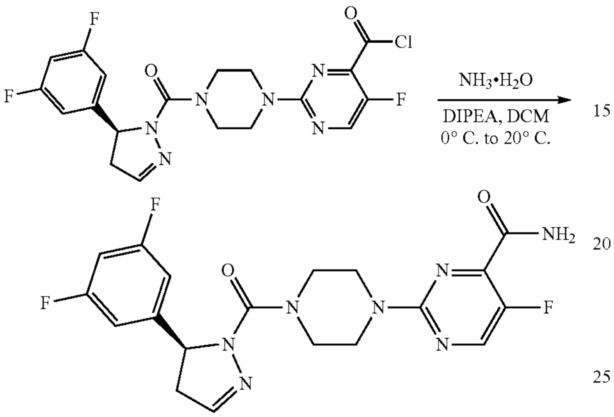

The titled compound 48 was prepared in 66.67% yield from ammonium hydroxide and (S)-2-(4-(5-(3,5-difluorophenyl)-4,5-dihydro-1H-pyrazole-1-carbonyl) iperazin-1-yl)-5-fluoropyrimidine-4-carbonyl chloride according to the procedure outlined for compound 2. Mass (ESI): m/z calcd for C19H18F3N7O2 433.4, found 434.3 $[M+H]^+$. $^1H$ NMR (400 MHz, $CDCl_3$) δ (ppm): δ 8.40 (d, J=3.2 Hz, 1H), 7.37 (brs, 1H), 6.80-6.86 (m, 3H), 6.67-6.72 (m, 1H), 5.90 (brs, 1H), 5.33 (dd, J=10.0, 11.6 Hz, 1H), 3.86-3.91 (m, 2H), 3.74-3.81 (m, 4H), 3.63-3.67 (m, 2H), 3.32 (ddd, J=1.6, 11.6, 13.6 Hz, 1H), 2.69 (ddd, J=1.6, 10.0, 11.2 Hz, 1H).

Compound 49: methyl (S)-2-(4-(5-(3,5-difluorophenyl)-4,5-dihydro-1H-pyrazole-1-carbonyl)piperazin-1-yl)pyrimidine-4-carboxylate

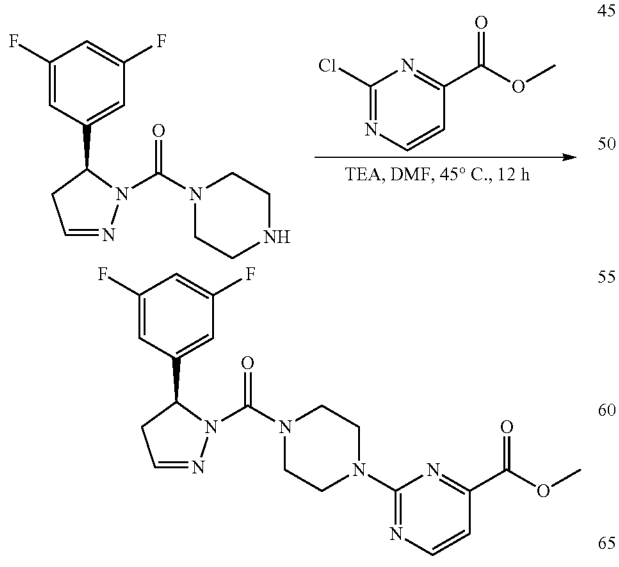

To a solution of (S)-(5-(3,5-difluorophenyl)-4,5-dihydro-1H-pyrazol-1-yl)(piperazin-1-yl)methanone (500 mg, 1.7 mmol) in DMF (5 mL) methyl 2-chloropyrimidine-4-carboxylate (350 mg, 2.0 mmol) and $Et_3N$ (0.7 mL, 5.1 mmol). The resulting mixture was stirred for 12 h at 45° C. After cooled to room temperature. The reaction mixture was poured into water (50 ml) and then extracted with DCM (3×50 ml). The organic layers were combined, dried over anhydrous sodium sulfate, filtered and concentrated under vacuum. The residue was purified by silica gel chromatography (eluting with ethyl acetate/petroleum ether=1:1) to give the titled compound as a white solid (500 mg, 68%). Yield: 68%. LCMS (ES, m/z): 431.16$[M+H]^+$. $^1H$ NMR (400 MHz, $CDCl_3$) δ 8.51 (d, J=4.8 Hz, 1H), 7.15 (d, J=4.8 Hz, 1H), 6.91-6.78 (m, 2H), 6.72-6.65 (m, 1H), 5.33 (dd, J=11.6, 9.9 Hz, 1H), 4.06-3.97 (m, 2H), 3.96 (s, 3H), 3.88 (ddd, J=13.2, 7.2, 3.4 Hz, 2H), 3.83-3.69 (m, 2H), 3.64 (ddd, J=13.2, 6.6, 3.4 Hz, 2H), 3.32 (ddd, J=18.2, 11.7, 1.8 Hz, 1H), 2.69 (ddd, J=18.4, 9.8, 1.6 Hz, 1H).

Compound 50: (S)-(5-(3,5-difluorophenyl)-4,5-dihydro-1H-pyrazol-1-yl)(4-(5-fluoro-4-(3-hydroxy-3-methylazetidine-1-carbonyl)pyrimidin-2-yl)piperazin-1-yl)methanone

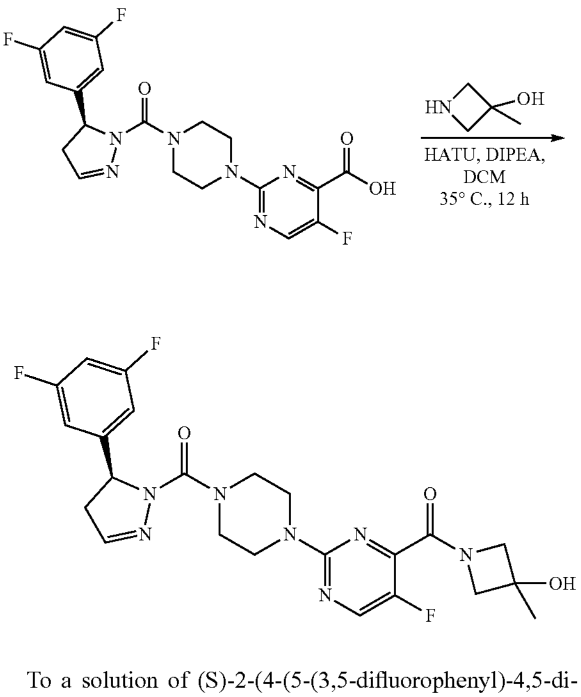

To a solution of (S)-2-(4-(5-(3,5-difluorophenyl)-4,5-dihydro-1H-pyrazole-1-carbonyl)piperazin-1-yl)-5-fluoropyrimidine-4-carboxylic acid (50 mg, 115.1 umol) in DCM (3 mL) was added HATU (66 mg, 172.7 umol), DIPEA (25 mg, 172.7 umol) and 3-methylazetidin-3-ol (22 mg, 172.7 umol). The reaction mixture was stirred at 35° C. for 12 h. The crude was purified by reversed-phase chromatography. The titled compound 50 (26 mg) was obtained as a yellow solid, Yield: 44.9%. LC-MS (m/z) 504.1 $(M+H^+)$. $^1H$ NMR (400 MHz, $CDCl_3$) δ 8.31 (d, J=0.7 Hz, 1H), 6.89-6.77 (m, 3H), 6.70 (tt, J=8.9, 2.4 Hz, 1H), 5.37-5.30 (m, 1H), 4.32 (d, J=10.0 Hz, 1H), 4.18 (dd, J=9.9, 6.4 Hz, 1H), 4.13 (s, 2H), 3.91-3.56 (m, 8H), 3.33 (ddd, J=18.3, 11.8, 1.8 Hz, 1H), 2.69 (ddd, J=18.3, 9.8, 1.6 Hz, 1H), 1.57 (s, 3H).

Compound 51: (S)-3-fluoro-5-(1-(4-(5-fluoro-4-(3-methoxyazetidine-1-carbonyl)pyrimidin-2-yl)piperazine-1-carbonyl)-4,5-dihydro-1H-pyrazol-5-yl)benzonitrile

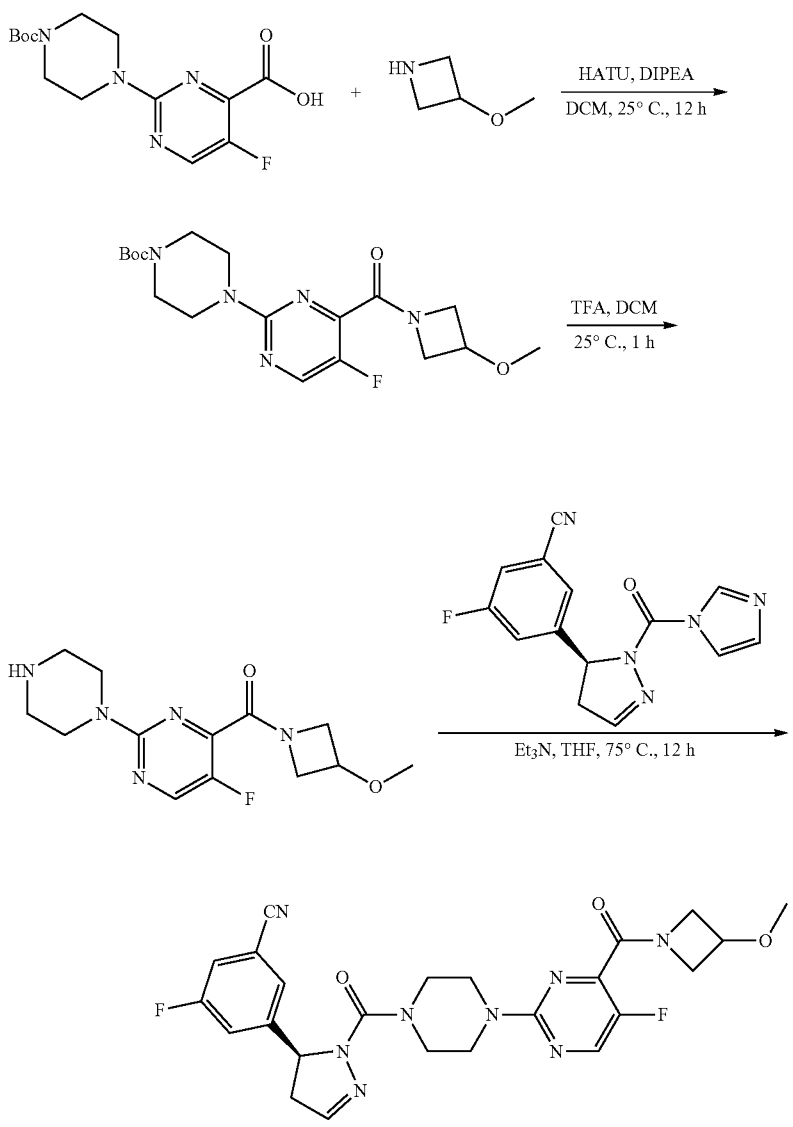

Step 1: To a solution of 2-(4-(tert-butoxycarbonyl)piperazin-1-yl)-5-fluoropyrimidine-4-carboxylic acid (300 mg, 919.3 umol) in DCM (10 mL) was added DIPEA (328 mg, 2.76 mmol), HATU (525 mg, 1.38 mmol) and 3-methoxyazetidine (124 mg, 1.01 mmol). The reaction mixture was stirred at 25° C. for 12 h. The mixture was purified by Flash chromatography. tert-butyl 4-(5-fluoro-4-(3-methoxyazetidine-1-carbonyl)pyrimidin-2-yl)piperazine-1-carboxylate was obtained as a yellow solid (310 mg, 85.3%). LC-MS (m/z) 396.2 ($M+H^+$).

Step 2: To a solution of tert-butyl 4-(5-fluoro-4-(3-methoxyazetidine-1-carbonyl)pyrimidin-2-yl)piperazine-1-carboxylate (100 mg, 252.89 umol) in DCM (10 mL) was added TFA (5 mL). The reaction mixture was stirred at 25° C. for 1 h. The mixture was concentrated under vacuum and used to next step directly. LC-MS (m/z) 296.1 ($M+H^+$).

Step 3: To a solution of compound (5-fluoro-2-(piperazin-1-yl)pyrimidin-4-yl)(3-methoxyazetidin-1-yl)methanone (52 mg, 172.5 umol) in THF (6 mL) was added (S)-3-(1-(1H-imidazole-1-carbonyl)-4,5-dihydro-1H-pyrazol-5-yl)-5-fluorobenzonitrile (50 mg, 172.5 umol) and $Et_3N$ (2 mL). The reaction mixture was stirred at 75° C. for 12 h. The crude was purified by reversed-phase chromatography. The titled compound 51 (63 mg) was obtained as a yellow solid, Yield: 69.9%. LC-MS (m/z) 511.1 ($M+H^+$). $^1H$ NMR (400 MHz, $CDCl_3$) δ 8.27 (d, J=1.9 Hz, 1H), 7.34 (t, J=1.5 Hz, 1H), 7.24-7.14 (m, 2H), 6.84 (d, J=1.6 Hz, 1H), 5.60 (brs, 1H), 5.31 (dd, J=11.6, 9.8 Hz, 1H), 4.44-4.40 (m, 1H), 4.33 (dd, J=11.2, 5.5 Hz, 1H), 4.26-4.11 (m, 2H), 4.05-4.01 (m, 1H), 3.87-3.50 (m, 8H), 3.35-3.28 (m, 1H), 3.26 (s, 3H), 2.64 (ddd, J=18.4, 9.7, 1.6 Hz, 1H).

Compound 52: (S)-(5-fluoro-2-(4-(5-(5-fluoropyridin-3-yl)-4,5-dihydro-1H-pyrazole-1-carbonyl)piperazin-1-yl)pyrimidin-4-yl)(3-methoxyazetidin-1-yl)methanone

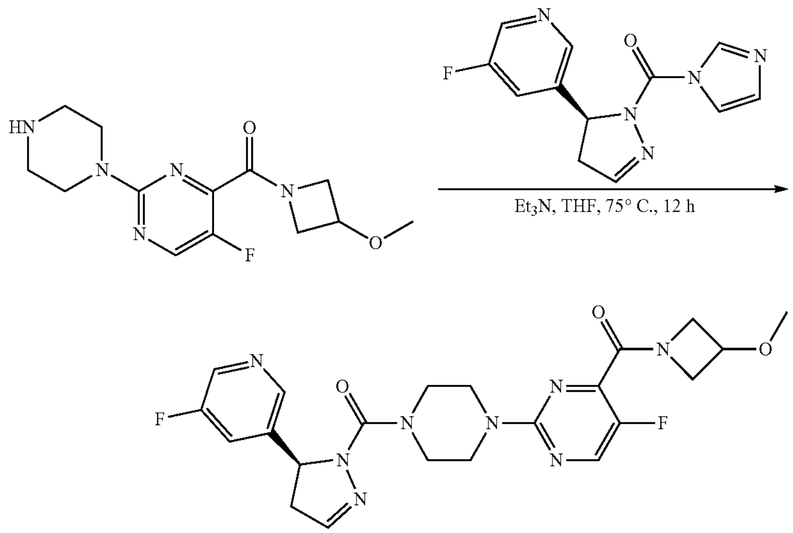 [SMILES: COC1CN(C(=O)c2nc(N3CCNCC3)ncc2F)C1 ; O=C(N1N=CC[C@H]1c1cncc(F)c1)n1ccnc1 ; COC1CN(C(=O)c2nc(N3CCN(C(=O)N4N=CC[C@H]4c4cncc(F)c4)CC3)ncc2F)C1]

The titled compound 52 was prepared from (5-fluoro-2-(piperazin-1-yl)pyrimidin-4-yl)(3-methoxyazetidin-1-yl) methanone according to the procedure outlined for compound 51. LC-MS (m/z) 487.1 ($M+H^+$). $^1H$ NMR (400 MHz, $CDCl_3$) δ 8.43 (s, 1H), 8.39 (dd, J=2.8, 0.9 Hz, 1H), 8.32 (dd, J=2.1, 1.0 Hz, 1H), 7.34 (dt, J=9.1, 2.6 Hz, 1H), 6.90 (s, 1H), 5.41 (t, J=10.9 Hz, 1H), 4.51-4.41 (m, 1H), 4.42-4.32 (m, 1H), 4.32-4.19 (m, 1H), 4.13-4.03 (m, 1H), 3.91-3.56 (m, 8H), 3.38 (ddt, J=18.3, 10.3, 1.3 Hz, 1H), 3.32 (s, 3H), 2.75 (ddt, J=18.3, 10.3, 1.3 Hz, 1H).

Compound 53: (S)-5-(1-(4-(5-fluoro-4-(3-methoxyazetidine-1-carbonyl)pyrimidin-2-yl)piperazine-1-carbonyl)-4,5-dihydro-1H-pyrazol-5-yl)nicotinonitrile

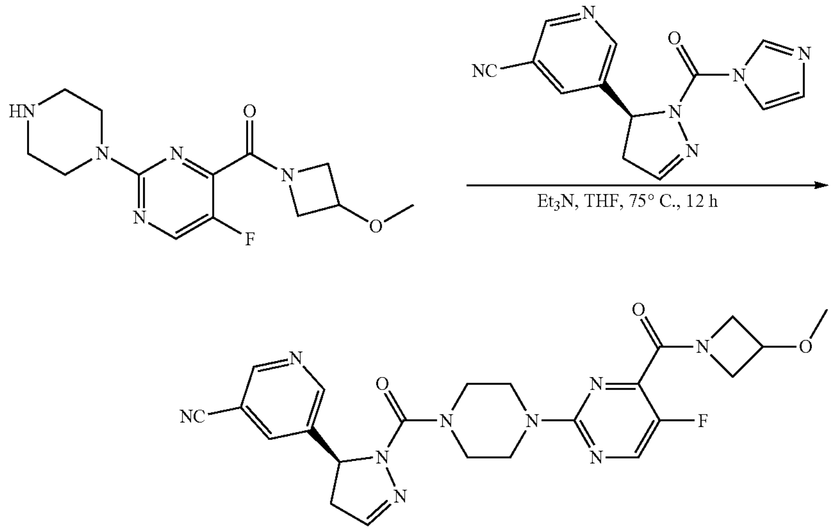

The titled compound 53 was prepared from (5-fluoro-2-(piperazin-1-yl)pyrimidin-4-yl)(3-methoxyazetidin-1-yl) methanone according to the procedure outlined for compound 51. LC-MS (m/z) 494.1 (M+H$^+$). $^1$H NMR (400 MHz, $CDCl_3$) δ 8.83-8.77 (m, 2H), 8.32 (dd, J=1.9, 0.7 Hz, 1H), 7.91 (t, J=2.2 Hz, 1H), 6.94 (s, 1H), 5.42 (t, J=10.9 Hz, 1H), 4.46 (ddd, J=10.4, 5.3, 3.1 Hz, 1H), 4.42-4.34 (m, 1H), 4.33-4.18 (m, 2H), 4.08 (ddd, J=11.2, 3.8, 1.3 Hz, 1H), 3.91-3.58 (m, 8H), 3.47-3.35 (m, 1H), 3.32 (s, 3H), 2.81-2.68 (m, 1H).

Compound 54: (S)-1-(2-(4-(5-(3-cyano-5-fluorophenyl)-4,5-dihydro-1H-pyrazole-1-carbonyl)piperazin-1-yl)-5-fluoropyrimidine-4-carbonyl)azetidine-3-carbonitrile

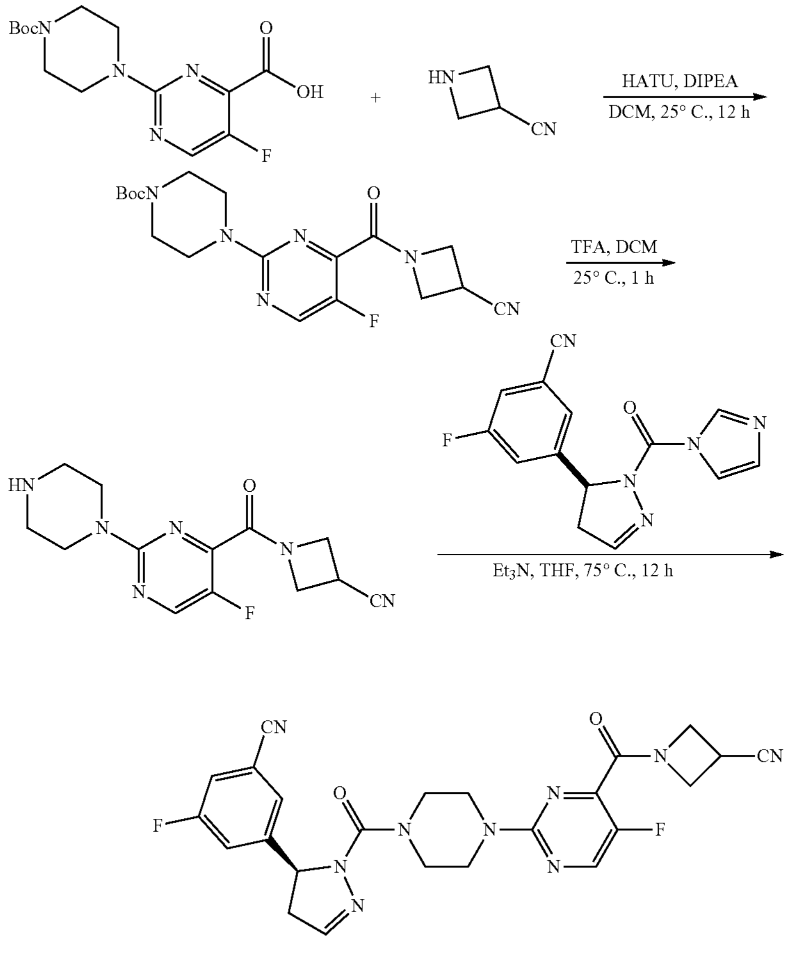

The titled compound 54 was prepared according to the procedure outlined for compound 51. LC-MS (m/z) 506.1 (M+H$^+$). $^1$H NMR (400 MHz, $CDCl_3$) δ 8.31 (d, J=2.2 Hz, 1H), 7.33-7.32 (m, 1H), 7.21 (d, J=1.4 Hz, 1H), 7.19-7.18 (m, 2H), 6.85 (s, 1H), 6.31 (brs, 1H), 5.31 (dd, J=11.7, 9.6 Hz, 1H), 4.67 (dd, J=7.5, 4.3 Hz, 2H), 4.46 (t, J=9.9 Hz, 1H), 4.38 (dd, J=10.6, 6.1 Hz, 1H), 3.85-3.47 (m, 8H), 3.39-3.25 (m, 1H), 2.64 (ddd, J=18.4, 9.6, 1.5 Hz, 1H).

Compound 55: (S)-(5-(3,5-difluorophenyl)-4,5-dihydro-1H-pyrazol-1-yl)(4-(5-fluoro-4-(3-methyleneazetidine-1-carbonyl)pyrimidin-2-yl)piperazin-1-yl)methanone

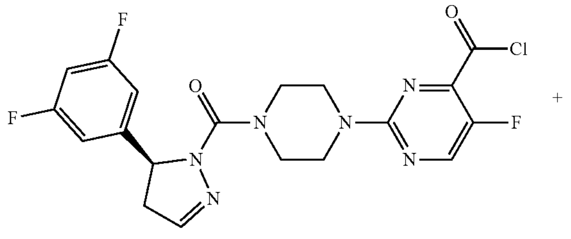

-continued

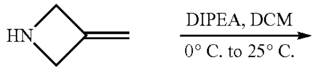

-continued

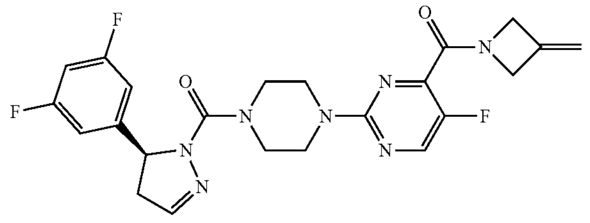

The titled compound 55 was prepared in 69.2% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 486.1 (M+H$^+$). $^1$H NMR (400 MHz, DMSO-$d_6$) δ 8.61 (d, J=2.3 Hz, 1H), 7.14-7.07 (m, 2H), 7.05-6.94 (m, 2H), 5.26 (dd, J=11.5, 10.0 Hz, 1H), 5.10 (dt, J=7.8, 2.6 Hz, 2H), 4.92-4.89 (m, 2H), 4.65-4.63 (m, 2H), 3.79-3.47 (m, 8H), 3.36 (ddd, J=18.3, 11.6, 1.9 Hz, 1H), 2.64 (ddd, J=18.3, 10.0, 1.6 Hz, 1H).

Compound 56: (S)-(5-(3,5-difluorophenyl)-4,5-dihydro-1H-pyrazol-1-yl)(4-(5-fluoro-4-(3-methylazetidine-1-carbonyl)pyrimidin-2-yl)piperazin-1-yl)methanone

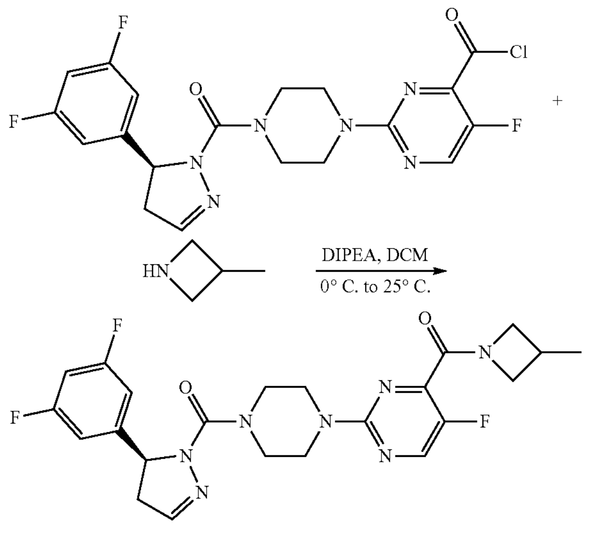

The titled compound 56 was prepared in 72.5% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 488.1 (M+H$^+$). $^1$H NMR (400 MHz, $CDCl_3$) δ 8.59 (d, J=5.9 Hz, 1H), 7.17 (d, J=5.9 Hz, 1H), 7.09 (t, J=6.4 Hz, 2H), 7.00-6.94 (m, 1H), 5.54 (td, J=11.0, 6.3 Hz, 1H), 4.67 (t, J=8.1 Hz, 1H), 4.50 (d, J=8.5 Hz, 1H), 4.18-3.75 (m, 10H), 3.61 (ddd, J=18.2, 11.7, 6.0 Hz, 1H), 3.09-3.02 (m, 1H), 2.97-2.88 (dt, J=17.6, 8.1 Hz, 1H), 2.85-2.78 (m, 1H), 1.52 (s, 3H).

Compound 57: (S)-2-(1-(2-(4-(5-(3,5-difluorophenyl)-4,5-dihydro-1H-pyrazole-1-carbonyl)piperazin-1-yl)-5-fluoropyrimidine-4-carbonyl)azetidin-3-ylidene)acetonitrile

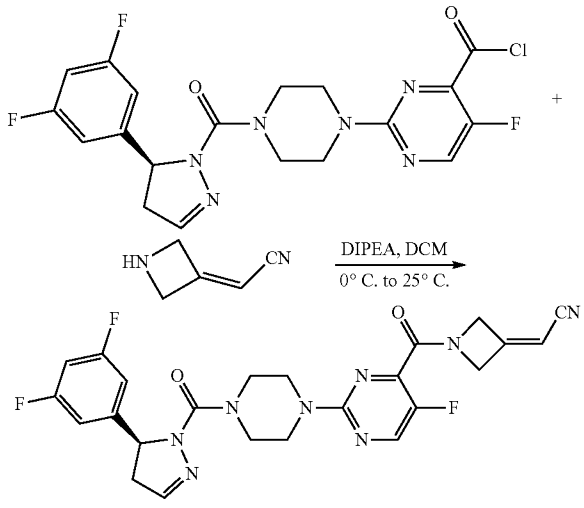

The titled compound 57 was prepared in 63.7% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 511.1 (M+H$^+$). $^1$H NMR (400 MHz, DMSO-$d_6$) δ 8.64 (t, J=1.9 Hz, 1H), 7.16-7.05 (m, 2H), 7.04-6.94 (m, 2H), 5.94-5.89 (m, 1H), 5.26 (t, J=10.7 Hz, 1H), 5.21-5.18 (m, 1H), 5.16-5.13 (m, 1H), 4.91-4.88 (m, 1H), 4.83-4.81 (m, 1H), 3.80-3.48 (m, 8H), 3.36 (ddd, J=18.3, 11.6, 1.8 Hz, 1H), 2.65 (ddd, J=18.3, 9.9, 1.6 Hz, 1H).

Compound 58: (S)-2-(1-(2-(4-(5-(3,5-difluorophenyl)-4,5-dihydro-1H-pyrazole-1-carbonyl)piperazin-1-yl)-5-fluoropyrimidine-4-carbonyl)azetidin-3-yl)acetonitrile

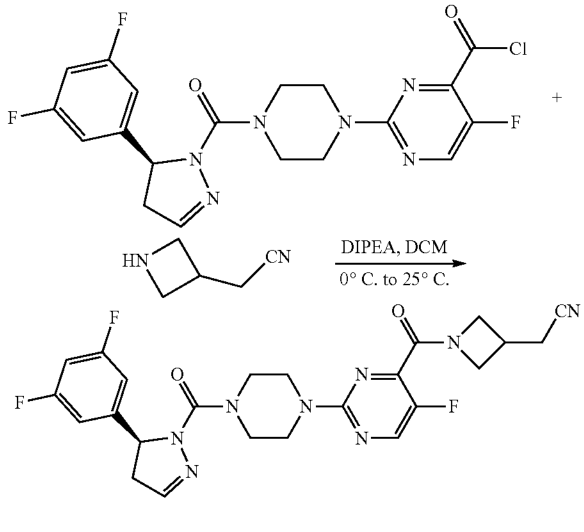

The titled compound 58 was prepared in 62.1% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 513.1 ($M+H^+$). $^1H$ NMR (400 MHz, DMSO-$d_6$) δ 8.61 (d, J=2.2 Hz, 1H), 7.18-7.05 (m, 2H), 7.02-6.97 (m, 2H), 5.25 (dd, J=11.5, 9.9 Hz, 1H), 4.46 (ddd, J=10.5, 8.6, 3.1 Hz, 1H), 4.20 (dd, J=10.4, 8.3 Hz, 1H), 4.10-4.01 (m, 1H), 3.84-3.59 (m, 7H), 3.59-3.49 (m, 2H), 3.36 (ddd, J=18.3, 11.6, 1.8 Hz, 1H), 3.01-2.96 (m, 1H), 2.89 (d, J=6.4 Hz, 2H), 2.64 (ddd, J=18.4, 9.9, 1.6 Hz, 1H).

Compound 59: (S)-3-(1-(4-(4-(3-(cyclopropylmethoxy)azetidine-1-carbonyl)-5-fluoropyrimidin-2-yl)piperazine-1-carbonyl)-4,5-dihydro-1H-pyrazol-5-yl)-5-fluorobenzo nitrile

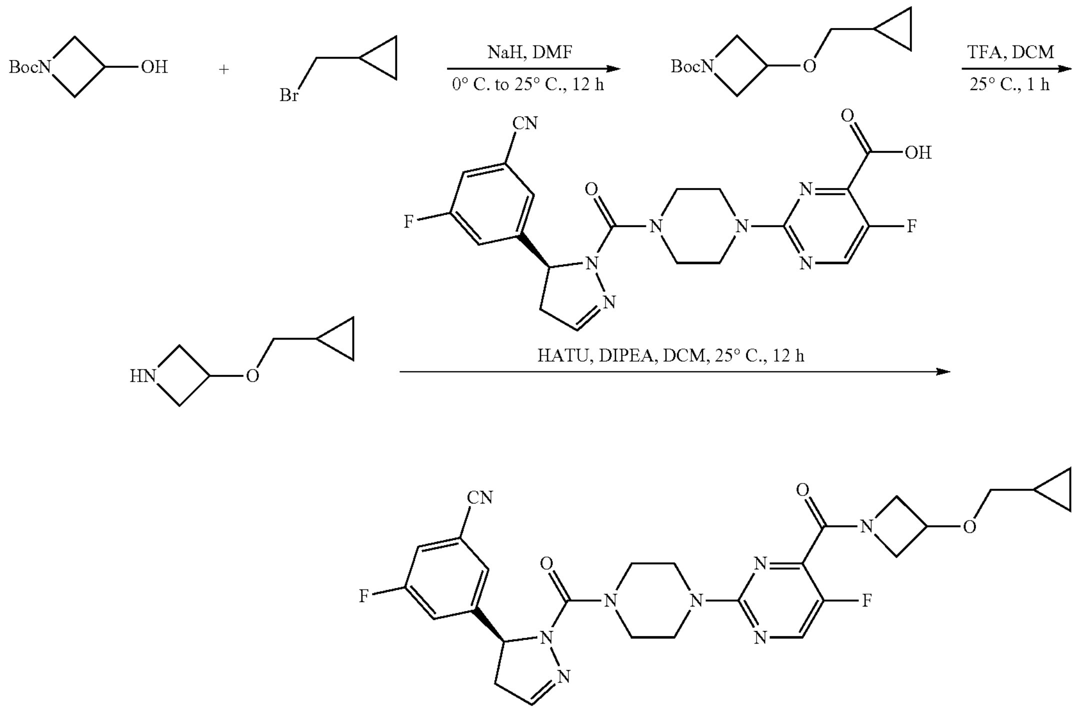

Step 1: Add NaH (60% in oil, 900 mg, 22.5 mmol) to a solution of tert-butyl 3-hydroxyazetidine-1-carboxylate (3 g, 17.32 mmol) in DMF (10 mL) at 0° C. Stir the mixture at RT for 1.5 h, then slowly add bromomethylcyclopropane (2.80 g, 20.7 mmol) and stir over 12 hr. Dilute the mixture with EtOAc, wash twice with $H_2O$, once with saturated aqueous NaCl, separate the layers, dry the organic extract over $Na_2SO_4$, filter, and concentrate the filtrate in vacuo, subject the resulting residue to chromatography on silica, eluting with a gradient of 0-20% EtOAc in hexanes to give the title compound (1.7 g) as colorless oil after solvent evaporation, Yield: 43.2%. LC-MS (m/z) 228.1 ($M+H^+$).

Step 2: To a solution of tert-butyl 3-(cyclopropylmethoxy) azetidine-1-carboxylate (300 mg, 1.32 mmol) in DCM (5 mL) was added TFA (5 mL). The reaction mixture was stirred at 25° C. for 1 h. The crude was concentrated under vacuum and used to next step directly. LC-MS (m/z) 128.1 ($M+H^+$).

Step 3: The titled compound 59 (S)-3-(1-(4-(4-(3-(cyclopropylmethoxy)azetidine-1-carbonyl)-5-fluoropyrimidin-2-yl)piperazine-1-carbonyl)-4,5-dihydro-1H-pyrazol-5-yl)-5-fluorobenzonitrile was prepared in 36.2% yield from 3-(cyclopropylmethoxy)azetidine according to the procedure outlined for compound 2. LC-MS (m/z) 551.1 ($M+H^+$). $^1H$ NMR (400 MHz, DMSO-$d_6$) δ 8.61 (d, J=2.2 Hz, 1H), 7.78-7.68 (m, 1H), 7.64 (s, 1H), 7.56-7.44 (m, 1H), 7.11 (s, 1H), 5.29 (t, J=10.9 Hz, 1H), 4.51-4.42 (m, 1H), 4.39-4.34 (m, 1H), 4.30-4.21 (m, 1H), 4.14-4.07 (m, 1H), 3.86 (ddd, J=11.0, 3.9, 1.4 Hz, 1H), 3.79-3.48 (m, 9H), 3.22 (d, J=6.9 Hz, 2H), 1.21-1.13 (m, 1H), 0.51-0.43 (m, 2H), 0.20-0.13 (m, 2H).

Compound 60: (S)-(5-(3,5-difluorophenyl)-4,5-dihydro-1H-pyrazol-1-yl)(4-(5-fluoro-4-(3-(trifluoromethoxy)azetidine-1-carbonyl)pyrimidin-2-yl)piperazin-1-yl)methanone

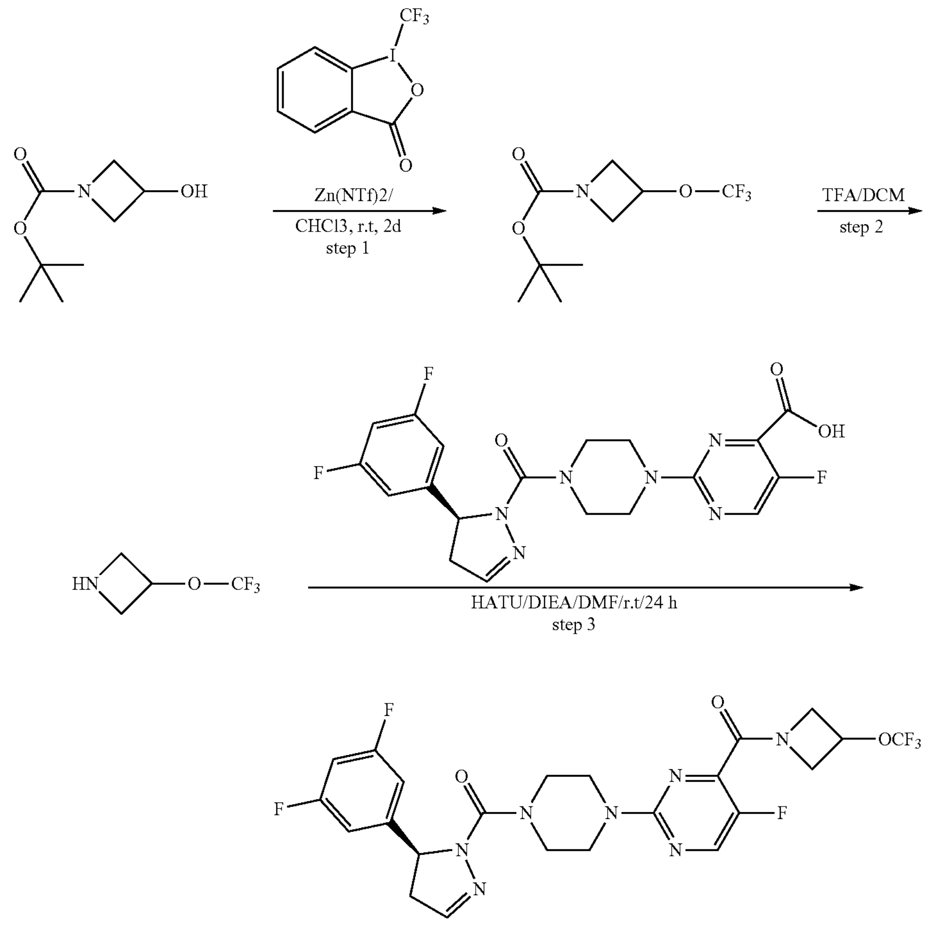

Step 1: tert-butyl 3-hydroxyazetidine-1-carboxylate (2.189 g, 12.653 mmol) and $Zn(NTf)_2$ (537.1 mg, 0.837 mmol) and 1-(trifluoromethyl)-113-benzo[d][1,2]iodaoxol-3(1H)-one (800 mg, 2.532 mmol) were dissolved in 16.9 mml $CHCl_3$. Let it stir at room temperature for 48 hrs. The solvent was evaporated to dryness and purified by column chromatography (PE/EA=10/1) to give 45 mg tert-butyl 3-(trifluoromethoxy)azetidine-1-carboxylate as yellow oil. LC-MS (m/z): 242.1$[M+H]^+$.

Step 2 and Step 3: tert-butyl 3-(trifluoromethoxy)azetidine-1-carboxylate (45 mg, 0.186 mmol) was dissolved in 1 mL DCM. 0.2 mL of TFA/DCM (1/1) was added to the solution at 0° C. Let it stir at r.t for 1 h. The solvent was evaporated to dryness and used for next step without further purification. LC-MS (m/z): 142.2$[M+H]^+$.

The above residue and (S)-2-(4-(5-(3,5-difluorophenyl)-4,5-dihydro-1H-pyrazole-1-carbonyl)piperazin-1-yl)-5-fluoropyrimidine-4-carboxylic acid (10 mg, 0.02 mmol) and HATU (11.6 mg, 0.03 mmol) and 0.1 ml of TEA were dissolved in 2 mL DMF. Let it stir at room temperature for 16 hrs. 1 mL water was added to the solution and extracted with EtOAc (5 mL×3). The organic layers were combined and evaporated to dryness and purified by prep-HPLC to give 3 mg of (S)-(5-(3,5-difluorophenyl)-4,5-dihydro-1H-pyrazol-1-yl)(4-(5-fluoro-4-(3-(trifluoromethoxy)azetidine-1-carbonyl)pyrimidin-2-yl)piperazin-1-yl)methanone as white solid. Total yield of two steps: 27%. $^1H$ NMR (400 MHz, $CDCl_3$) δ (ppm): 8.35 (d, J=2.4 Hz, 1H), 6.86 (t, J=1.6 Hz, 1H), 6.83-6.81 (m, 1H), 6.70 (tt, J=8.8, 2.0 Hz, 1H), 5.33 (dd, J=11.2, 10.0 Hz, 1H), 5.06-5.00 (m, 1H), 3.89-3.82 (m, 3H), 3.81-3.70 (m, 6H), 3.68-3.57 (m, 3H), 3.33 (ddd, J=18.4, 12.0, 1.6 Hz, 1H), 2.69 (ddd, J=18.4, 10.0, 1.6 Hz, 1H). LC-MS (m/z): 558.2 $[M+H]^+$.

Compound 61: (S)-(5-(3,5-difluorophenyl)-4,5-dihydro-1H-pyrazol-1-yl)(4-(4-(2,5-dihydro-1H-pyrrole-1-carbonyl)-5-fluoropyrimidin-2-yl)piperazin-1-yl)methanone

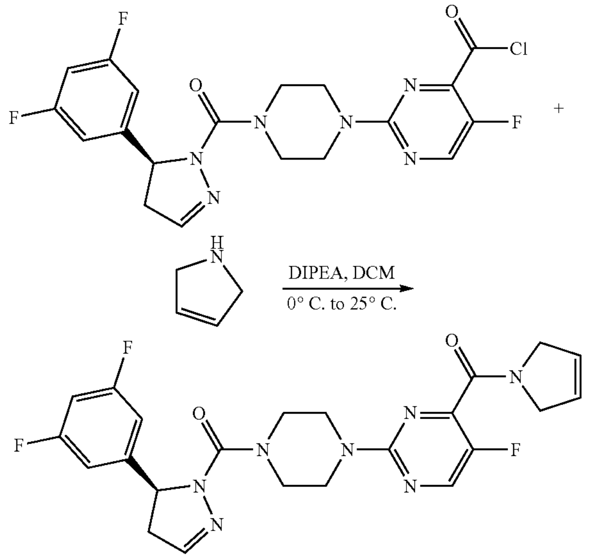

The titled compound 61 was prepared in 55.7% yield from (S)-2-(4-(5-(3,5-difluorophenyl)-4,5-dihydro-1H-pyrazole-1-carbonyl)piperazin-1-yl)-5-fluoropyrimidine-4-carbonyl chloride according to the procedure outlined for compound 2. LC-MS (m/z) 486.1 ($M+H^+$). $^1H$ NMR (400 MHz, DMSO-$d_6$) δ 8.62 (d, J=1.5 Hz, 1H), 7.15-7.05 (m, 2H), 7.02-6.97 (m, 2H), 5.97-5.94 (m, 1H), 5.88-5.85 (m, 1H), 5.25 (dd, J=11.5, 10.0 Hz, 1H), 4.29-4.21 (m, 4H), 3.80-3.48 (m, 8H), 3.36 (ddd, J=18.3, 11.6, 1.9 Hz, 1H), 2.64 (ddd, J=18.3, 10.0, 1.6 Hz, 1H).

Compound 62: (S)-2-(4-(5-(3,5-difluorophenyl)-4,5-dihydro-1H-pyrazole-1-carbonyl)piperazin-1-yl)-5-methoxypyrimidine-4-carboxamide

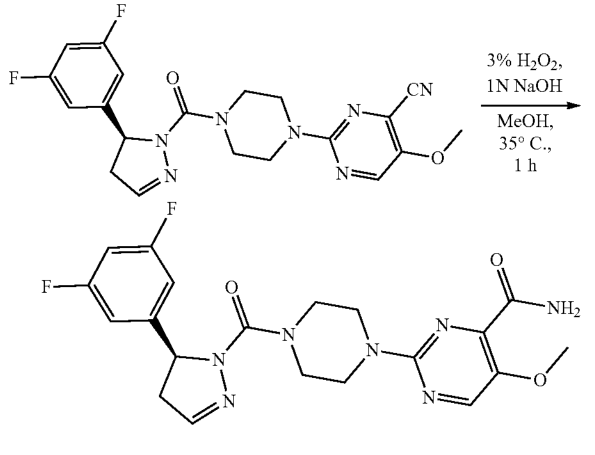

The titled compound 62 was prepared according to the procedure outlined for compound 67. H NMR (400 MHz, $CDCl_3$) δ 8.35 (s, 1H), 7.39 (brs, 1H), 6.94-6.77 (m, 3H), 6.79-6.57 (m, 1H), 5.74 (brs, 1H), 5.33 (dd, J=11.7, 9.9 Hz, 1H), 3.94 (s, 3H), 3.92-3.52 (m, 8H), 3.32 (ddd, J=18.3, 11.7, 1.8 Hz, 1H), 2.69 (ddd, J=18.3, 9.9, 1.6 Hz, 1H).

Compound 63: (S)-3-(1-(4-(5-chloro-4-(3-methoxyazetidine-1-carbonyl)pyrimidin-2-yl)piperazin-1-carbonyl)-4,5-dihydro-1H-pyrazol-5-yl)-5-fluorobenzonitrile

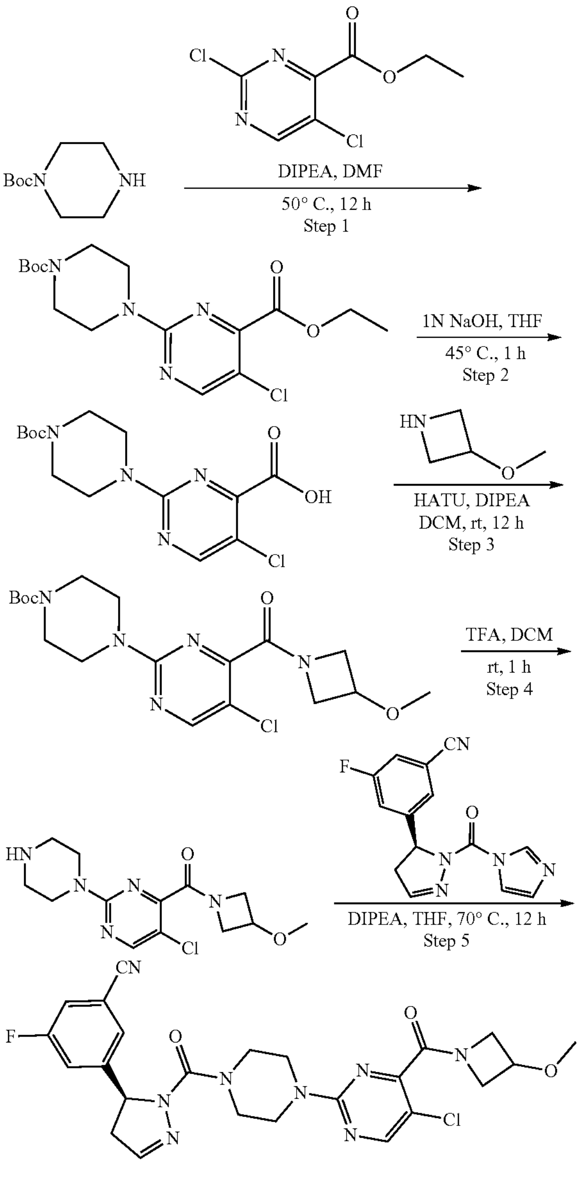

Step 1: To a solution of tert-butyl piperazine-1-carboxylate (303 mg, 1.63 mmol) in DMF (10 mL) was added ethyl 2,5-dichloropyrimidine-4-carboxylate (360 mg, 1.63 mmol) and DIPEA (315 mg, 2.44 mmol). The reaction mixture was stirred at 50° C. for 12 h. The crude was purified by column chromatography on silica gel. Ethyl 2-(4-(tert-butoxycarbonyl)piperazin-1-yl)-5-chloropyrimidine-4-carboxylate (230 mg, 38%) was obtained as a light-yellow solid MS (m/z): 371.1 $[M+H]^+$.

Step 2: To a solution of ethyl 2-(4-(tert-butoxycarbonyl) piperazin-1-yl)-5-chloropyrimidine-4-carboxylate (150 mg, 404.5 umol) in THF (6 mL) was added 1 N NaOH (6 mL). The reaction mixture was stirred at 45° C. for 1 h. Acidify the reaction mixture by adding 1 N HCl. The aqueous layer was extracted with EtOAc (100 mL) twice. The combined organic layers were washed with brine (50 mL) and dried over $Na_2SO_4$. The solvent was concentrated under vacuum. The crude was used to next step directly MS (m/z): 343.1 $[M+H]^+$.

Step 3: To a solution of 2-(4-(tert-butoxycarbonyl)piperazin-1-yl)-5-chloropyrimidine-4-carboxylic acid (100 mg, 291.7 umol) in DCM (5 mL) was added 3-methoxyazetidine (31 mg, 350.1 umol), HATU (333 mg, 875.2 umol) and DIPEA (0.5 mL). The reaction mixture was stirred at rt for 12 h. The crude was purified by column chromatography on silica gel. Tert-butyl 4-(5-chloro-4-(3-methoxyazetidine-1-carbonyl)pyrimidin-2-yl)piperazine-1-carboxylate (100 mg, 83%) was obtained as a light-yellow solid MS (m/z): 412.1 $[M+H]^+$.

Step 4: To a solution of tert-butyl 4-(5-chloro-4-(3-methoxyazetidine-1-carbonyl)pyrimidin-2-yl)piperazine-1-carboxylate (100 mg, 242.8 umol) in DCM (5 mL) was added TFA (5 mL). The reaction mixture was stirred at rt for 1 h. The solvent was concentrated under vacuum. The crude was used to next step directly MS (m/z): 312.1 $[M+H]^+$.

Step 5: To a solution of (S)-3-(1-(1H-imidazole-1-carbonyl)-4,5-dihydro-1H-pyrazol-5-yl)-5-fluorobenzonitrile (60 mg, 211.8 umol) in THF (3 mL) was added (5-chloro-2-(piperazin-1-yl)pyrimidin-4-yl)(3-methoxyazetidin-1-yl) methanone (66 mg, 211.8 umol) and DIPEA (137 mg, 1.06 mmol). The reaction mixture was stirred at 70 for 12 h. The crude was purified by Pre-HPLC. (S)-3-(1-(4-(5-chloro-4-(3-methoxyazetidine-1-carbonyl)pyrimidin-2-yl)piperazine-1-carbonyl)-4,5-dihydro-1H-pyrazol-5-yl)-5-fluorobenzonitrile (15 mg, 13%) was obtained as a light-yellow solid MS (m/z): 527.1 $[M+H]^+$. $^1$H NMR (400 MHz, DMSO) δ 8.55 (s, 1H), 7.75 (d, J=9.0 Hz, 1H), 7.21 (s, 1H), 7.12 (s, 1H), 6.66 (s, 1H), 5.34-5.22 (m, 1H), 4.35-4.15 (m, 2H), 3.95-3.35 (m, 11H), 3.36-3.28 (m, 1H), 2.90-2.84 (m, 1H).

Compound 64: (S)-(5-chloro-2-(4-(5-(5-fluoropyridin-3-yl)-4,5-dihydro-1H-pyrazole-1-carbonyl)piperazin-1-yl)pyrimidin-4-yl)(3-methoxyazetidin-1-yl) methanone

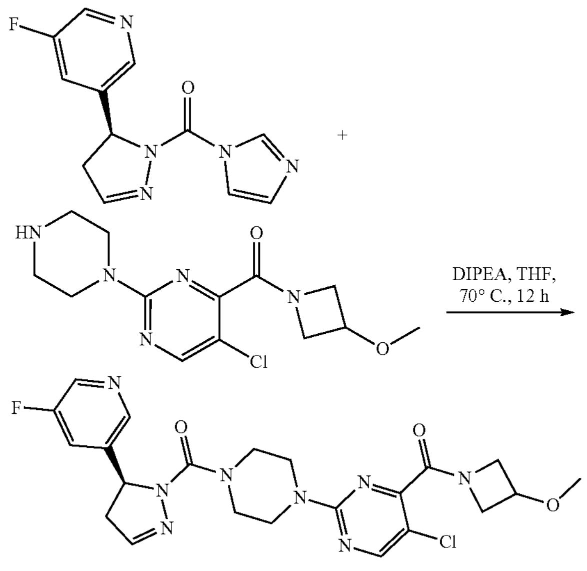

The titled compound 64 (S)-(5-chloro-2-(4-(5-(5-fluoropyridin-3-yl)-4,5-dihydro-1H-pyrazole-1-carbonyl)piperazin-1-yl)pyrimidin-4-yl)(3-methoxyazetidin-1-yl)methanone was prepared in 31% yield from (S)-(5-(5-fluoropyridin-3-yl)-4,5-dihydro-1H-pyrazol-1-yl)(1H-imidazol-1-yl)methanone according to the procedure outlined for compound 63. LC-MS (m/z) 503.1 $(M+H^+)$. $^1$H NMR (400 MHz, DMSO) δ 8.59-8.36 (m, 3H), 7.65 (d, J=9.9 Hz, 1H), 7.14 (s, 1H), 5.31 (t, J=10.9 Hz, 1H), 4.26 (d, J=9.0 Hz, 5H), 3.95-3.48 (m, 8H), 3.39 (dd, J=18.3, 11.8 Hz, 1H), 3.21 (s, 3H), 2.82-2.65 (m, 1H).

Compound 65: (5-chloro-2-(4-(5-(5-chloropyridin-3-yl)-4,5-dihydro-1H-pyrazole-1-carbonyl)piperazin-1-yl)pyrimidin-4-yl)(3-methoxyazetidin-1-yl) methanone

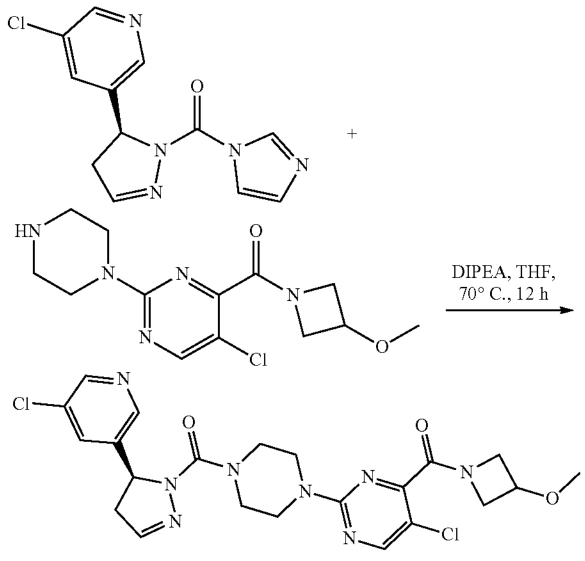

The titled compound 65 (5-chloro-2-(4-(5-(5-chloropyridin-3-yl)-4,5-dihydro-1H-pyrazole-1-carbonyl)piperazin-1-yl)pyrimidin-4-yl)(3-methoxyazetidin-1-yl)methanone was prepared in 33% yield from (5-(5-chloropyridin-3-yl)-4,5-dihydro-1H-pyrazol-1-yl)(1H-imidazol-1-yl)methanone according to the procedure outlined for compound 63. LC-MS (m/z) 519.1 $(M+H^+)$. $^1$H NMR (300 MHz, DMSO-d6) δ 8.59-8.41 (m, 2H), 8.35-8.23 (m, 1H), 7.82 (t, J=2.0 Hz, 1H), 7.13-7.11 (m, 1H), 5.25 (t, J=10.8 Hz, 1H), 4.26-4.19 (m, 3H), 3.91-3.81 (m, 1H), 3.77-3.28 (m, 8H), 3.18 (s, 3H), 3.16-3.07 (m, 2H), 2.78-2.71 (m, 1H).

Compound 66: (5-(5-chloropyridin-3-yl)-4,5-dihydro-1H-pyrazol-1-yl)(4-(5-fluoro-4-(3-methoxyazetidine-1-carbonyl)pyrimidin-2-yl)piperazin-1-yl)methanone

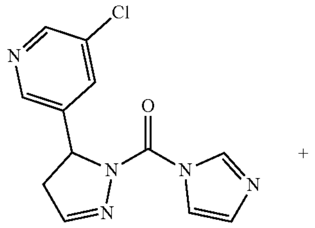

-continued

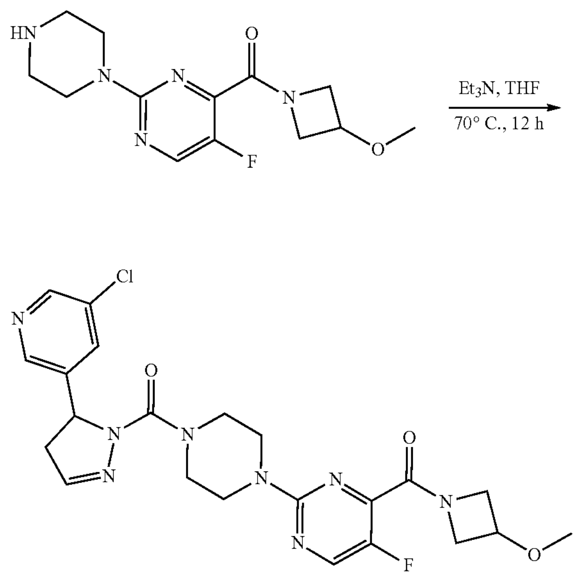

The titled compound 66 (5-(5-chloropyridin-3-yl)-4,5-dihydro-1H-pyrazol-1-yl)(4-(5-fluoro-4-(3-methoxyazetidine-1-carbonyl)pyrimidin-2-yl)piperazin-1-yl)methanone was prepared in 35% yield from (5-(5-chloropyridin-3-yl)-4,5-dihydro-1H-pyrazol-1-yl)(1H-imidazol-1-yl)methanone according to the procedure outlined for compound 63. LC-MS (m/z) 503.1 ($M+H^+$). $^1H$ NMR (300 MHz, DMSO-d6) δ 8.60-8.46 (m, 3H), 7.83 (t, J=2.1 Hz, 1H), 7.13 (d, J=1.6 Hz, 1H), 5.27 (t, J=10.8 Hz, 1H), 4.47-4.40 (m, 1H), 4.28-4.20 (m, 3H), 4.10-4.03 (m, 1H), 3.88-3.82 (m, 1H), 3.78-3.48 (m, 8H), 3.42-3.31 (m, 1H), 3.21 (s, 3H), 2.78-2.71 (m, 1H).

Compound 67: (S)-4-(4-(5-(3,5-difluorophenyl)-4,5-dihydro-1H-pyrazole-1-carbonyl)piperazin-1-yl)-5-fluoropicolinamide

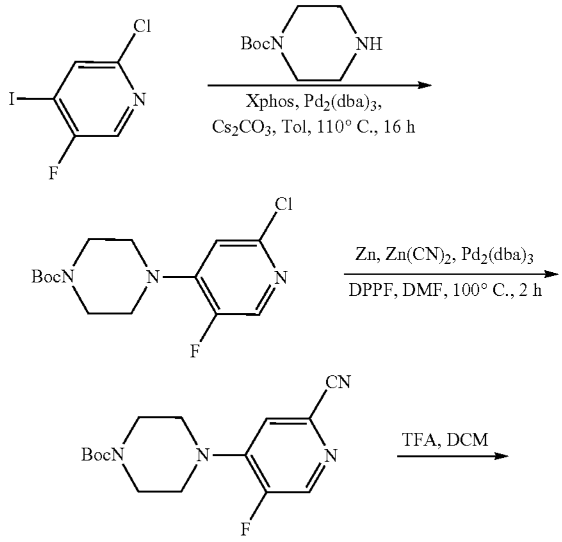

-continued

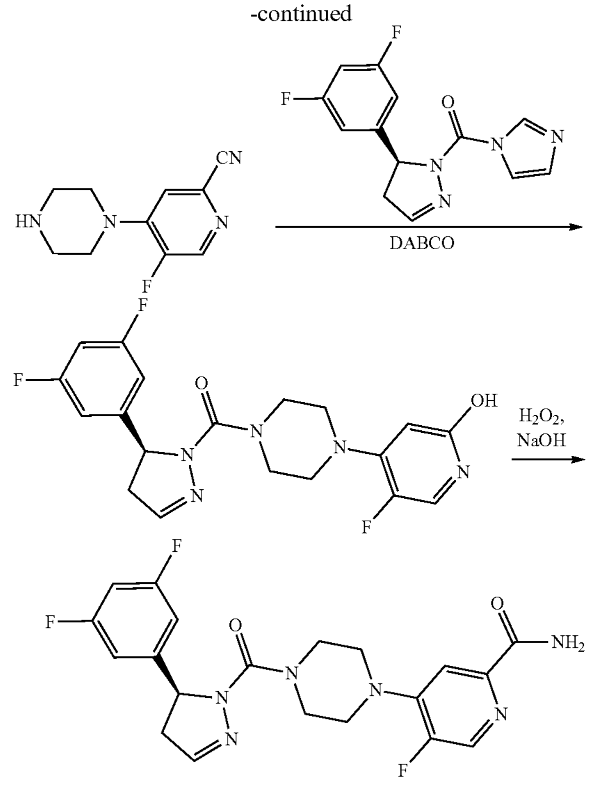

Step 1: 2-chloro-5-fluoro-4-iodopyridine (1.84 g, 7.16 mmoL) and tert-butyl piperazine-1-carboxylate (2.0 g, 10.7 mmoL), $Pd_2(dba)_3$ (655 mg), Xphos (341 mg) and $Cs_2CO_3$ (3.49 g, 10.74 mmoL) were mixed in 30 mL toluene. Let it stir at 110° C. for 16 h. The solvent was evaporated to dryness and purified by chromatography (PE/EA=4/1) to give 1.5 g brown oil. Yield: 66.4%. LC-MS (m/z): 316.4 $[M+H]^+$.

Step 2: To a stirred solution of tert-butyl 4-(2-chloro-5-fluoropyridin-4-yl)piperazine-1-carboxylate (640 mg, 2 mmol) and $Zn(CN)_2$ (240 mg, 2 mmol) in DMF (10 mL) were added Zn power (30 mg, 0.5 mmol), $Pd_2(dba)_3$ (180 mg, 0.2 mmol) and DPPF (110 mg, 0.2 mmoL) at room temperature under $N_2$ atmosphere. The resulting mixture was stirred for additional 2 h at 100° C. The mixture was allowed to cool down to room temperature. The resulting mixture was filtered, the filter cake was washed with EA (3×50 mL). The filtrate was concentrated under reduce pressure. The residue was purified by column chromatography (PE/EA=82/18) to afford 400 mg tert-butyl 4-(2-cyano-5-fluoropyridin-4-yl)piperazine-1-carboxylate as yellow solid (yield: 35.3%). LC-MS (m/z): 307.4 $[M+H]^+$.

Step 3 and step 4: (S)-4-(4-(5-(3,5-difluorophenyl)-4,5-dihydro-1H-pyrazole-1-carbonyl)piperazin-1-yl)-5-fluoro picolinonitrile was synthesized as an off-white solid according to the procedure for compound 63. Yield: 21.7%. $^1H$ NMR (400 MHz, Chloroform-d) δ 8.27 (d, J=5.4 Hz, 1H), 7.12 (d, J=7.1 Hz, 1H), 6.87 (t, J=1.7 Hz, 1H), 6.84-6.76 (m, 2H), 6.71 (tt, J=8.8, 2.3 Hz, 1H), 5.32 (dd, J=11.7, 9.6 Hz, 1H), 3.87 (ddd, J=13.4, 7.3, 3.3 Hz, 2H), 3.72 (ddd, J=13.4, 6.7, 3.3 Hz, 2H), 3.45 (ddd, J=12.4, 6.7, 3.3 Hz, 2H), 3.40-3.26 (m, 3H), 2.71 (ddd, J=18.4, 9.7, 1.6 Hz, 1H). Mass (m/z): 415.2 $[M+H]^+$.

Step 5: (S)-4-(4-(5-(3,5-difluorophenyl)-4,5-dihydro-1H-pyrazole-1-carbonyl)piperazin-1-yl)-5-fluoro picolinonitrile (61 mg, 0.147 mmol) was dissolved in 2 mL MeOH. 0.3 mL 30% $H_2O_2$ and 0.15 mL 2N NaOH was added. Let it stir at r.t for 30 min. The solvent was evaporated to dryness and purified by Prep-TLC (DCM/MeOH=25/1) to give 35 mg of compound 67 as a white solid. Yield: 54.9%. $^1$H NMR (400 MHz, Chloroform-d) δ 8.15 (d, J=5.2 Hz, 1H), 7.71 (d, J=7.7 Hz, 2H), 6.89-6.78 (m, 3H), 6.70 (tt, J=8.9, 2.3 Hz, 1H), 5.68 (s, 1H), 5.32 (dd, J=11.7, 9.8 Hz, 1H), 3.85 (ddd, J=13.3, 7.2, 3.2 Hz, 2H), 3.70 (ddd, J=13.3, 6.7, 3.2 Hz, 2H), 3.45 (ddd, J=12.4, 6.8, 3.3 Hz, 2H), 3.41-3.23 (m, 3H), 2.69 (ddd, J=18.3, 9.8, 1.7 Hz, 1H). Mass (m/z): 433.2[M+H]$^+$.

Example 2

Biological Assays

Compounds 1-67 (denoted as Compound Nos. 1 through 67 in Table 1) of the disclosure were tested for binding and cellular RIP1 inhibitory activity following the experimental procedures described below.

Materials

Cell line: HT-29 (ATCC® HTB-38™)

Culture medium: McCOY's 5A, Gibco, Cat No. 16600-082

FBS, Gibco, Cat No. 10099-141C

Trypsin: Gibco, Cat No. 25200-056

DMSO: Sigma, Cat No. 67-68-5, 1 L

Assay plate: Corning #3903

Compound dilution plate: Corning #3357

Inducers: TNFα, GenScript, Cat No. Z01001-50, SmacM, Cat. No., HY-15989, MedChemExpress (MCE)

Z_VAD FMK, TargetMol, T6013

Cell Titer-Glo® Luminescent Cell Viability Assay Kit: Promega, Cat No. G7573

EnVision: PerkinElmer, 2105-0010

Methods

Cell Seeding

1. HT-29 cells were checked every day to make sure that they were healthy and growing as expected. They were subjected to sub-culturing when they were approximately 80% confluent.

2. The culture medium, McCOY's 5A medium (Gibco, Cat No. 16600-082) with 10% fetal bovine serum or FBS (Gibco, Cat No. 10099-141C), was pre-warmed in a 37° C. water bath for at least 30 min.

3. When the cells had reached a desired level of confluency of 80% in a T75 flask, the medium was aspirated, and the cells were washed with warm phosphate buffered saline or PBS two times.

4. 2-3 ml fresh warm trypsin (Gibco, Cat No. 25200-056) solution was added to the washed cells. The flask with the cells was transferred to a 37° C. incubator.

5. After 5 minutes, the side of the flask was tapped, and the flask was examined under a microscope for detachment of the cells to the flask. If necessary, the cells were kept in the incubator for an additional 5-10 minutes, with occasional tapping, until lifting was complete.

6. The trypsin reaction was neutralized by transferring 6-9 ml cell culture medium to sterile 15 ml conical tubes, and by centrifuging the cell culture at 300×g for 7 minutes to pellet the cells (supernatant decanted).

7. The cells were resuspended in fresh cell culture medium and the cell counting was performed using a hemocytometer.

8. 100 μl of the resuspended cell culture medium containing ~5,000 cells were transferred into each well of the sterile 96-well cell culture plate (Corning 3903) and cultured overnight at 37° C. with 5% CO2.

Compound Titration and Treatment

1. All test compounds were dissolved in DMSO (Dimethyl sulfoxide) to create a 20 mM stock.

2. 3 μl of each compound 20 mM stock was mixed with 27 μl DMSO, and the compound solution was further diluted at a titration ratio of 1:3 (20 μl compound solution+40 μl DMSO) till the 10 points end.

3. All culture medium was removed from assay plates filled with HT-29 cell cultures. The cells were then washed with 1 PBS, and resuspended in fresh, FBS-free McCOY's 5A medium containing a cocktail of TNF-α (10 ng/ml), a SMAC mimetic compound (6 μM) and Z-VAD-fluoromethylketone or zVAD-FMK (10 μM) to stimulate the HT-29 cells to increase RIP1 kinase levels and necroptosis.

4. 0.5 μL of the diluted compound solution was added to the corresponding 96-well assay plates.

5. The assay plates were incubated for 20 hours at 37° C. with 5% CO2.

Cell Viability Detection

1. The CellTiter-Glo® Luminescent Cell Viability Assay was employed to detect the ATP levels of viable HT-29 cells.

2. The CellTiter-Glo® buffer and the lyophilized substrate were equilibrated to room temperature prior to use.

3. The CellTiter-Glo® substrate was resuspended with CellTiter-Glo® buffer, then mixed by gently vortexing to obtain a homogeneous solution.

4. 20 μl the enzyme/substrate mixture was transferred by multi-channel pipetting into 96-well assay plates.

5. The assay plates were placed on an orbital shaker and the contents were shaken for 3 minutes to induce cell lysis.

6. The assay plates were incubated at room temperature for 10 minutes to stabilize the luminescent signal.

7. The luminescence signals were read and recorded with EnVision.

8. The geometric mean EC50 values were calculated from 10 points response dose with duplicates. The ranges of EC50 values of compounds 1-67 are included in Table 2.

The invention claimed is:

1. A compound of formula Ia:

Ia

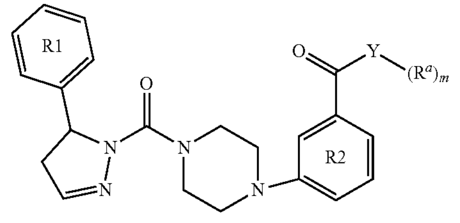

or a salt, hydrate or stereoisomer thereof;

R1 is a 6-membered aryl that is unsubstituted or substituted at C3 and/or C5 with halogen or CN, or a 6-membered heteroaryl that comprises 1 nitrogen heteroatom and that is unsubstituted or substituted at C3 and/or C5 with halogen or CN;

R2 is a 6-membered aryl that is unsubstituted or substituted with halogen or C1-C3 alkoxy, or a 6-membered heteroaryl that comprises 1 or 2 nitrogen heteroatoms and that is unsubstituted or substituted with halogen or C1-C3 alkoxy;

Y is O or N;

when Y is N, m is 2, and

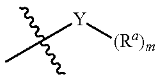
is
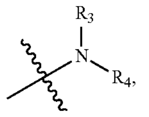

R3 and R4 are independently H or alkyl or cycloalkyl or —$OR^s$, wherein $R^s$ is $C_1$-$C_6$ alkyl optionally substituted with halogen and/or $C_3$-$C_6$ cycloalkyl; wherein the alkyl and cycloalkyl are each independently substituted with 0-3 substituents selected from halogen, —R'—OR', =O, ,=N—OR', —NR'R", —SR'—SiR'R"R", —OC(O)R', —C(O)R'—CO2R'—CONR'R", —OC(O)NR'R", —NR"C(O)R', —NR'—C(O)NR"R"', —NR'—SO2NR"', —NR"CO2R', —NH—C(NH2)=NH, —NR'C(NH2)=NH, —NH—C(NH2)=NR', —S(O)R'—SO2R', —SO2NR'R", —NR"SO2R, —CN and —NO2, —CH(Ph)2 perfluoro (C1-C4) alkoxy and perfluoro (C1-C4)alkyl, wherein R3 and R4 may be joined in a heterocycle;

when Y is O, m is 1, and

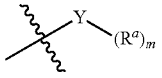
is
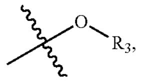

R3 is H or alkyl or cycloalkyl, wherein the alkyl and cycloalkyl are each independently substituted with 0-3 substituents selected from halogen, —R', —OR', =O, ,=N—OR', —NR'R", —SR', —SiR'R"R"', —OC(O)R', —C(O)R', —CO2R', —CONR'R", —OC(O)NR'R", —NR"C(O)R', —NR'—C(O)NR"R"', —NR'SO2NR"', —NR"CO2R', —NH—C(NH2)=NH, —NR'C(NH2)=NH, —NH—C(NH2)=NR', —S(O)R', —SO2R', —SO2NR'R"—NR"SO2R, —CN and —NO2, ,—CH(Ph)2, perfluoro(C1-C4)alkoxy and perfluoro (C1-C4) alkyl;

wherein R', R" and R"' each independently refer to hydrogen, unsubstituted C1-C8 alkyl, unsubstituted C1-C8 heteroalkyl, C1-C8 alkyl substituted with one to three halogens, C1-C8 heteroalkyl substituted with one to three halogens, unsubstituted C6-C14 aryl, C6-C14 aryl substituted with one to three halogens, unsubstituted C1-C8 alkoxy, unsubstituted C1-C8 thioalkoxy groups, or C6-C14 aryl-(C1-C4) alkyl groups, and wherein when R' and R" are attached to the same nitrogen atom, they can be combined with the nitrogen atom to form a 5-, 6- or 7-membered ring.

2. The compound, salt, hydrate, or stereoisomer of claim 1, wherein the compound has following structural formula II(1):

II(1)

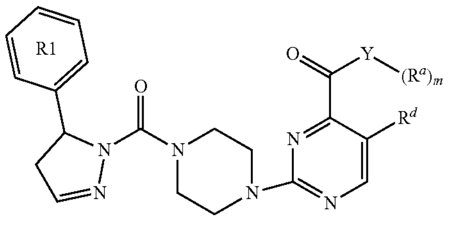

wherein Rd is selected from H, halogen, and C1 to C3 alkoxy.

3. The compound, salt, hydrate, or stereoisomer of claim 1, wherein the compound has the following structural formula II (1) a:

II(1)a

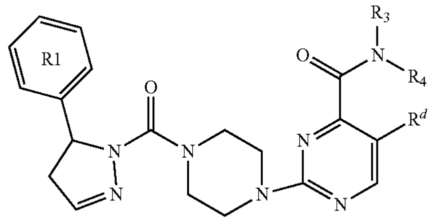

wherein R3 and R4, for each occurrence, are independently selected from: H, $C_1$-$C_3$ alkyl, $C_3$-$C_6$ cycloalkyl, and —O($C_1$-$C_3$alkyl), wherein the $C_1$-$C_3$ alkyl and $C_3$-$C_6$ cycloalkyl are each optionally substituted with 1 to 3 groups selected from halogen, cyano, and 3- to 6-membered heterocyclyl, wherein Rd is selected from H, halogen, and C1 to C3 alkoxy.

4. The compound, salt, hydrate, or stereoisomer of claim 1, wherein the compound has the following structural formula II (1) b:

II(1)b

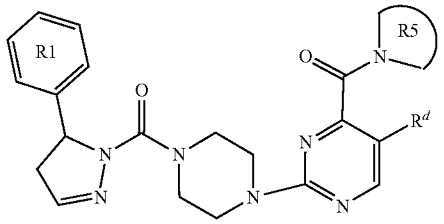

wherein R5 is a 4- to 12-membered heterocycle optionally substituted with OH; CN; $C_3$-$C_6$ cycloalkyl; 3- to 6-membered heterocyclyl; $OR^s$; —C(=O)$NR^pR^q$; —$NR^pR^q$;

C1-C3 alkyl, optionally substituted with CN, $C_3$-$C_6$ cycloalkyl, 3- to 6-membered heterocyclyl, or —$NR^pR^q$; or $C_1$-$C_3$ alkylene, optionally substituted with CN;

wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_3$ alkyl, wherein Rd is selected from H, halogen, and C1 to C3 alkoxy.

5. The compound, salt, hydrate, or stereoisomer of claim 1, wherein the compound has the following structural formula II (2):

II(2)

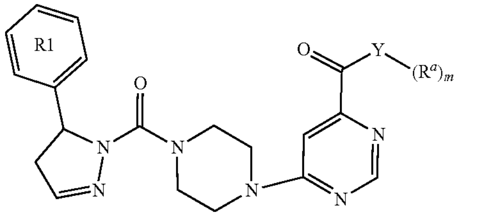

6. The compound, salt, hydrate, or stereoisomer of claim 1, wherein the compound has the following structural formula II (2) a:

II(2)a

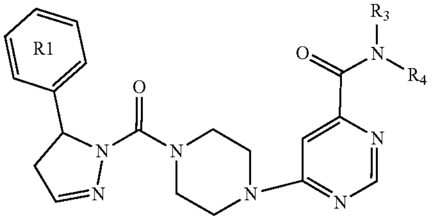

wherein R3 and R4, for each occurrence, are independently selected from: H, $C_1$-$C_3$ alkyl, $C_3$-$C_6$ cycloalkyl, and —O($C_1$-$C_3$ alkyl), wherein the $C_1$-$C_3$ alkyl and $C_3$-$C_6$ cycloalkyl are each optionally substituted with 1 to 3 groups selected from halogen, cyano, and 3- to 6-membered heterocyclyl.

7. The compound, salt, hydrate, or stereoisomer of claim 1, wherein the compound has the following structural formula II(2)b:

II(2)b

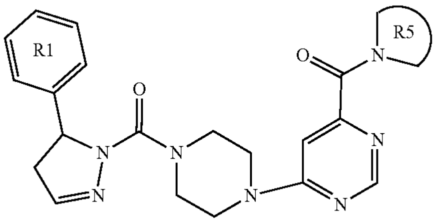

wherein R5 is a 4- to 12-membered heterocycle optionally substituted with OH; CN; $C_3$-$C_6$ cycloalkyl; 3- to 6-membered heterocyclyl; $OR^s$; —C(═O)$NR^pR^q$; —$NR^pR^q$;

$C_1$-$C_3$ alkyl, optionally substituted with CN, $C_3$-$C_6$ cycloalkyl, 3- to 6-membered heterocyclyl, or —$NR^pR^q$; or $C_1$-$C_3$ alkylene, optionally substituted with CN;

wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_3$ alkyl.

8. The compound, salt, hydrate, or stereoisomer of claim 1, wherein the compound has the following structural formula III (1):

III(1)

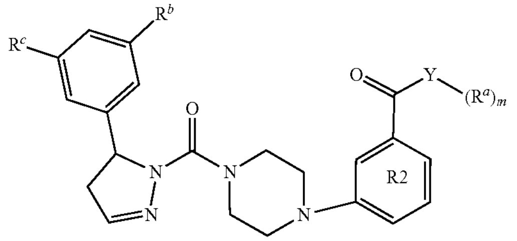

wherein R2 is a 6-membered aryl that is unsubstituted or substituted with halogen or C1-C3 alkoxy, or a 6-membered heteroaryl that comprises 1 or 2 nitrogen heteroatoms and that is unsubstituted or substituted with halogen or C1-C3 alkoxy $R^b$ and $R^c$ are each independently selected from H, halogen, and CN.

9. The compound, salt, hydrate, or stereoisomer of claim 1, wherein the compound has the following structural formula III(1)a:

III(1)a

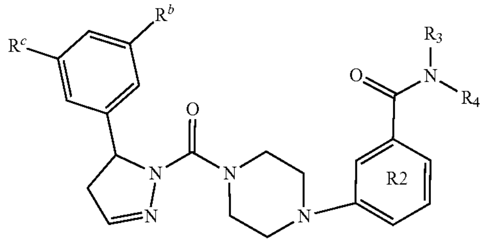

wherein R3 and R4, for each occurrence, are independently selected from: H, $C_1$-$C_3$ alkyl, $C_3$-$C_6$ cycloalkyl, and —O($C_1$-$C_3$ alkyl), wherein the $C_1$-$C_3$ alkyl and $C_3$-$C_6$ cycloalkyl are each optionally substituted with 1 to 3 groups selected from halogen, cyano, and 3- to 6-membered heterocyclyl, wherein $R^b$ and $R^c$ are each independently selected from H, halogen, and CN.

10. The compound, salt, hydrate, or stereoisomer of claim 1, wherein the compound has the following structural formula III (1) b:

III(1)b

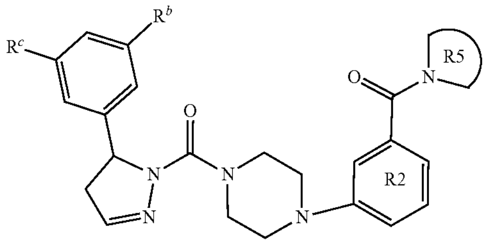

wherein R5 is a 4- to 12-membered heterocycle optionally substituted with OH; CN; $C_3$-$C_6$ cycloalkyl; 3- to 6-membered heterocyclyl; $OR^s$; —C(═O) $NR^pR^q$; —$NR^pR^q$;

$C_1$-$C_3$ alkyl, optionally substituted with CN, $C_3$-$C_6$ cycloalkyl, 3- to 6-membered heterocyclyl, or —$NR^pR^q$; or C1-C3 alkylene, optionally substituted with CN;

wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_3$ alkyl, wherein $R^b$ and $R^c$ are each independently selected from H, halogen, and CN.

11. The compound, salt, hydrate, or stereoisomer of claim 1, wherein the compound has the following structural formula III(2):

III(2)

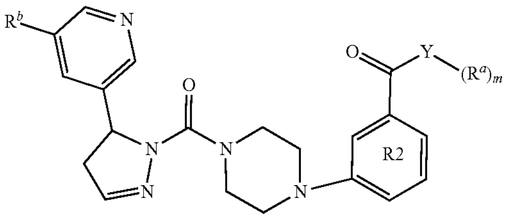

wherein R2 is a 6-membered aryl that is unsubstituted or substituted with halogen or C1-C3 alkoxy, or a 6-membered heteroaryl that comprises 1 or 2 nitrogen heteroatoms and that is unsubstituted or substituted with halogen or C1-C3 alkoxy, and $R^b$ is selected from H, halogen, and CN.

12. The compound, salt, hydrate, or stereoisomer of claim 1, wherein the compound has the following structural formula III(2)a:

III(2)a

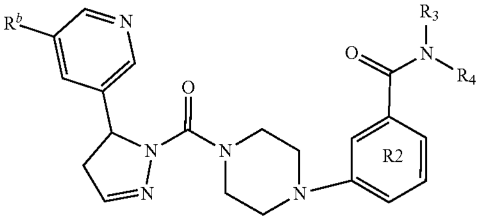

wherein R3 and R4, for each occurrence, are independently selected from: H, $C_1$-$C_3$ alkyl, $C_3$-$C_6$ cycloalkyl, and —O($C_1$-$C_3$ alkyl), wherein the $C_1$-$C_3$ alkyl and $C_3$-$C_6$ cycloalkyl are each optionally substituted with 1 to 3 groups selected from halogen, cyano, and 3- to 6-membered heterocyclyl, wherein $R^b$ is selected from H, halogen, and CN.

13. The compound, salt, hydrate, or stereoisomer of claim 1, wherein the compound has the following structural formula III(2)b:

III(2)b

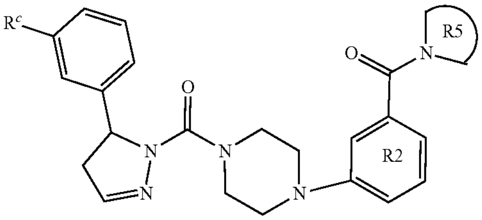

wherein R5 is a 4- to 12-membered heterocycle optionally substituted with OH; CN; $C_3$-$C_6$ cycloalkyl; 3- to 6-membered heterocyclyl; $OR^s$; —C(═O)$NR^pR^q$; —$NR^pR^q$;

$C_1$-$C_3$ alkyl, optionally substituted with CN, $C_3$-$C_6$ cycloalkyl, 3- to 6-membered heterocyclyl, or —$NR^pR^q$; or $C_1$-$C_3$ alkylene, optionally substituted with CN;

wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_3$ alkyl, wherein $R^c$ is selected from H, halogen, and CN.

14. The compound, salt, hydrate, or stereoisomer of claim 1, wherein the compound has the following structural formula IV (1):

IV(1)

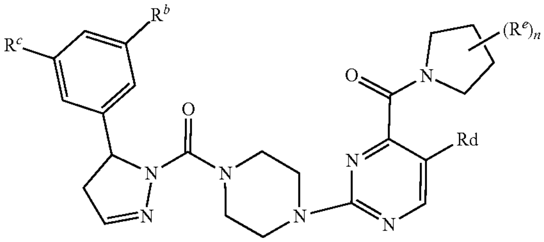

wherein $R^b$ and $R^c$ are each independently selected from H, halogen and CN; Rd is selected from H, halogen, and C1 to C3 alkoxy; and R3 and R4 join to form a 5-membered heterocyclyl substituted with n number of $R^e$, wherein $R^e$ is selected from OH; CN; $C_3$-$C_6$ cycloalkyl; 3- to 6-membered heterocyclyl; $OR^s$; —C(═O)$NR^pR^q$; —$NR^pR^q$;

$C_1$-$C_8$alkyl, optionally substituted with CN, $C_3$-$C_6$ cycloalkyl, 3- to 6-membered heterocyclyl, or —$NR^pR^q$;

or $C_1$-$C_3$ alkylene, optionally substituted with CN;

wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_3$ alkyl; and wherein n is 0, 1, or 2.

15. The compound, salt, hydrate, or stereoisomer of claim 1, wherein the compound has the following structural formula IV (2):

IV(2)

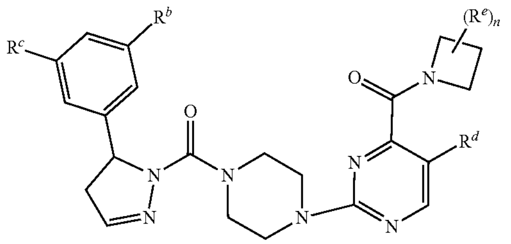

wherein $R^b$ and $R^c$ are each independently selected from H, halogen and CN; Rd is selected from H, halogen, and C1 to C3 alkoxy; and R3 and R4 join to form a 4-membered heterocyclyl substituted with n number of $R^e$, wherein $R^e$ is selected from OH; CN; $C_3$-$C_6$ cycloalkyl; 3- to 6-membered heterocyclyl; $OR^s$; $—C(=O)NR^pR^q$; $—NR^pR^q$;

$C_1$-$C_3$ alkyl, optionally substituted with CN, $C_3$-$C_6$ cycloalkyl, 3- to 6-membered heterocyclyl, or $—NR^pR^q$; and $C_1$-$C_3$ alkylene, optionally substituted with CN;

wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_8$alkyl; and wherein n is 0, 1, or 2.

16. The compound, salt, hydrate, or stereoisomer of claim 1, wherein the compound has the following structural formula IV(3):

IV(3)

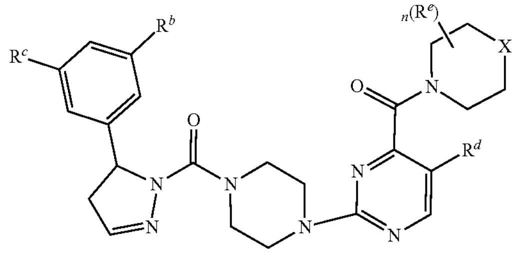

wherein $R^b$ and $R^c$ are each independently selected from H, halogen and CN; Rd is selected from H, halogen, and C1 to C3 alkoxy; X is C, N, or O; and R3 and R4 join to form a 6-membered heterocyclyl substituted with n number of $R^e$, wherein $R^e$ is selected from OH; CN; $C_3$-$C_6$ cycloalkyl; 3- to 6-membered heterocyclyl; $OR^s$; $—C(=O)NR^pR^q$; $—NR^pR^q$;

$C_1$-$C_3$ alkyl, optionally substituted with CN, $C_3$-$C_6$ cycloalkyl, 3- to 6-membered heterocyclyl, or $—NR^pR^q$; and $C_1$-$C_3$ alkylene, optionally substituted with CN;

wherein $R^s$ is $C_1$-$C_3$ alkyl optionally substituted with halogen and $C_3$-$C_6$ cycloalkyl, wherein $R^p$ and $R^q$ each are independently selected from H and $C_1$-$C_8$alkyl; and wherein n is 0, 1, or 2.

17. The compound, salt, hydrate, or stereoisomer of claim 1, wherein the compound has the following structural formula IV(4):

IV(4)

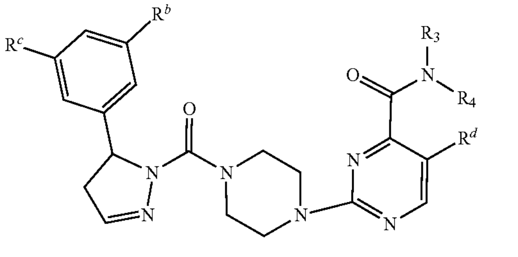

wherein $R^b$ and $R^c$ are each independently selected from H, halogen and CN; Rd is selected from H, halogen, and C1 to C3 alkoxy; and wherein R3 and R4, for each occurrence, are independently selected from: H, $C_1$-$C_3$ alkyl, $C_3$-$C_6$ cycloalkyl, and $—O(C_1$-$C_3$ alkyl), wherein the $C_1$-$C_3$ alkyl and $C_3$-$C_6$ cycloalkyl are each optionally substituted with 1 to 3 groups selected from halogen, cyano and 3- to 6-membered heterocyclyl.

18. The compound, salt, hydrate, or stereoisomer of claim 1, wherein:

when Y is N, m is 2, and

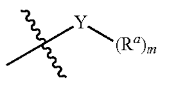 is 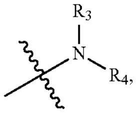

R3 and R4, for each occurrence, are independently selected from: H; $C_1$-$C_6$ alkyl; and $C_3$-$C_6$ cycloalkyl; and $—OR^s$; wherein the $C_1$-$C_6$ alkyl and $C_3$-$C_6$ cycloalkyl of R3 and R4 are each optionally substituted with 1 to 3 groups selected from halogen, cyano and 3- to 6-membered heterocyclyl; or R3 and R4 join to form a 4-6 membered heterocyclyl optionally substituted with OH; CN; $C_3$-$C_6$ cycloalkyl; 3- to 6-membered heterocyclyl; $OR^s$; $—C(=O)NR^pR^q$; $—NR^pR^q$; $C_1$-$C_3$ alkyl, optionally substituted with CN, $C_3$-$C_6$ cycloalkyl, 3- to 6-membered heterocyclyl, or $—NR^pR^q$; or $C_1$-$C_3$ alkylene, optionally substituted with CN;

wherein $R^s$ is $C_1$-$C_6$ alkyl optionally substituted with halogen and $C_3$-$C_6$ cycloalkyl; and wherein $R^p$ and $R^q$ each are independently selected from H and $C_1$-$C_6$ alkyl; or when Y is O, m is 1, and

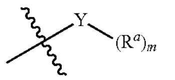 is 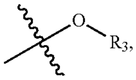

R3 is selected from H, $C_1$-$C_6$ alkyl, and $C_3$-$C_6$ cycloalkyl, wherein the $C_1$-$C_6$ alkyl and $C_3$-$C_6$ cycloalkyl of R3 is optionally substituted with 1 to 3 groups selected from halogen, cyano, and 3- to 6-membered heterocyclyl.

19. The compound, salt, hydrate, or stereoisomer of claim 1, wherein:

when Y is N, m is 2, and

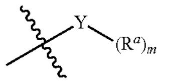 is 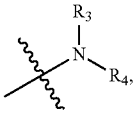

wherein R3 and R4, for each occurrence, are independently selected from: H; $C_1$-$C_3$ alkyl; and $C_3$-$C_4$ cycloalkyl; and $—OR^s$; wherein the $C_1$-$C_3$ alkyl and $C_3$-$C_4$ cycloalkyl of R3 and R4 are each optionally substituted with 1 to 3 groups selected from cyano and 3- to 6-membered heterocyclyl; or R3 and R4 join to form a 4-6 membered heterocyclyl optionally substituted with OH; CN; $C_3$-$C_6$ cycloalkyl; 3- to 6-membered heterocyclyl; $OR^s$; $—C(=O)NR^pR^q$; $—NR^pR^q$; $C_1$-$C_3$ alkyl, optionally substituted with CN, $C_3$-$C_6$ cycloalkyl, 3- to 6-membered heterocyclyl, or $—NR^pR^q$; or $C_1$-$C_3$ alkylene, optionally substituted with CN;

wherein $R^s$ is $C_1$-$C_3$ alkyl optionally substituted with halogen and $C_3$-$C_4$ cycloalkyl; and wherein $R^p$ and $R^q$ each are independently selected from H and $C_1$-$C_3$ alkyl, when Y is O, m is 1, and

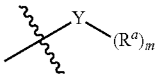 is 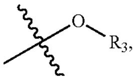

R3 is selected from: H, $C_1$-$C_3$ alkyl, and $C_3$-$C_4$ cycloalkyl, wherein the $C_1$-$C_3$ alkyl and $C_3$-$C_4$ cycloalkyl of R3 is optionally substituted with 1 to 3 groups selected from cyano and 3- to 6-membered heterocyclyl.

20. The compound, salt, hydrate, or stereoisomer of claim 1, wherein R3 and R4, for each occurrence, are independently selected from: H, OH, methyl, ethyl, —$CH_2CN$, —$OCH_3$,

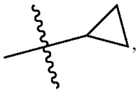 and 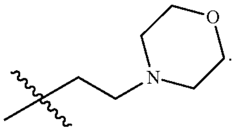

21. The compound, salt, hydrate, or stereoisomer of claim 1, wherein R3 and R4 join to form a 4-6 membered heterocyclyl selected from

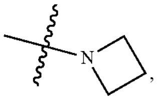
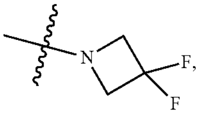
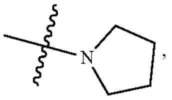
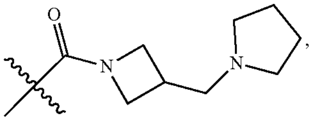
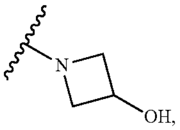
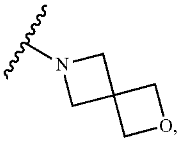
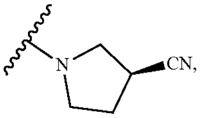
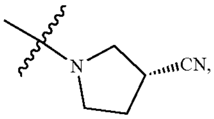
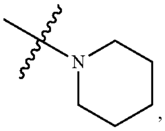
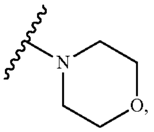
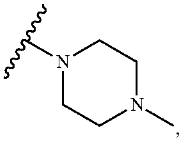
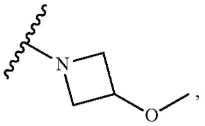

-continued

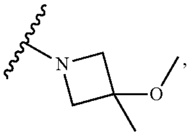
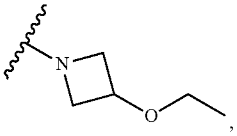
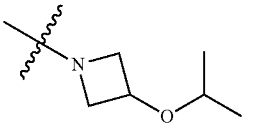
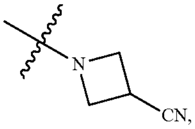
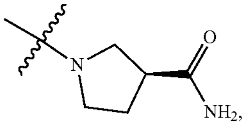
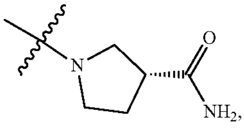
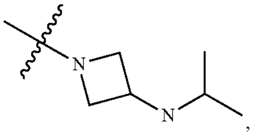
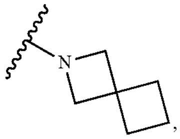
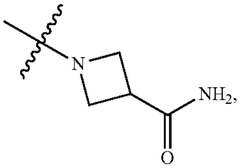
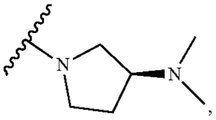
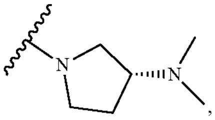
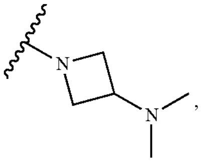
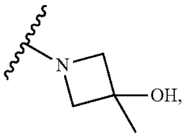
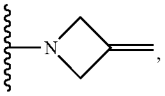
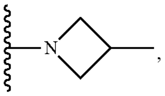
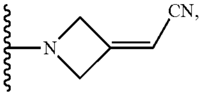
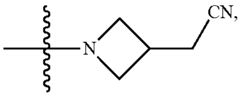
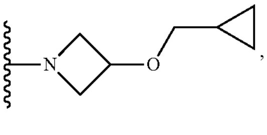
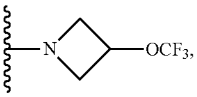
and
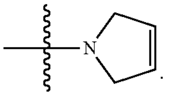

22. The compound, salt, hydrate, or stereoisomer of claim 1, wherein R1 is optionally substituted with F, Cl, or CN; and R2 is optionally substituted with F, Cl, or —$OCH_3$.

23. A compound having a structure selected from:
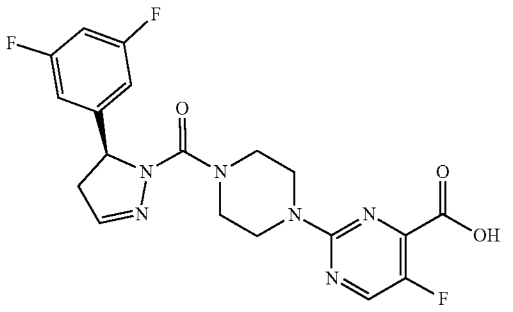
1
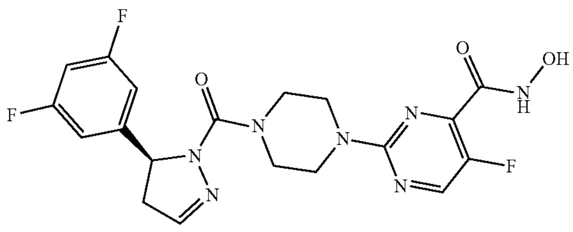
2
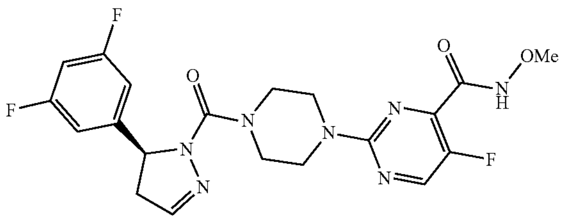
3
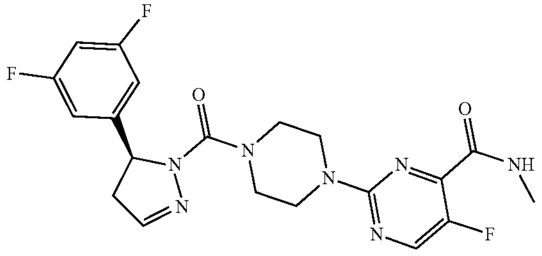
4
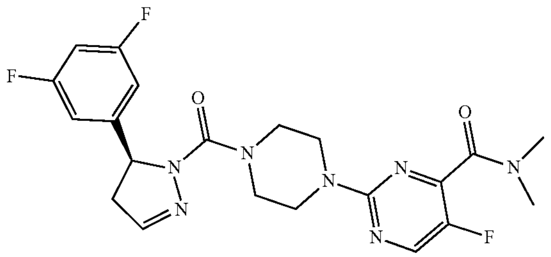
5
-continued
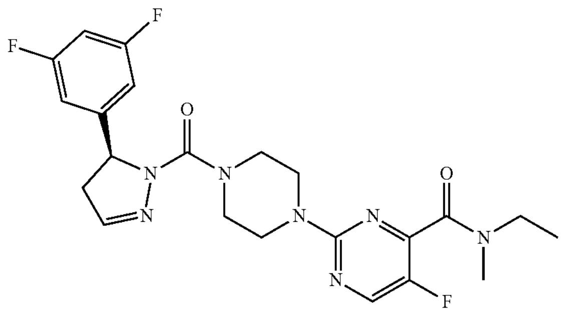
6
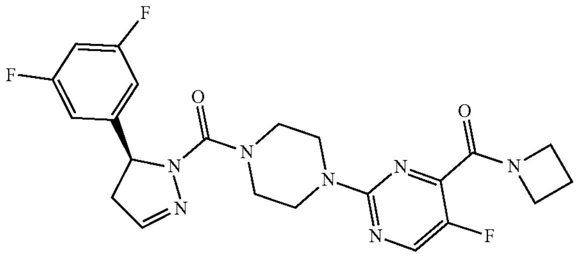
7
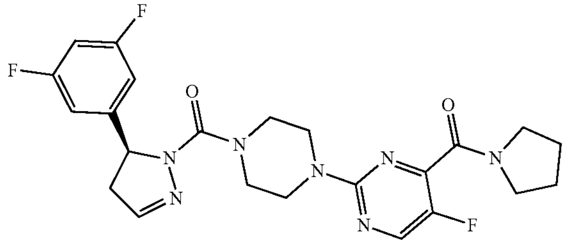
8
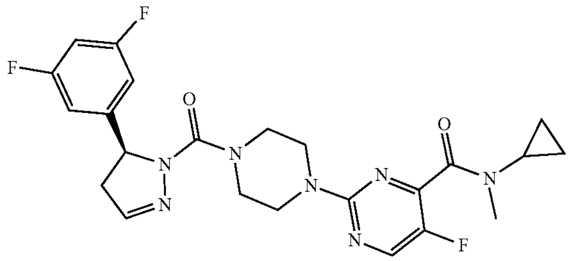
9
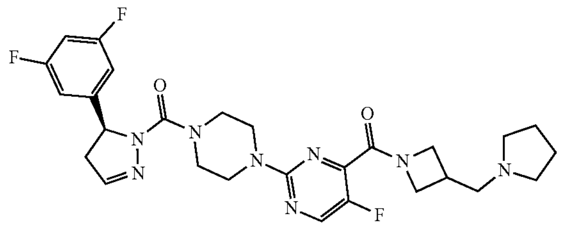
10

-continued
11
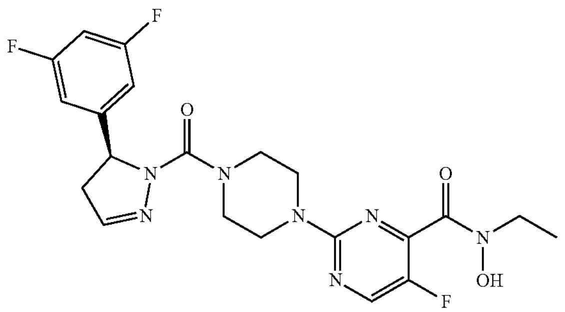
12
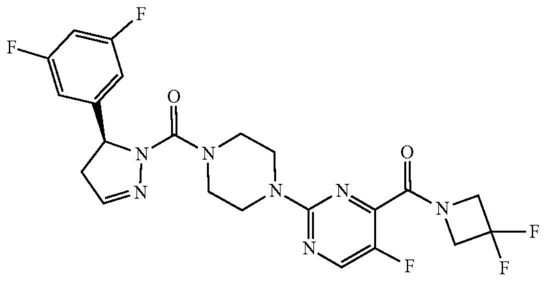
13
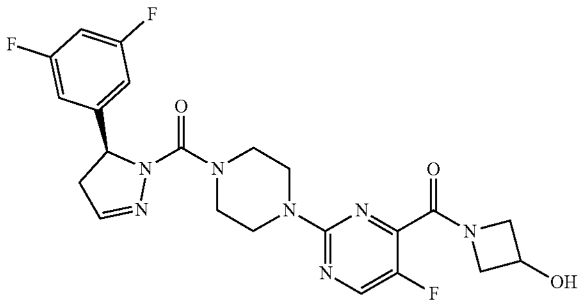
4
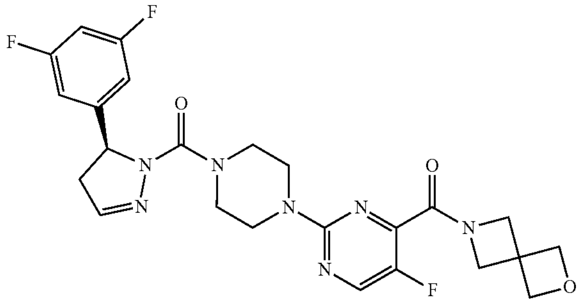
15
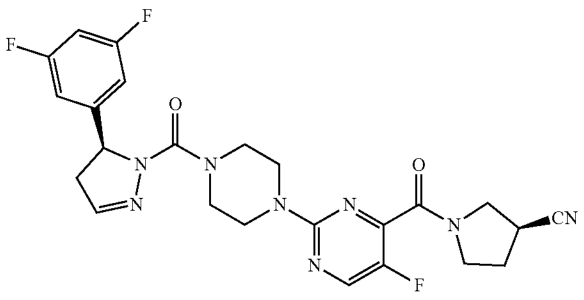
-continued
16
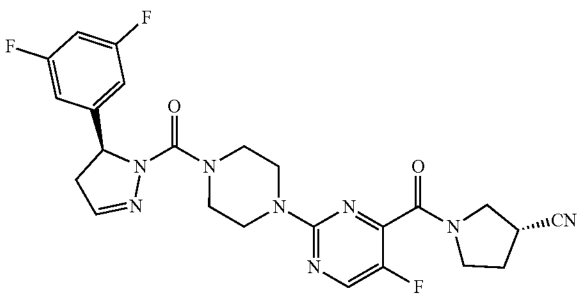
17
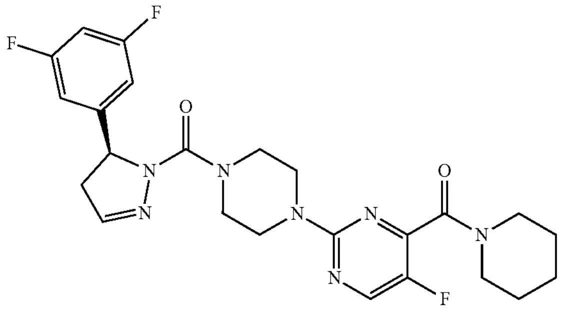
18
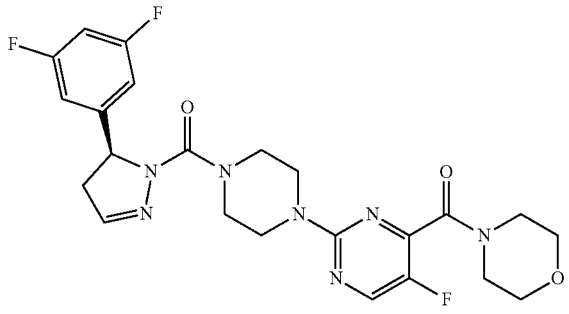
19
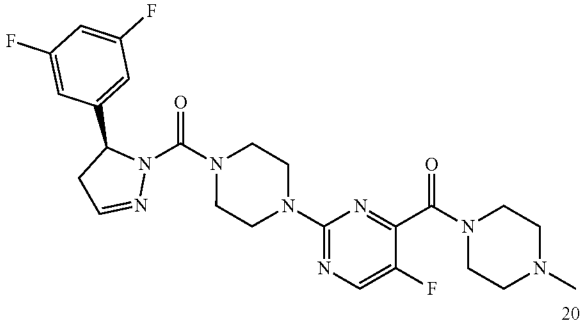
20
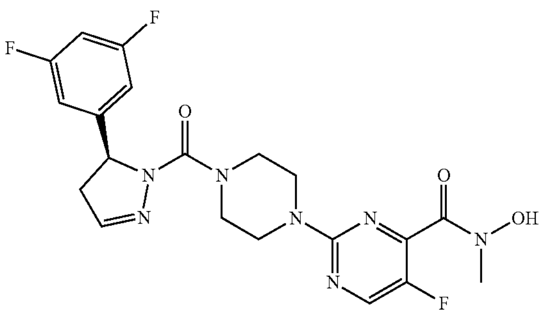

-continued
21
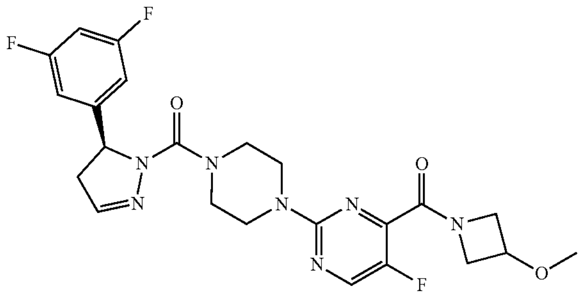
22
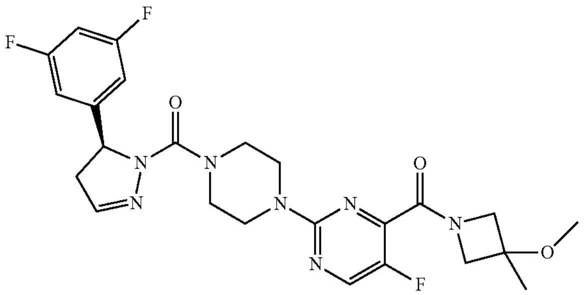
23
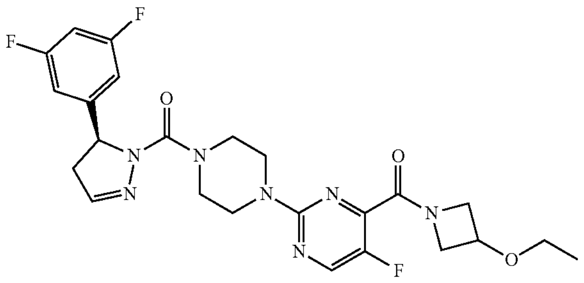
24
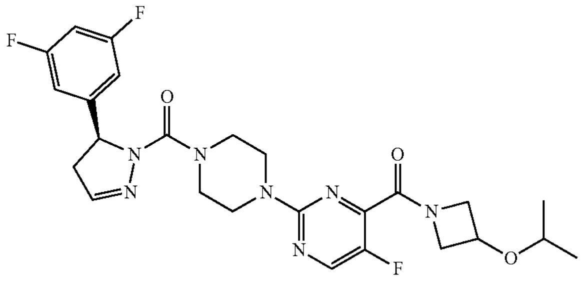
25
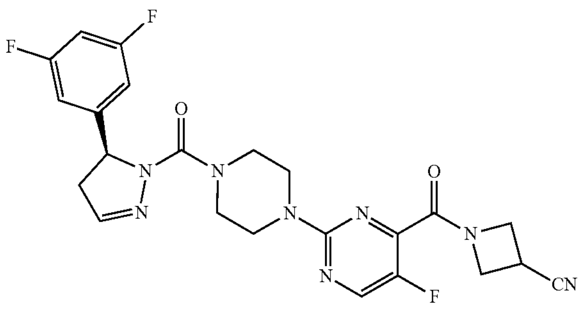
-continued
26
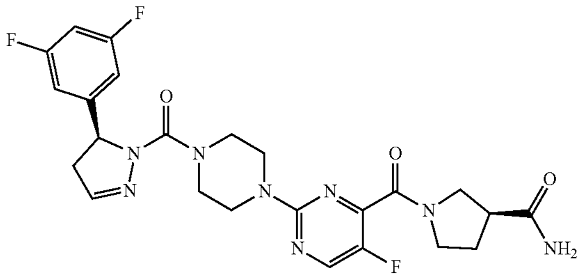
27
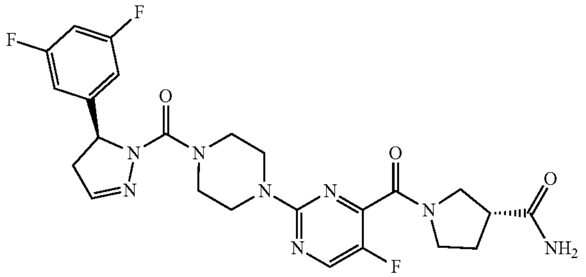
28
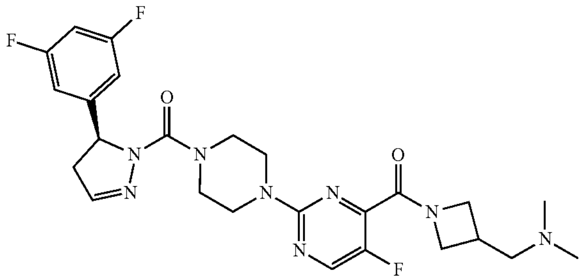
29
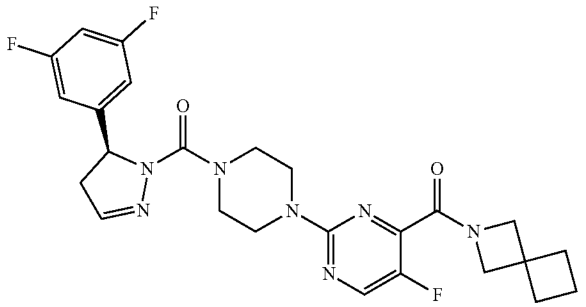
30
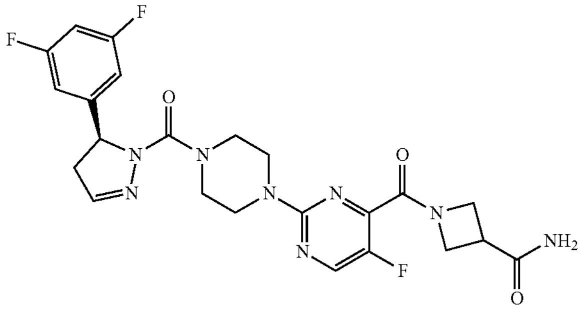

-continued
31
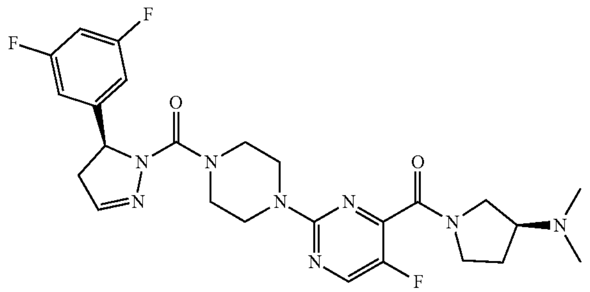
32
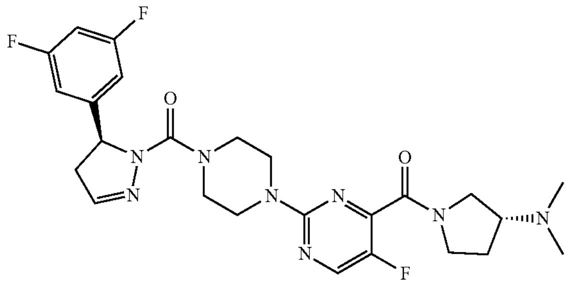
33
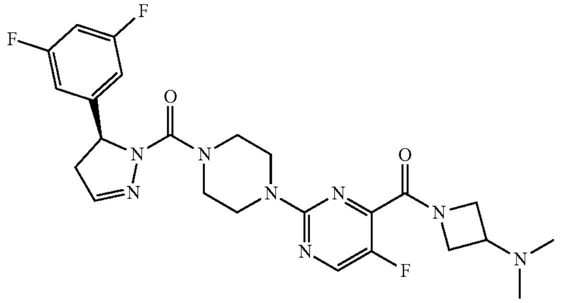
34
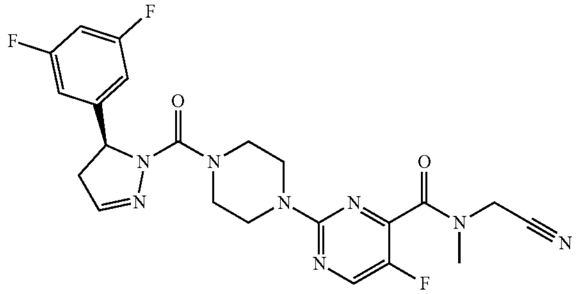
35
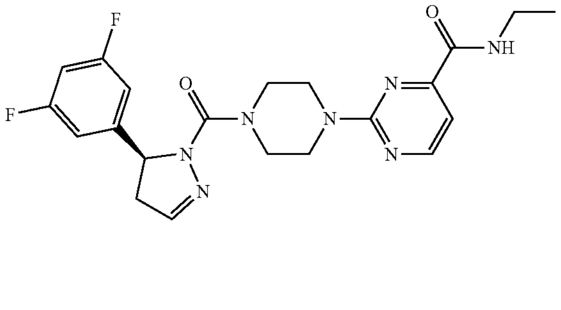
-continued
36
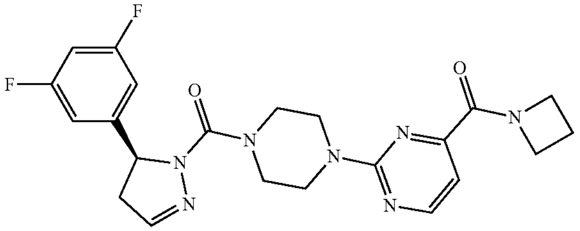
37
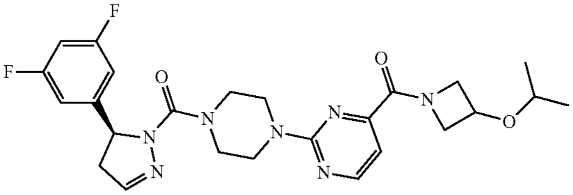
38
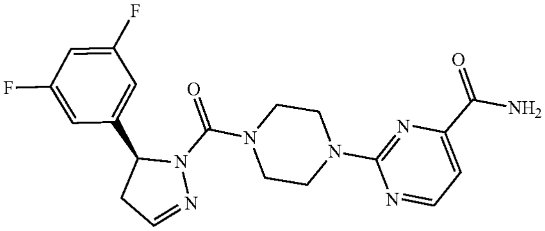
39
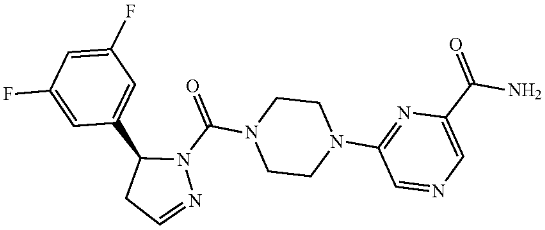
40
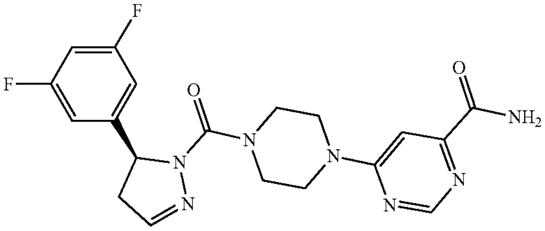
41
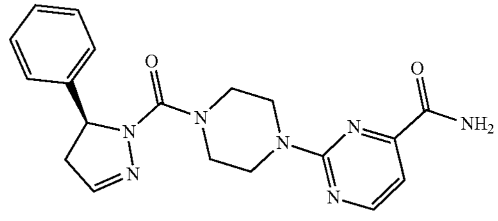

42
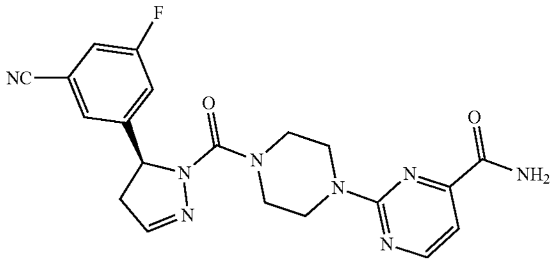
43
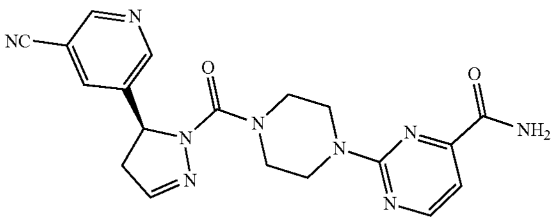
44
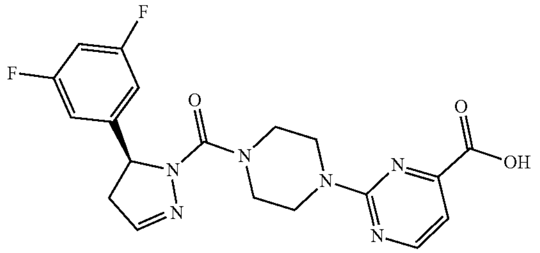
45
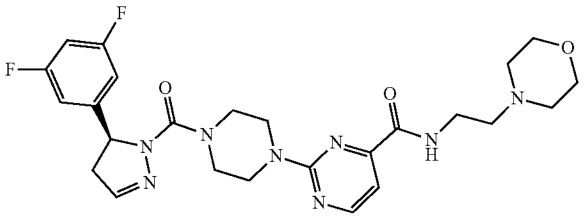
46
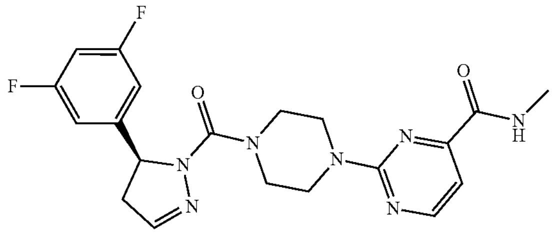
47
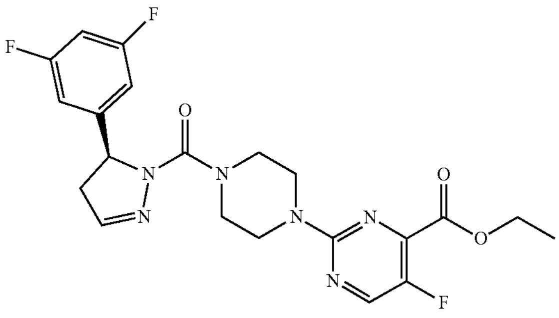
48
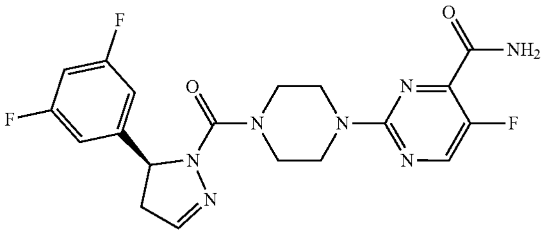
49
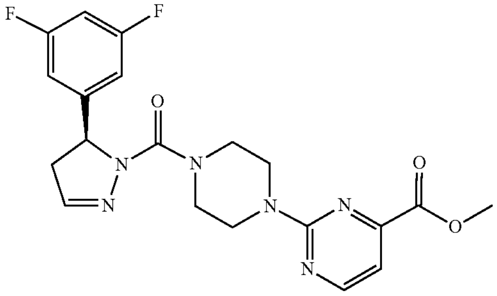
50
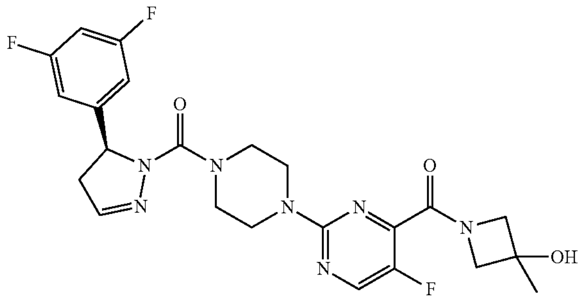
51
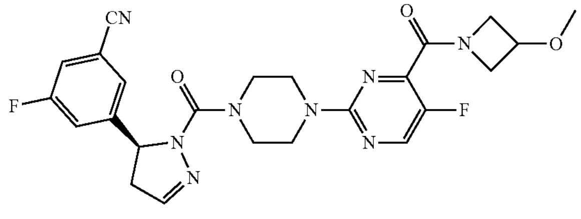
52
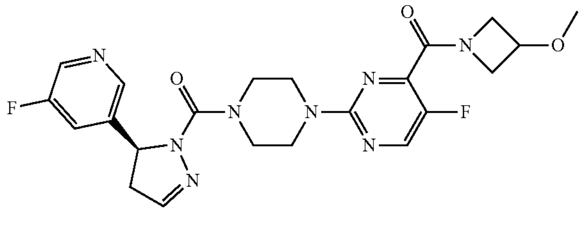
53
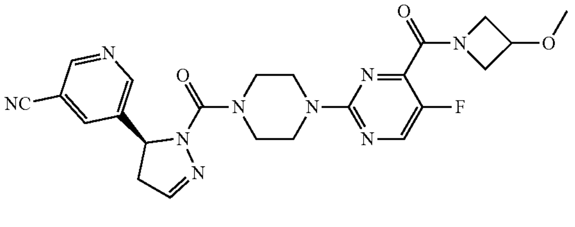

-continued
54
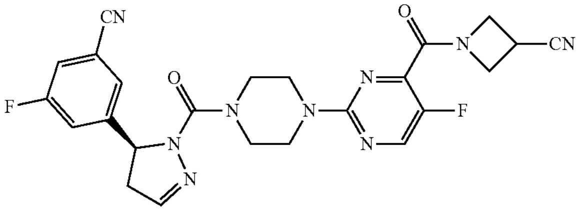
55
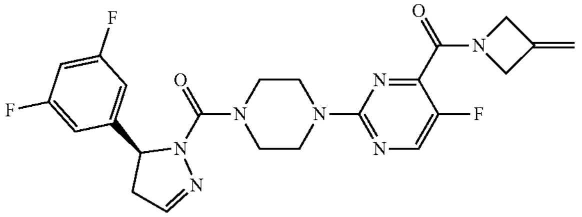
56
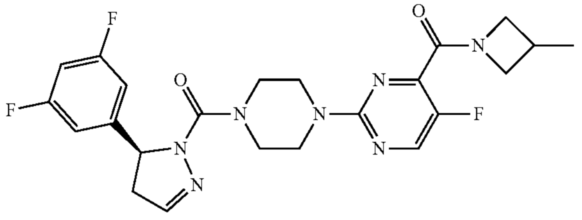
57
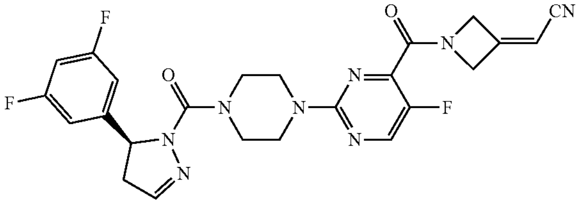
58
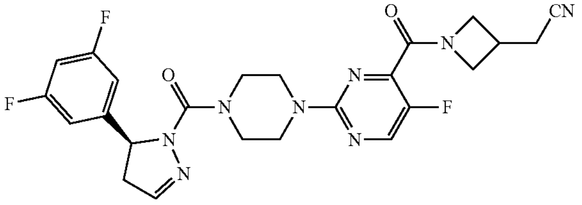
59
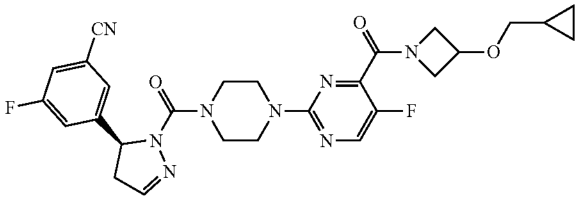
-continued
60
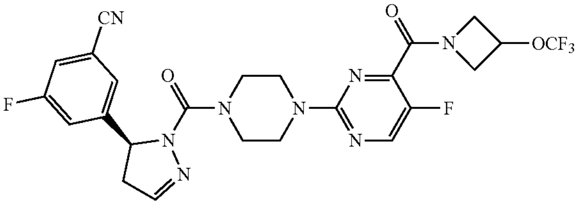
61
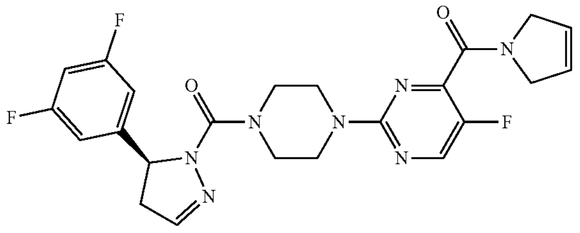
62
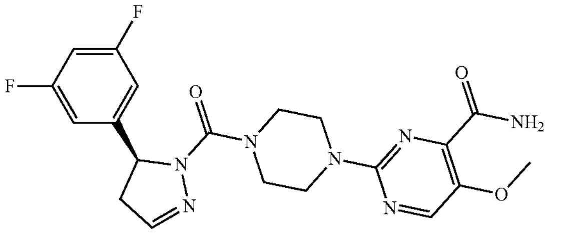
63
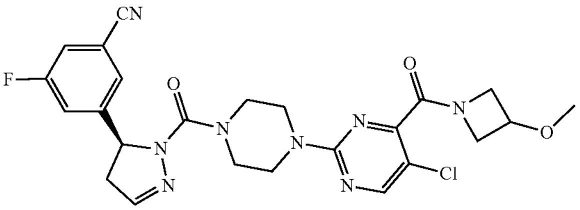
64
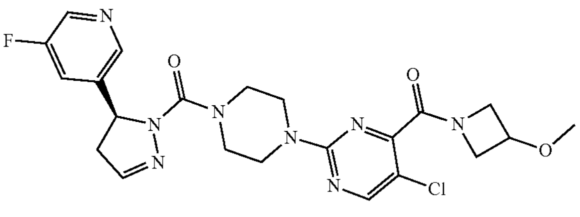
65
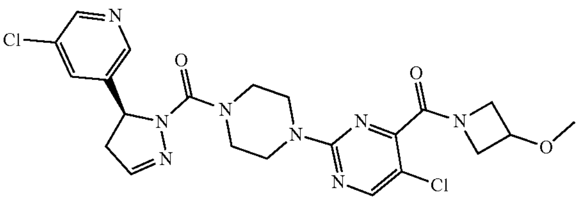

-continued

66

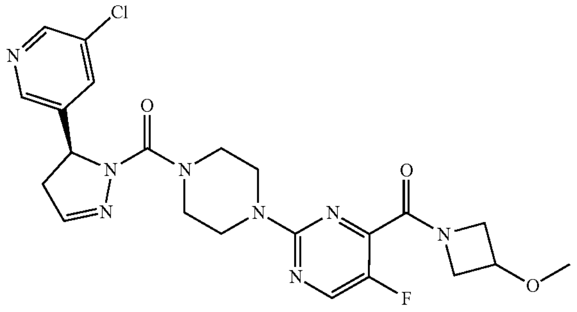

-continued

67

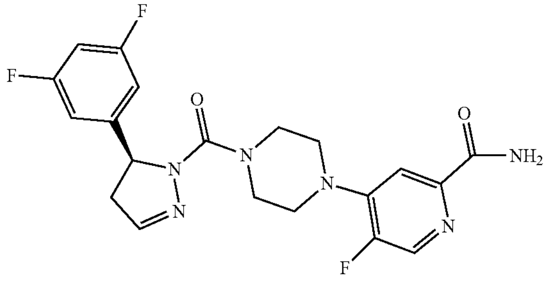

or a salt, hydrate or stereoisomer thereof.

24. A pharmaceutical composition comprising a therapeutically effective amount of a compound of claim 1 and one or more pharmaceutically acceptable excipients, in predetermined, unit dosage form.

25. A method of inhibiting necrosis, necroptosis, ferroptosis, human RIP1, or related indications in a person in need thereof, comprising administering to the person a therapeutically effective amount of the compound, salt, hydrate, or stereoisomer of claim 1.

* * * * *